(12) United States Patent
Lee et al.

(10) Patent No.: US 9,255,084 B2
(45) Date of Patent: Feb. 9, 2016

(54) HETEROCYCLIC COMPOUND AND ORGANIC LIGHT-EMITTING DEVICE CONTAINING THE SAME

(75) Inventors: Sun-Young Lee, Yongin (KR); Yoon-Hyun Kwak, Yongin (KR); Bum-Woo Park, Yongin (KR); Jong-Hyuk Lee, Yongin (KR); Jin-Young Yun, Yongin (KR)

(73) Assignee: Samsung Display Co., Ltd., Samsung-ro, Giheung-Go, Yongin-si, Gyeonggi-Do (KR)

( * ) Notice: Subject to any disclaimer, the term of this patent is extended or adjusted under 35 U.S.C. 154(b) by 260 days.

(21) Appl. No.: 13/438,952

(22) Filed: Apr. 4, 2012

(65) Prior Publication Data
US 2013/0048955 A1 Feb. 28, 2013

(30) Foreign Application Priority Data
Aug. 22, 2011 (KR) .................. 10-2011-0083558

(51) Int. Cl.
*H01L 51/54* (2006.01)
*C07D 403/10* (2006.01)
*C07D 487/04* (2006.01)
*C07C 43/21* (2006.01)
*C07D 493/04* (2006.01)
*C07D 407/10* (2006.01)
*C07D 401/10* (2006.01)
*C07D 495/04* (2006.01)

(52) U.S. Cl.
CPC ............ *C07D 401/10* (2013.01); *C07D 403/10* (2013.01); *C07D 407/10* (2013.01); *C07D 487/04* (2013.01); *C07D 493/04* (2013.01); *C07D 495/04* (2013.01)

(58) Field of Classification Search
None
See application file for complete search history.

(56) References Cited

U.S. PATENT DOCUMENTS

| 5,635,308 A | 6/1997 | Inoue et al. |
| 5,645,948 A | 7/1997 | Shi et al. |
| 5,972,247 A | 10/1999 | Shi et al. |

(Continued)

FOREIGN PATENT DOCUMENTS

| JP | 8-12600 A | 1/1996 |
| JP | 2000-003782 A | 1/2000 |

(Continued)

OTHER PUBLICATIONS

Shaibu et al. J. Org. Chem. 2011, 76, p. 1054.*

(Continued)

*Primary Examiner* — J. L. Yang
(74) *Attorney, Agent, or Firm* — Robert E. Bushnell, Esq.

(57) ABSTRACT

A heterocyclic compound represented by one of Formulae 1-4 below and an organic light-emitting device including an organic layer that includes the heterocyclic compound. The heterocyclic compounds have excellent light-emitting characteristics and excellent electron transporting characteristics, and thus may be used as electron injecting materials or electron transporting materials suitable for all-color fluorescent and phosphorescent devices, such as red, green, blue, and white fluorescent and phosphorescent devices. In particular, the heterocyclic compounds are efficiently used as light-emitting materials of green, blue, and while fluorescent devices. By using the heterocyclic compounds, organic light-emitting devices having high efficiency, low driving voltage, high brightness, and long lifespan may be prepared.

18 Claims, 1 Drawing Sheet

(56) References Cited

U.S. PATENT DOCUMENTS

| | | | |
|---|---|---|---|
| 6,465,115 | B2 | 10/2002 | Shi et al. |
| 6,596,415 | B2 | 7/2003 | Shi et al. |
| 2003/0234607 | A1* | 12/2003 | Kim et al. .................... 313/502 |
| 2007/0273272 | A1 | 11/2007 | Kubota |

FOREIGN PATENT DOCUMENTS

| | | | |
|---|---|---|---|
| KR | 10-2008-0114785 A | 12/2008 |
| KR | 10-2010-0003624 A | 1/2010 |
| KR | 10-2010-0108909 A | 10/2010 |
| KR | 10-2010-0111037 A | 10/2010 |

OTHER PUBLICATIONS http://www.sigmaaldrich.com/catalog/search/substructure/SubstructureSearchPage.

Organic electroluminescent diodes, by C.W. Tang and S.A. Vanslyke; Appl. Phys. Lett. 51, 913 (1987).

Confinement of charge carriers and molecular excitons within 5nm thick emitter layer in organic electroluminescent devices with a double heterostructure, by Chihaya Adachi, Tetsuo Tsutsui, and Shogo Saito; Appl. Phys. Lett. 57,531 (1990).

Synthesis, Characterization, and Electron-Transport Property of Perfluorinated Phenylene Dendrimers, by Youichi Sakamoto et al. J.Am. Chem. Seo 2000, 122, 1832-1833.

Chemistry Letters 2001, 98, Diphenylamino-Substituted 2,5-Diarylsiloles for Single-Layer Organic electroluminescent Devices by Shigehiro Yamaguchi et al.

Chinese Office Action issued on Oct. 26, 2015 by SIPO in connection with CN Patent Application No. 201210159148.0 which also claims Korean Patent Application No. 10-2011-0083558 as its priority document.

* cited by examiner

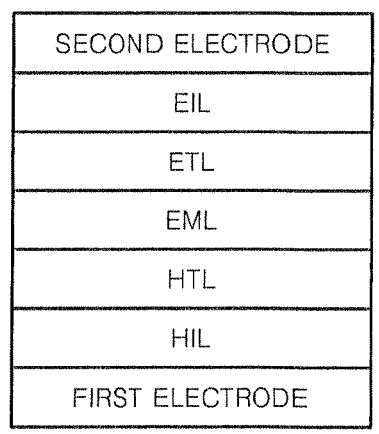

HETEROCYCLIC COMPOUND AND ORGANIC LIGHT-EMITTING DEVICE CONTAINING THE SAME

CLAIM OF PRIORITY

This application claims the benefit of Korean Patent Application No. 10-2011-0083558, filed on Aug. 22, 2011, in the Korean Intellectual Property Office, the disclosure of which is incorporated herein in its entirety by reference.

BACKGROUND OF THE INVENTION

1. Field of the Invention

The present invention relates to a heterocyclic compound represented by Formula 1 and an organic light-emitting device including the heterocyclic compound.

2. Description of the Related Art

Light-emitting devices are self-emission type display devices and have a wide viewing angle, a high contrast ratio, and a short response time. Due to these characteristics, light-emitting devices are drawing more attention. Such light-emitting devices can be roughly classified into inorganic light-emitting devices that include emission layers (EMLs) containing inorganic compounds, and organic light-emitting devices that include EMLs containing organic compounds. Specifically, organic light-emitting devices have higher brightness, lower driving voltages, and shorter response times than inorganic light-emitting devices, and can render multi-colored displays. Thus, much research into such organic light-emitting devices has been conducted. Generally, an organic light-emitting device has a stack structure including an anode, a cathode, and an organic EML interposed therebetween. However, a hole injection layer (HIL) and/or a hole transport layer (HTL) may further be stacked between the anode and the organic EML, and/or an electron transport layer (ETL) may further be stacked between the organic EML and the cathode. In other words, an organic light-emitting device may have a stack structure of anode/HTL/organic EML/cathode or a stack structure of anode/HTL/organic EML/ETL/cathode.

As a material for the organic EML, an anthracene derivative has been used.

However, organic light-emitting devices including such a known organic emission material do not have satisfactory life span, efficiency, and power consumption characteristics, thereby improvement in this regard still being necessary.

SUMMARY OF THE INVENTION

The present invention provides a heterocyclic compound having excellent electrical characteristics, charge transporting capabilities, and light-emission capabilities.

The present invention also provides an organic light-emitting device including the heterocyclic compound.

The present invention also provides a flat panel display device including the organic light-emitting device.

According to an aspect of the present invention, there is provided a heterocyclic compound represented by Formula 1 below.

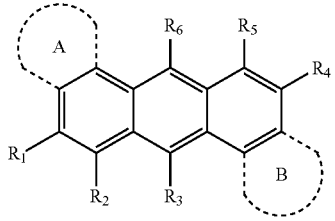

Formula 1

In Formula 1, $R_1$, $R_2$, $R_3$, $R_4$, $R_5$, and $R_6$ are each independently a hydrogen atom, a heavy hydrogen atom, a halogen atom, a cyano group, a substituted or unsubstituted C1-C60 alkyl group, a substituted or unsubstituted C5-C60 aryl group, an amino group substituted with a C5-C60 aryl group, a substituted or unsubstituted C3-C60 heteroaryl group, or a substituted or unsubstituted C6-C60 condensed polycyclic group, and A and B are each independently a substituted or unsubstituted heteroaromatic condensed polycyclic group selected from the group consisting of substituted or unsubstituted dibenzofuran, substituted or unsubstituted dibenzothiophene, substituted or unsubstituted carbazole, substituted or unsubstituted indazole, and substituted or unsubstituted fluorene.

According to an aspect of the present invention, there is provided a heterocyclic compound represented by Formula 2 below.

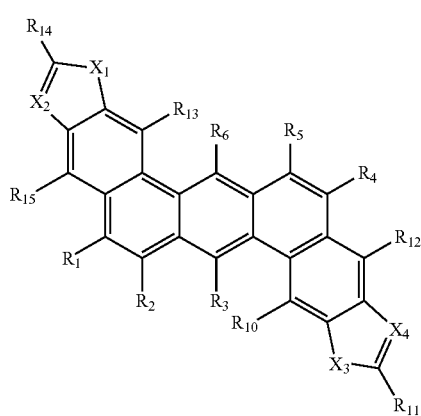

Formula 2

In Formula 2, $R_1$ to $R_6$ and $R_{10}$ to $R_{15}$ are each independently a lone pair electron, a hydrogen atom, a heavy hydrogen atom, a halogen atom, a cyano group, a substituted or unsubstituted C1-C60 alkyl group, a substituted or unsubstituted C5-C60 aryl group, an amino group substituted with a C5-C60 aryl group, a substituted or unsubstituted C3-C60 heteroaryl group, or a substituted or unsubstituted C6-C60 condensed polycyclic group, $X_1$ to $X_4$ are each independently —O—, —N($R_{40}$)—, —C($R_{41}R_{42}$)—, —C$R_{41}$=, or —S—, optionally, $R_{14}$ and $R_{40}$, $R_{41}$, or $R_{42}$; or $R_{11}$ and $R_{40}$, $R_{41}$, or $R_{42}$ may be connected to each other to form a ring, and $R_{40}$ to $R_{42}$ are each independently a lone pair electron, a hydrogen atom, a heavy hydrogen atom, a halogen atom, a cyano group, a substituted or unsubstituted C1-C60 alkyl group, a substituted or unsubstituted C5-C60 aryl group, an amino group substituted with a C5-C60 aryl group, a substituted or unsubstituted C3-C60 heteroaryl group, or a substituted or unsubstituted C6-C60 condensed polycyclic group.

According to an aspect of the present invention, there is provided a heterocyclic compound represented by Formula 3 below.

Formula 3

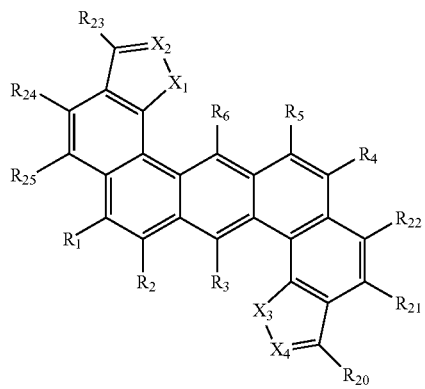

In Formula 3, $R_1$ to $R_6$ and $R_{20}$ to $R_{25}$ are each independently a lone pair electron, a hydrogen atom, a heavy hydrogen atom, a halogen atom, a cyano group, a substituted or unsubstituted C1-C60 alkyl group, a substituted or unsubstituted C5-C60 aryl group, an amino group substituted with a C5-C60 aryl group, a substituted or unsubstituted C3-C60 heteroaryl group, or a substituted or unsubstituted C6-C60 condensed polycyclic group, $X_1$ to $X_4$ are each independently —O—, —N($R_{40}$)—, —C($R_{41}R_{42}$)—, —$CR_{41}$=, or —S—, optionally, $R_{23}$ and $R_{40}$, $R_{41}$, or $R_{42}$; or $R_{20}$ and $R_{40}$, $R_{41}$, or $R_{42}$ may be connected to each other to form a ring, and $R_{40}$ to $R_{42}$ are each independently a lone pair electron, a hydrogen atom, a heavy hydrogen atom, a halogen atom, a cyano group, a substituted or unsubstituted C1-C60 alkyl group, a substituted or unsubstituted C5-C60 aryl group, an amino group substituted with a C5-C60 aryl group, a substituted or unsubstituted C3-C60 heteroaryl group, or a substituted or unsubstituted C6-C60 condensed polycyclic group.

According to an aspect of the present invention, there is provided a heterocyclic compound represented by Formula 1 below.

Formula 4

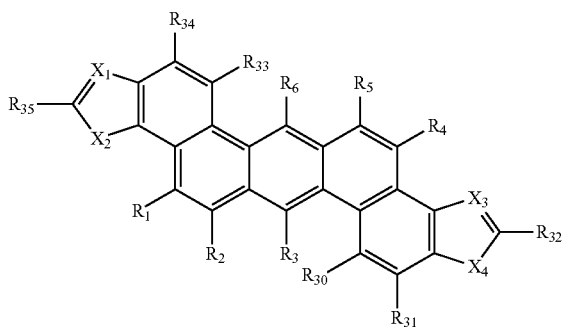

In Formula 4, $R_1$ to $R_6$ and $R_{30}$ to $R_{35}$ are each independently a lone pair electron, a hydrogen atom, a heavy hydrogen atom, a halogen atom, a cyano group, a substituted or unsubstituted C1-C50 alkyl group, a substituted or unsubstituted C5-C60 aryl group, an amino group substituted with a C5-C50 aryl group, a substituted or unsubstituted C3-C60 heteroaryl group, or a substituted or unsubstituted C6-C60 condensed polycyclic group, $X_1$ to $X_4$ are each independently —O—, —N($R_{40}$)—, —C($R_{41}R_{42}$)—, —$CR_{41}$=, or —S—, optionally, $R_{35}$ and $R_{40}$, $R_{41}$, or $R_{42}$; or $R_{32}$ and $R_{40}$, $R_{41}$, or $R_{42}$ may be connected to each other to form a ring, and $R_{40}$ to $R_{42}$ are each independently a lone pair electron, a hydrogen atom, a heavy hydrogen atom, a halogen atom, a cyano group, a substituted or unsubstituted C1-C50 alkyl group, a substituted or unsubstituted C5-C60 aryl group, an amino group substituted with a C5-C50 aryl group, a substituted or unsubstituted C3-C60 heteroaryl group, or a substituted or unsubstituted C6-C60 condensed polycyclic group.

In Formulae 2, 3, and 4, $R_1$ to $R_6$, $R_{10}$ to $R_{15}$, $R_{20}$ to $R_{25}$, and $R_{30}$ to $R_{35}$ are each independently selected from the group consisting of a lone pair electron, a hydrogen atom, a heavy hydrogen atom, a halogen atom, a cyano group, a substituted or unsubstituted C1-C20 alkyl group, and one of Formulae 2a to 2j below.

2a

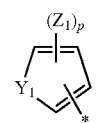

2b

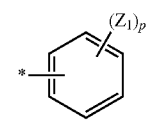

2c

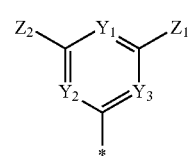

2d

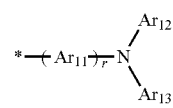

2e

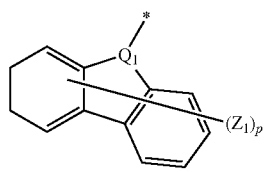

2f

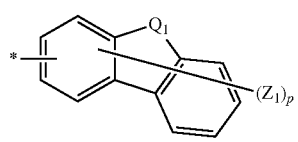

2g

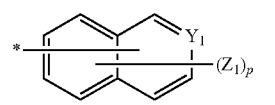

2h

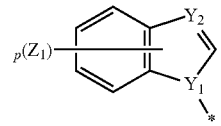

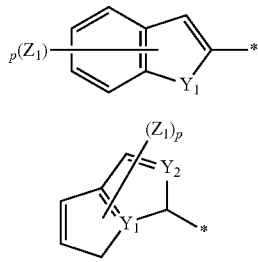
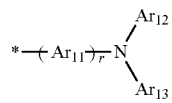
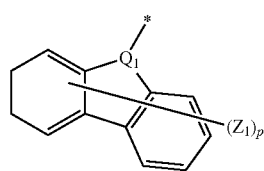
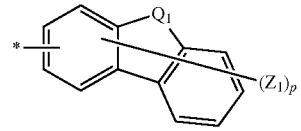
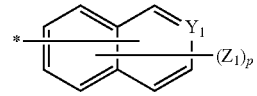
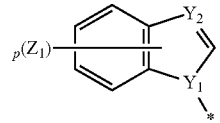
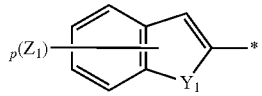
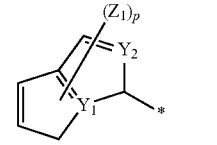

In Formulae 2a to 2j, $Q_1$ is —$C(R_{50})(R_{51})$—, —$N(R_{52})$—, —N(-*)-, —S—, or —O—;

$Y_1$, $Y_2$, and $Y_3$ are each independently —N=, —N(-*)-, —S—, —O—, or —$C(R_{53})$=;

$Z_1$, $Z_2$, $Ar_{12}$, $Ar_{13}$, $R_{50}$, $R_{51}$, $R_{52}$, and $R_{53}$ are each independently selected from the group consisting of a hydrogen atom, a heavy hydrogen atom, a substituted or unsubstituted C1-C20 alkyl group, a substituted or unsubstituted C5-C20 aryl group, a substituted or unsubstituted C3-C20 heteroaryl group, a substituted or unsubstituted C6-C20 condensed polycyclic group, a halogen atom, a cyano group, a nitro group, a hydroxy group, and a carboxy group;

$Ar_{11}$ is selected from the group consisting of a substituted or unsubstituted C1-C20 alkylene group, a substituted or unsubstituted C5-C20 arylene group, and a substituted or unsubstituted C3-C20 heteroarylene group;

p is an integer from 1 to 10;

r is an integer from 0 to 5; and

* is a binding site.

In Formulae 2, 3, and 4, $R_2$, $R_3$, $R_5$, $R_6$, $R_{10}$, $R_{12}$, $R_{13}$, $R_{15}$, $R_{21}$, $R_{22}$, $R_{24}$, $R_{25}$, $R_{30}$, $R_{31}$, $R_{33}$, and $R_{34}$ may be each independently a hydrogen atom or a heavy hydrogen atom. The compounds represented by Formulae 2, 3, and 4 may be symmetrical compounds.

In Formulae 2, 3, and 4, $R_2$, $R_3$, $R_5$, $R_6$, $R_{10}$, $R_{12}$, $R_{13}$, $R_{15}$, $R_{21}$, $R_{22}$, $R_{24}$, $R_{25}$, $R_{30}$, $R_{31}$, $R_{33}$, and $R_{34}$ may be each independently a hydrogen atom or a heavy hydrogen atom, and $R_1$, $R_4$, $R_{11}$, $R_{14}$, $R_{20}$, $R_{23}$, $R_{32}$, and $R_{35}$ may be each independently selected from the group consisting of a lone pair electron, a hydrogen atom, a heavy hydrogen atom, a halogen atom, a cyano group, a substituted or unsubstituted C1-C20 alkyl group, and one of Formulae 2a to 2j below.

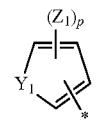
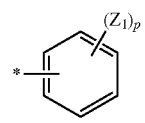
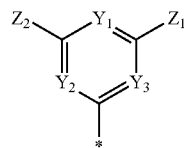

In Formulae 2a to 2j, $Q_1$ is —$C(R_{50})(R_{51})$—, —$N(R_{52})$—, —N(-*)-, —S—, or —O—;

$Y_1$, $Y_2$, and $Y_3$ are each independently —N=, —N(-*)-, —S—, —O—, or —$C(R_{53})$=;

$Z_1$, $Z_2$, $Ar_{12}$, $Ar_{13}$, $R_{50}$, $R_{51}$, $R_{52}$, and $R_{53}$ are each independently selected from the group consisting of a hydrogen atom, a heavy hydrogen atom, a substituted or unsubstituted C1-C20 alkyl group, a substituted or unsubstituted C5-C20 aryl group, a substituted or unsubstituted C3-C20 heteroaryl group, a substituted or unsubstituted C6-C20 condensed polycyclic group, a halogen atom, a cyano group, a nitro group, a hydroxy group, and a carboxy group;

$Ar_{11}$ is selected from the group consisting of a substituted or unsubstituted C1-C20 alkylene group, a substituted or unsubstituted C5-C20 arylene group, and a substituted or unsubstituted C3-C20 heteroarylene group;

p is an integer from 1 to 10; r is an integer from 0 to 5; and * is a binding site.

In Formulae 2, 3, and 4, $R_2$, $R_3$, $R_5$, $R_6$, $R_{10}$, $R_{12}$, $R_{13}$, $R_{15}$, $R_{21}$, $R_{22}$, $R_{24}$, $R_{25}$, $R_{30}$, $R_{31}$, $R_{33}$, and $R_{34}$ may be each independently a hydrogen atom or a heavy hydrogen atom, $R_1$, $R_4$, $R_{11}$, $R_{14}$, $R_{20}$, $R_{23}$, $R_{32}$, and $R_{35}$ may be each independently selected from the group consisting of a lone pair electron, a hydrogen atom, a heavy hydrogen atom, a halogen atom, a cyano group, a substituted or unsubstituted C1-C20 alkyl group, and one of Formulae 2a to 2j below and the compounds represented by Formulae 2, 3, and 4 may be symmetrical compounds.

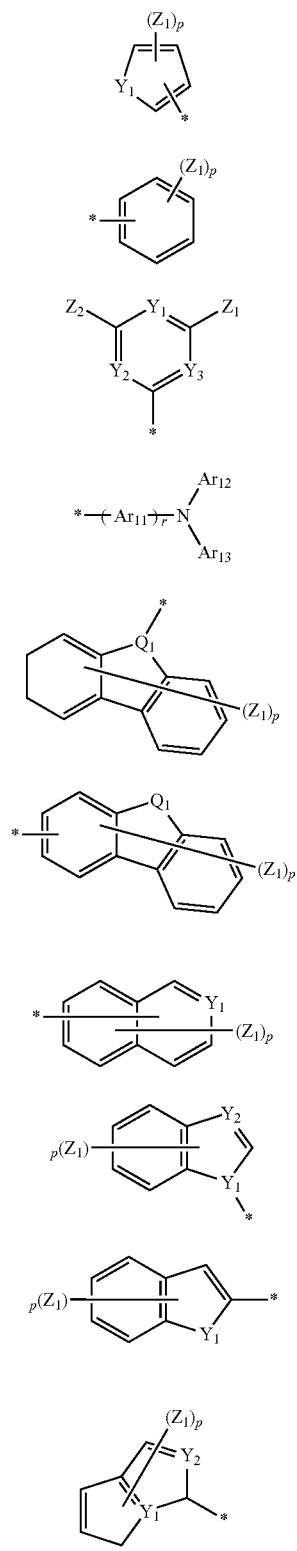

In Formulae 2a to 2j, $Q_1$ is —$C(R_{50})(R_{51})$—, —$N(R_{52})$—, —N(-*)-, —S—, or —O—;

$Y_1$, $Y_2$, and $Y_3$ are each independently —N(-*)-, —S—, —O—, or —$C(R_{53})$=;

$Z_1$, $Z_2$, $Ar_{12}$, $Ar_{13}$, $R_{50}$, $R_{51}$, $R_{52}$, and $R_{53}$ are each independently selected from the group consisting of a hydrogen atom, a heavy hydrogen atom, a substituted or unsubstituted C1-C20 alkyl group, a substituted or unsubstituted C5-C20 aryl group, a substituted or unsubstituted C3-C20 heteroaryl group, a substituted or unsubstituted C6-C20 condensed polycyclic group, a halogen atom, a cyano group, a nitro group, a hydroxy group, and a carboxy group;

$Ar_{11}$ is selected from the group consisting of a substituted or unsubstituted C1-C20 alkylene group, a substituted or unsubstituted C5-C20 arylene group, and a substituted or unsubstituted C3-C20 heteroarylene group;

p is an integer from 1 to 10; r is an integer from 0 to 5; and * is a binding site.

The heterocyclic compound of Formula 1 may be one of the following compounds.

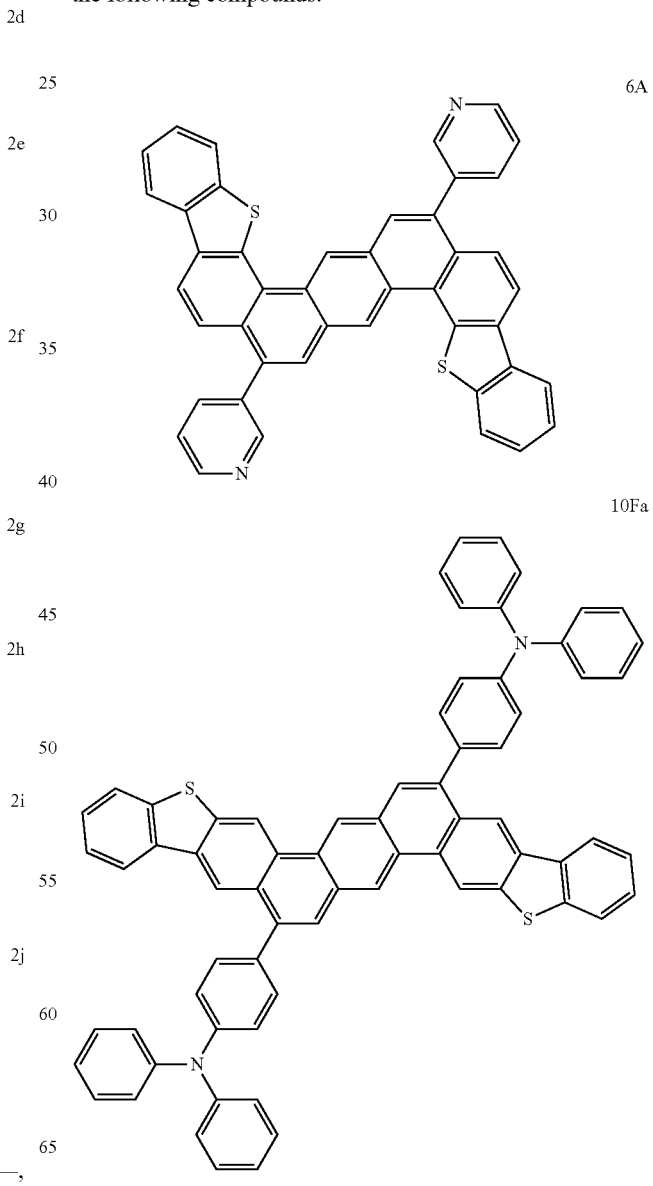

-continued

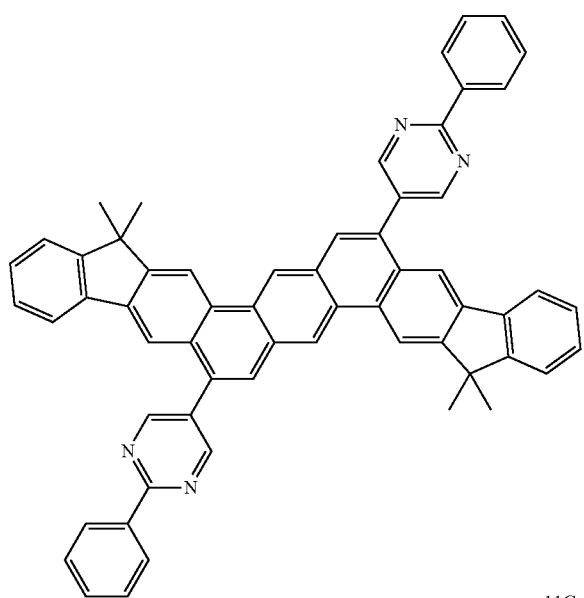

3Ga

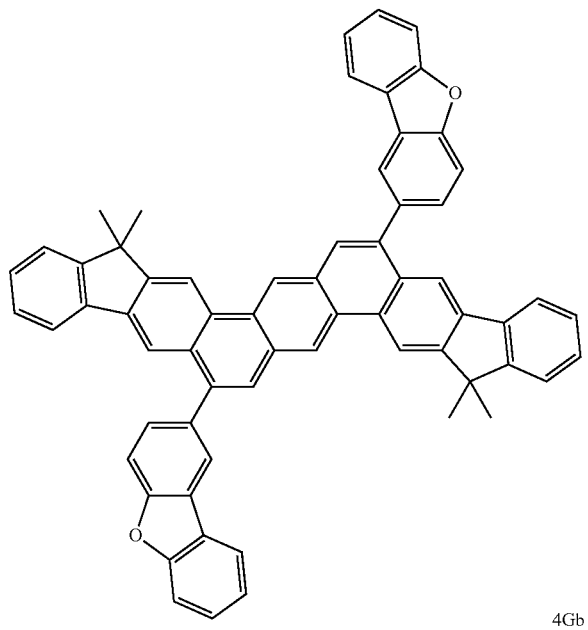

11Ga

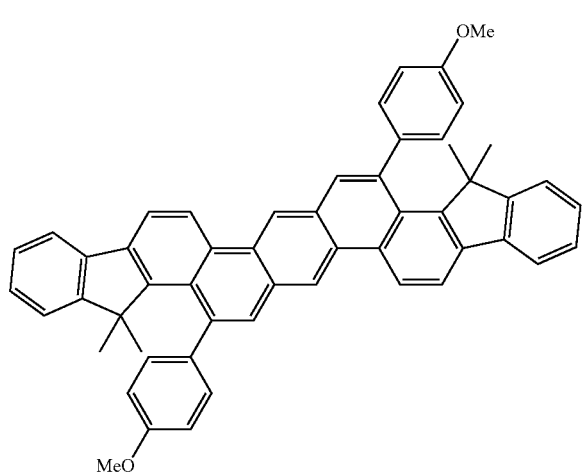

4Gb

According to an aspect of the present invention, there is provided an organic light-emitting device including a first electrode; a second electrode; and an organic layer interposed between the first electrode and the second electrode, wherein the organic layer includes a first layer including the heterocyclic compound represented by Formula 1.

The first layer may include a hole injection layer (HIL), a hole transport layer (HTL), a functional layer having both hole injecting and hole transporting capabilities, an emission layer (EML), an electron injection layer (EIL), an electron transport layer (ETL), or a functional layer having both electron injecting and electron transporting capabilities.

The first layer may be an EML, and the heterocyclic compound of Formula 1 may be used as a fluorescent host or a fluorescent dopant.

The organic layer may include an EML, a HTL, and an ETL, and the first layer may be an EML, wherein the EML may further include an anthracene compound, an arylamine compound, or a styryl compound.

The organic layer may include an EML, a HTL, and an ETL, and the first layer may be an EML, wherein one of the red, green, blue, and white layers of the EML may further include a phosphorescent compound.

The first layer may be a blue EML.

The first layer may be a blue EML, and the heterocyclic compound of Formula 1 may be used as a blue dopant.

The organic layer may include a HIL, a HTL, a functional layer having both hole injecting and hole transporting capabilities, an EML, a hole blocking layer (HBL), an ETL, an EIL, or a combination of at least two thereof.

At least one of the HIL, the HTL, and the functional layer having both hole injecting and hole transporting capabilities may further include a charge-generating material.

The ETL may include an electron-transporting organic material and a metal-containing material.

BRIEF DESCRIPTION OF THE DRAWINGS

The above and other features and advantages of the present invention will become more apparent by describing in detail exemplary embodiments thereof with reference to the attached drawing in which:

FIG. 1 illustrates an organic light-emitting device according to an embodiment of the present invention.

DETAILED DESCRIPTION OF THE INVENTION

As used herein, the term "and/or" includes any and all combinations of one or more of the associated listed items. Expressions such as "at least one of," when preceding a list of elements, modify the entire list of elements and do not modify the individual elements of the list.

Anthracene derivatives are widely known as materials for forming an organic emission layer (EML). PBD, PF-6P, and PyPySPyPy, as well as Alq3, are also widely known as materials for forming an electron transport layer (ETL). For example, an organic light-emitting device manufactured using a compound of phenylanthracene dimer or trimer is widely known. However, such organic light-emitting devices have a narrow energy gap and lower blue-light color purity since two or three oligomeric species of anthracene are linked by conjugation.

In addition, such compounds are highly vulnerable to oxidation and thus are liable to produce impurities, necessitating purification. In order to overcome these drawbacks, organic light-emitting devices manufactured using an anthracene compound including a substituent of naphthalene at 1,9 position or using a diphenylanthracene compound including a substituent of an aryl group at m-position of the phenyl group have been introduced. However, these organic light-emitting devices have lower light-emission efficiency.

In addition, organic light-emitting devices manufactured using a naphthalene-substituted monoanthracene derivative have been introduced. However, the compound has a low light-emission efficiency of about 1 cd/A, and thus such organic light-emitting devices are not suitable for practical use. Organic light-emitting devices manufactured using compounds having a phenylanthracene structure have been introduced. However, these compounds are substituted with an aryl group at m-position, and thereby having a low light-emission efficiency of about 2 cd/A in spite of excellent thermal resistance.

The present invention will now be described in more detail.

According to an embodiment of the present invention, a heterocyclic compound represented by Formula 1 below is provided.

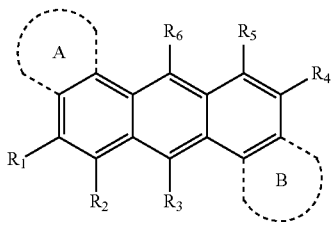

[Formula 1]

In Formula 1, $R_1$, $R_2$, $R_3$, $R_4$, $R_5$, and $R_6$ are each independently a hydrogen atom, a heavy hydrogen atom, a halogen atom, a cyano group, a substituted or unsubstituted C1-C60 alkyl group, a substituted or unsubstituted C5-C60 aryl group, an amino group substituted with a C5-C60 aryl group, a substituted or unsubstituted C3-C60 heteroaryl group, or a substituted or unsubstituted C6-C60 condensed polycyclic group, and
A and B are each independently a substituted or unsubstituted heteroaromatic condensed polycyclic group selected from the group consisting of substituted or unsubstituted dibenzofuran, substituted or unsubstituted dibenzothiophene, substituted or unsubstituted carbazole, substituted or unsubstituted indazole, and substituted or unsubstituted fluorene.

According to an embodiment of the present invention, a heterocyclic compound represented by Formula 2 is provided.

Formula 2

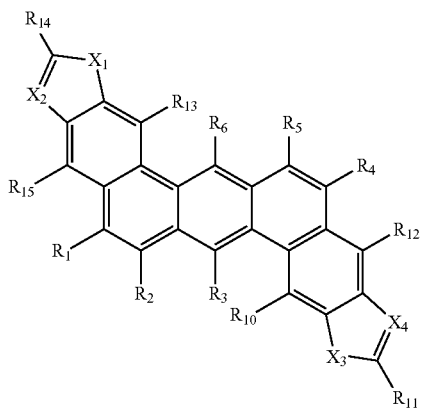

In Formula 2, $R_1$ to $R_6$ and $R_{10}$ to $R_{15}$ are each independently a lone pair electron, a hydrogen atom, a heavy hydro-gen atom, a halogen atom, a cyano group, a substituted or unsubstituted C1-C60 alkyl group, a substituted or unsubstituted C5-C60 aryl group, an amino group substituted with a C5-C60 aryl group, a substituted or unsubstituted C3-C60 heteroaryl group, or a substituted or unsubstituted C6-C60 condensed polycyclic group, $X_1$ to $X_4$ are each independently —O—, —N($R_{40}$)—, —C($R_{41}R_{42}$)—, —C$R_{41}$=, or —S—, optionally, $R_{14}$ and $R_{40}$, $R_{41}$, or $R_{42}$; or $R_{11}$ and $R_{40}$, $R_{41}$, or $R_{42}$ may be connected to each other to form a ring, $R_{40}$ to $R_{42}$ are each independently a lone pair electron, a hydrogen atom, a heavy hydrogen atom, a halogen atom, a cyano group, a substituted or unsubstituted C1-C60 alkyl group, a substituted or unsubstituted C5-C60 aryl group, an amino group substituted with a C5-C60 aryl group, a substituted or unsubstituted C3-C60 heteroaryl group, or a substituted or unsubstituted C6-C60 condensed polycyclic group.

According to an embodiment of the present invention, a heterocyclic compound represented by Formula 3 is provided.

Formula 3

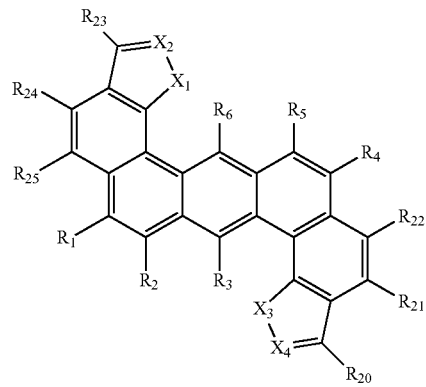

In Formula 3, $R_1$ to $R_6$ and $R_{20}$ to $R_{25}$ are each independently a lone pair electron, a hydrogen atom, a heavy hydrogen atom, a halogen atom, a cyano group, a substituted or unsubstituted C1-C60 alkyl group, a substituted or unsubstituted C5-C60 aryl group, an amino group substituted with a C5-C60 aryl group, a substituted or unsubstituted C3-C60 heteroaryl group, or a substituted or unsubstituted C6-C60 condensed polycyclic group, $X_1$ to $X_4$ are each independently —O—, —N($R_{40}$)—, —C($R_{41}R_{42}$)—, —C$R_{41}$=, or —S—, optionally, $R_{23}$ and $R_{40}$, $R_{41}$, or $R_{42}$; or $R_{20}$ and $R_{40}$, $R_{41}$, or $R_{42}$ may be connected to each other to form a ring, $R_{40}$ to $R_{42}$ are each independently a lone pair electron, a hydrogen atom, a heavy hydrogen atom, a halogen atom, a cyano group, a substituted or unsubstituted C1-C60 alkyl group, a substituted or unsubstituted C5-C60 aryl group, an amino group substituted with a C5-C60 aryl group, a substituted or unsubstituted C3-C60 heteroaryl group, or a substituted or unsubstituted C6-C60 condensed polycyclic group.

According to an embodiment of the present invention, a heterocyclic compound represented by Formula 4 is provided.

Formula 4

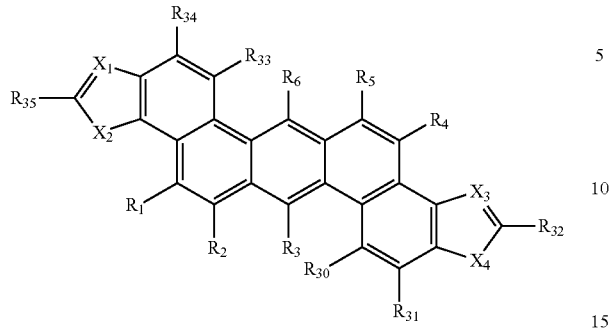

In Formula 4, $R_1$ to $R_6$ and $R_{30}$ to $R_{35}$ are each independently a lone pair electron, a hydrogen atom, a heavy hydrogen atom, a halogen atom, a cyano group, a substituted or unsubstituted C1-C50 alkyl group, a substituted or unsubstituted C5-C60 aryl group, an amino group substituted with a C5-C50 aryl group, a substituted or unsubstituted C3-C60 heteroaryl group, or a substituted or unsubstituted C6-C60 condensed polycyclic group, $X_1$ to $X_4$ are each independently —O—, —N($R_{40}$)—, —C($R_{41}R_{42}$)—, —C$R_{41}$=, or —S—, optionally, $R_{35}$ and $R_{40}$, $R_{41}$, or $R_{42}$; or $R_{32}$ and $R_{40}$, $R_{41}$, or $R_{42}$ may be connected to each other to form a ring, $R_{40}$ to $R_{42}$ are each independently a lone pair electron, a hydrogen atom, a heavy hydrogen atom, a halogen atom, a cyano group, a substituted or unsubstituted C1-C50 alkyl group, a substituted or unsubstituted C5-C60 aryl group, an amino group substituted with a C5-C50 aryl group, a substituted or unsubstituted C3-C60 heteroaryl group, or a substituted or unsubstituted C6-C60 condensed polycyclic group.

The heterocyclic compounds of Formulae 1 and 4 according to the current embodiment of the present invention may be suitable as a material for forming an EML, an ETL, or an electron injection layer (EIL) of an organic light-emitting device.

An organic light-emitting device manufactured using one of the compounds of Formulae 1 to 4 has high durability when stored or operated.

Substituents in the compounds of Formulae 2, 3, and 4 will now be described in detail.

In Formulae 2, 3, and 4, $R_1$ to $R_6$, $R_{10}$ to $R_{15}$, $R_{20}$ to $R_{25}$, and $R_{30}$ to $R_{35}$ may be each independently selected from the group consisting of a lone pair electron, a hydrogen atom, a heavy hydrogen atom, a halogen atom, a cyano group, a substituted or unsubstituted C1-C20 alkyl group, and one of Formulae 2a to 2j below.

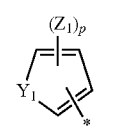
2a

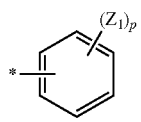
2b

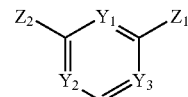
2c

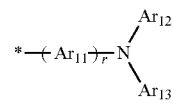
2d

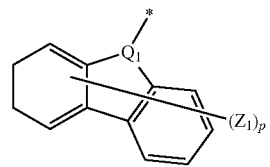
2e

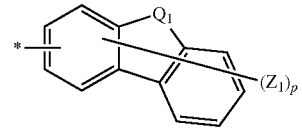
2f

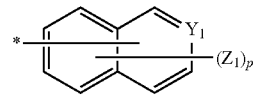
2g

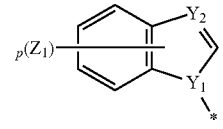
2h

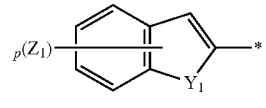
2i

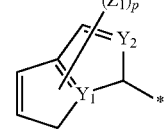
2j

In Formulae 2a to 2j, $Q_1$ is —C($R_{50}$)($R_{51}$)—, —N($R_{52}$)—, —N(-*)-, —S—, or —O—; $Y_1$, $Y_2$, and $Y_3$ are each independently —N=, —N(-*)-, —S—, —O—, or —C($R_{53}$)=; $Z_1$, $Z_2$, $Ar_{12}$, $Ar_{13}$, $R_{50}$, $R_{51}$, $R_{52}$, and $R_{53}$ are each independently selected from the group consisting of a hydrogen atom, a heavy hydrogen atom, a substituted or unsubstituted C1-C20 alkyl group, a substituted or unsubstituted C5-C20 aryl group, a substituted or unsubstituted C3-C20 heteroaryl group, a substituted or unsubstituted C6-C20 condensed polycyclic group, a halogen atom, a cyano group, a nitro group, a hydroxy group, and a carboxy group; $Ar_{11}$ is selected from the group consisting of a substituted or unsubstituted C1-C20 alkylene group, a substituted or unsubstituted C5-C20 arylene group, and a substituted or unsubstituted C3-C20 heteroarylene group; p is an integer from 1 to 10; r is an integer from 0 to 5; and * is a binding site.

In Formulae 2, 3, and 4, $R_2$, $R_3$, $R_5$, $R_6$, $R_{10}$, $R_{12}$, $R_{13}$, $R_{15}$, $R_{21}$, $R_{22}$, $R_{24}$, $R_{25}$, $R_{30}$, $R_{31}$, $R_{33}$, and $R_{34}$ may be each independently a hydrogen atom or a heavy hydrogen atom. The compounds represented by Formulae 2, 3, and 4 may be symmetrical compounds.

The symmetrical compound refers to a compound in which substituents on opposite sides with respect to the center are the same. For example, in Formula 2, $R_6$ and $R_3$ are the same, $R_1$ and $R_4$ are the same, $R_{13}$ and $R_{10}$ are the same, and $X_1$ and $X_3$ are the same.

In Formulae 2, 3, and 4, $R_2$, $R_3$, $R_5$, $R_6$, $R_{10}$, $R_{12}$, $R_{13}$, $R_{15}$, $R_{21}$, $R_{22}$, $R_{24}$, $R_{25}$, $R_{30}$, $R_{31}$, $R_{33}$, and $R_{34}$ are each independently a hydrogen atom or a heavy hydrogen atom, and $R_1$, $R_4$, $R_{11}$, $R_{14}$, $R_{20}$, $R_{23}$, $R_{32}$, and $R_{35}$ are each independently selected from the group consisting of a lone pair electron, a hydrogen atom, a heavy hydrogen atom, a halogen atom, a cyano group, a substituted or unsubstituted C1-C20 alkyl group, and one of Formulae 2a to 2j below.

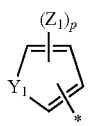
2a

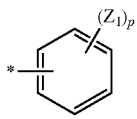
2b

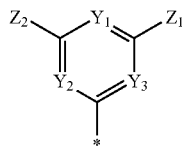
2c

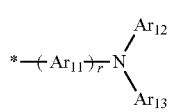
2d

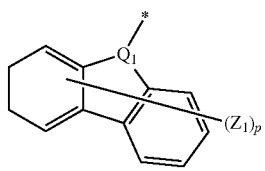
2e

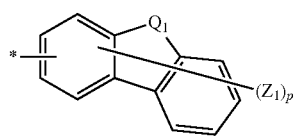
2f

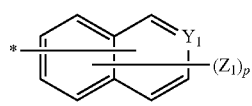
2g

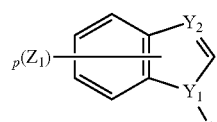
2h

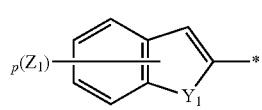
2i

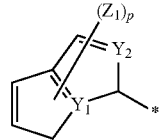
2j

In Formulae 2a to 2j, $Q_1$ is —$C(R_{50})(R_{51})$—, —$N(R_{52})$—, —N(-*)-, —S—, or —O—; $Y_1$, $Y_2$, and $Y_3$ are each independently —N=, —N(-*)-, —S—, —O—, or —$C(R_{53})$=; $Z_1$, $Z_2$, $Ar_{12}$, $Ar_{13}$, $R_{50}$, $R_{51}$, $R_{52}$, and $R_{53}$ are each independently selected from the group consisting of a hydrogen atom, a heavy hydrogen atom, a substituted or unsubstituted C1-C20 alkyl group, a substituted or unsubstituted C5-C20 aryl group, a substituted or unsubstituted C3-C20 heteroaryl group, a substituted or unsubstituted C6-C20 condensed polycyclic group, a halogen atom, a cyano group, a nitro group, a hydroxy group, and a carboxy group;

$Ar_{11}$ is selected from the group consisting of a substituted or unsubstituted C1-C20 alkylene group, a substituted or unsubstituted C5-C20 arylene group, and a substituted or unsubstituted C3-C20 heteroarylene group;

p is an integer from 1 to 10;

r is an integer from 0 to 5; and

* is a binding site.

In Formulae 2, 3, and 4, $R_2$, $R_3$, $R_5$, $R_6$, $R_{10}$, $R_{12}$, $R_{13}$, $R_{15}$, $R_{21}$, $R_{22}$, $R_{24}$, $R_{25}$, $R_{30}$, $R_{31}$, $R_{33}$, and $R_{34}$ may be each independently a hydrogen atom or a heavy hydrogen atom, and $R_1$, $R_4$, $R_{11}$, $R_{14}$, $R_{20}$, $R_{23}$, $R_{32}$, and $R_{35}$ may be each independently selected from the group consisting of a lone pair electron, a hydrogen atom, a heavy hydrogen atom, a halogen atom, a cyano group, a substituted or unsubstituted C1-C20 alkyl group, and one of Formulae 2a to 2j below.

The compounds represented by Formulae 2, 3, and 4 may be symmetrical compounds.

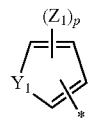
2a

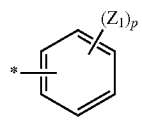
2b

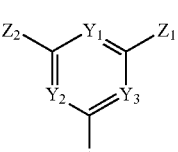
2c

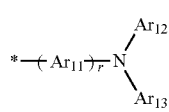
2d

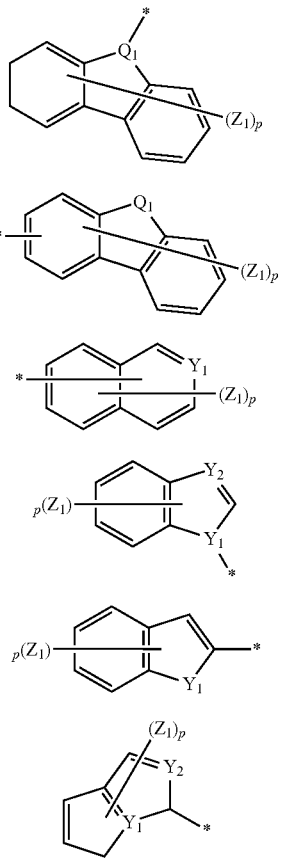

In Formulae 2a to 2j, $Q_1$ is —$C(R_{50})(R_{51})$—, —$N(R_{52})$—, —N(-*)-, —S—, or —O—; $Y_1$, $Y_2$, and $Y_3$ are each independently —N═, —N(-*)-, —S—, —O—, or —$C(R_{53})$═; $Z_1$, $Z_2$, $Ar_{12}$, $Ar_{13}$, $R_{50}$, $R_{51}$, $R_{52}$, and $R_{53}$ are each independently selected from the group consisting of a hydrogen atom, a heavy hydrogen atom, a substituted or unsubstituted C1-C20 alkyl group, a substituted or unsubstituted C5-C20 aryl group, a substituted or unsubstituted C3-C20 heteroaryl group, a substituted or unsubstituted C6-C20 condensed polycyclic group, a halogen atom, a cyano group, a nitro group, a hydroxy group, and a carboxy group;

$Ar_{11}$ is selected from the group consisting of a substituted or unsubstituted C1-C20 alkylene group, a substituted or unsubstituted C5-C20 arylene group, and a substituted or unsubstituted C3-C20 heteroarylene group;

p is an integer from 1 to 10;

r is an integer from 0 to 5; and

* is a binding site.

Hereinafter, substituents described with reference to Formulae 1 to 4 will now be described in detail. In this regard, the numbers of carbon atoms in substituents are presented only for illustrative purposes and do not limit the characteristics of the substituents.

The unsubstituted C1-C60 alkyl group used herein may be linear or branched. Examples of the alkyl group may include, but are not limited to, methyl, ethyl, propyl, isobutyl, sec-butyl, pentyl, iso-amyl, hexyl, heptyl, octyl, nonanyl, and dodecyl. At least one hydrogen atom of the alkyl group may be substituted with a heavy hydrogen atom, a halogen atom, a hydroxyl group, a nitro group, a cyano group, an amino group, an amidino group, hydrazine, hydrazone, a carboxyl group or a salt thereof, a sulfonic acid group or a salt thereof, a phosphoric acid group or a salt thereof, a C1-C10 alkyl group, a C1-C10 alkoxy group, a C2-C10 alkenyl group, a C2-C10 alkynyl group, a C6-C16 aryl group, or a C4-C16 heteroaryl group.

The unsubstituted C2-C60 alkenyl group used herein refers to a hydrocarbon chain having at least one carbon-carbon double bond within or at a terminal of the unsubstituted alkyl group. Examples of the C2-C60 alkenyl group include ethenyl, propenyl, and butenyl. At least one hydrogen atom of the alkenyl group may be substituted with the same substituent groups as described above in connection with the alkyl group.

The unsubstituted C2-C60 alkynyl group used herein refers to a hydrocarbon chain having at least one carbon-carbon triple bond within or at a terminal of the alkyl group. Examples of the unsubstituted C2-C60 alkynyl group include acetylene, propylene, phenylacetylene, naphthylacetylene, isopropylacetylene, t-butylacetylene, and diphenylacetylene. At least one hydrogen atom of the alkynyl group may be substituted with the same substituent groups as described above in connection with the alkyl group.

The unsubstituted C3-C60 cycloalkyl group used herein refers to a C3-C60 cyclic alkyl group wherein at least one hydrogen atom in the cycloalkyl group may be substituted with the same substituent group described above in connection with the C1-C60 alkyl group.

The unsubstituted C1-C60 alkoxy group used herein is a group having a structure of —OA wherein A is an unsubstituted C1-C60 alkyl group as described above. Examples of the C1-C60 alkoxy group include methoxy, ethoxy, propoxy, isopropyloxy, butoxy, and pentoxy. At least one hydrogen atom of the alkoxy group may be substituted with the same substituent groups as described above in connection with the alkyl group.

The unsubstituted C5-C60 aryl group used herein refers to a carbocyclic aromatic system containing at least one ring. At least two rings may be fused to each other or linked to each other by a single bond. The term 'aryl' refers to an aromatic system, such as phenyl, naphthyl, or anthracenyl. At least one hydrogen atom in the aryl group may be substituted with the same substituent groups described with reference to the C1-C60 alkyl group.

Examples of the substituted or unsubstituted C5-C60 aryl group include a phenyl group, a C1-C10 alkylphenyl group (for example, ethylphenyl group), a halophenyl group (for example, o-, m-, and p-fluorophenyl group, and dichlorophenyl group), a cyanophenyl group, a dicyanophenyl group, a trifluoromethoxyphenyl group, a biphenyl group, a halobiphenyl group, a cyanobiphenyl group, a C1-C10 alkyl biphenyl group, a C1-C10 alkoxybiphenyl group, an o-, m-, and p-toryl group, an o-, m-, and p-cumenyl group, a mesityl group, a phenoxyphenyl group, an (α,α-dimethylbenzene) phenyl group, an (N,N'-dimethyl)aminophenyl group, an (N,N'-diphenyl)aminophenyl group, a pentalenyl group, an indenyl group, a naphthyl group, a halonaphthyl group (for example, fluoronaphthyl group), a $C_1$-$C_{10}$ alkylnaphthyl group (for example, methylnaphthyl group), a $C_1$-$C_{10}$ alkoxynaphthyl group (for example, methoxynaphthyl group), a cyanonaphthyl group, an anthracenyl group, an azulenyl group, a heptalenyl group, an acenaphthylenyl group, a phenalenyl group, a fluorenyl group, an anthraquinolyl group, a methylanthryl group, a phenanthryl group, a triphenylene group, a pyrenyl group, a chrycenyl group, an ethyl-chrysenyl group, a picenyl group, a perylenyl group, a chloroperylenyl group, a pentaphenyl group, a pentacenyl group, a tetraphenylenyl group, a hexaphenyl group, a hexacenyl group, a rubicenyl group, a coronelyl group, a trinaphthylenyl group, a heptaphenyl group, a heptacenyl group, a pyranthrenyl group, and an ovalenyl group.

The unsubstituted C3-C60 heteroaryl group used herein includes one, two or three hetero atoms selected from the group consisting of N, O, P and S. At least two rings may be fused to each other or linked to each other by a single bond. Examples of the unsubstituted C4-C60 heteroaryl group include a pyrazolyl group, an imidazolyl group, an oxazolyl group, a thiazolyl group, a triazolyl group, a tetrazolyl group, an oxadiazolyl group, a pyridinyl group, a pyridazinyl group, a pyrimidinyl group, a triazinyl group, a carbazolyl group, an indolyl group, a quinolinyl group, an isoquinolinyl group, and a dibenzothiophene group. In addition, at least one hydrogen atom in the heteroaryl group may be substituted with the same substituent groups described above with reference to the C1-C60 alkyl group.

The unsubstituted C5-C60 aryloxy group used herein refers to a group represented by —$OA_1$, wherein $A_1$ is a C5-C60 aryl group. Examples of the aryloxy group include a phenoxy group. At least one hydrogen atom in the aryloxy group may be substituted with the same substituent groups described with reference to the C1-C60 alkyl group.

The unsubstituted C5-C60 arylthio group used herein refers to a group represented by —$SA_1$, wherein $A_1$ is a C5-C60 aryl group. Examples of the arylthio group include a benzenethio group and a naphthylthio group. At least one hydrogen atom in the arylthio group may be substituted with the substituent groups described with reference to the C1-C60 alkyl group.

The unsubstituted C6-C60 condensed polycyclic group is a substituent including at least two rings wherein at least one aromatic ring and/or at least one non-aromatic ring are fused to each other. The condensed polycyclic group is distinguished from the aryl group or heteroaryl group since the condensed polycyclic group does not have an aromaticity.

Examples of the heterocyclic compound according to the current embodiment may include Compounds 1A to 14Gb shown in the following Tables 1 and 2. However, the heterocyclic compound according to the current embodiment is not limited thereto.

The heterocyclic compound according to an embodiment of the present invention may be prepared by using known Sonogashira coupling, Suzuki coupling, and cyclization. The method of preparing the heterocyclic compound will be described in more detail with reference to the synthesis examples below.

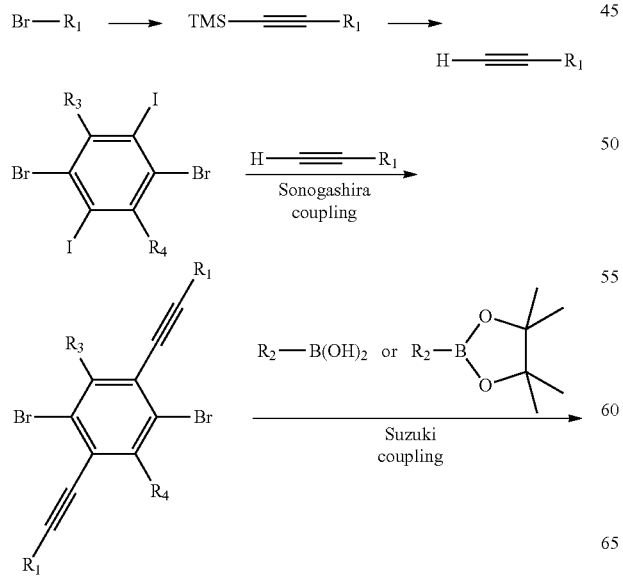

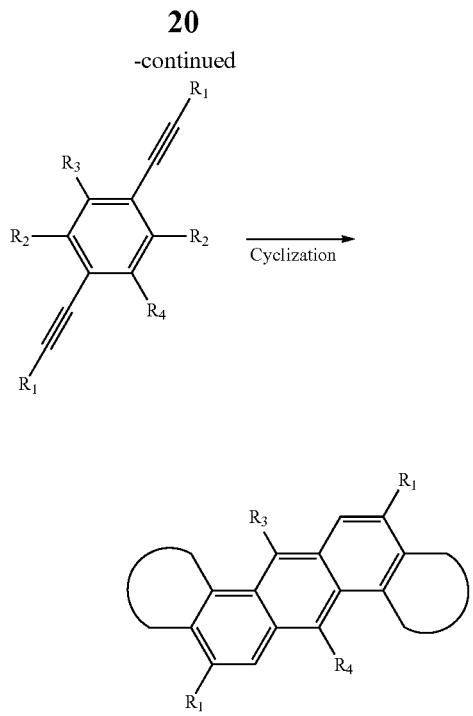

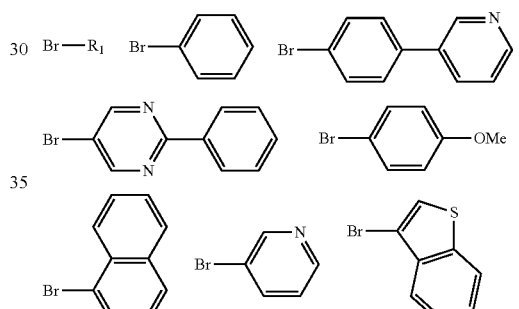

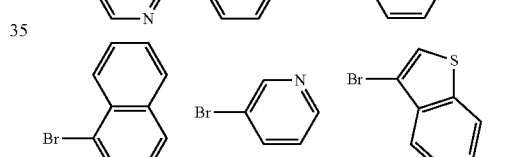

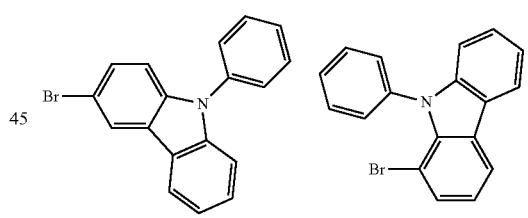

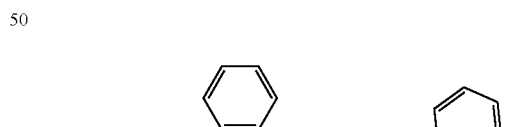

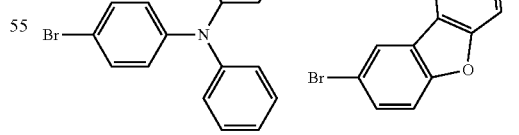

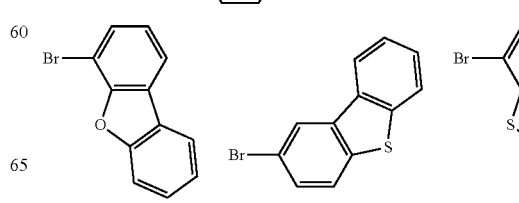

-continued
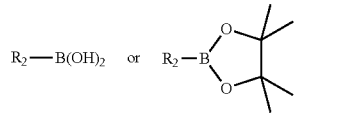
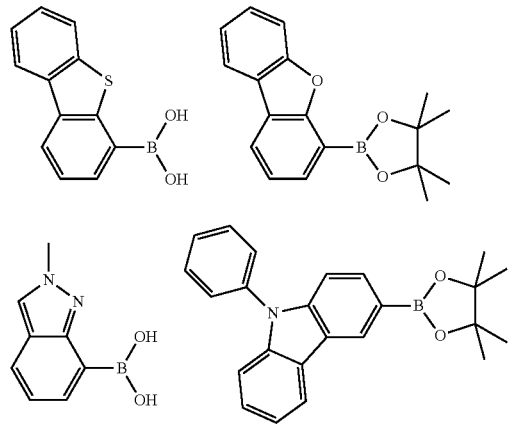
-continued
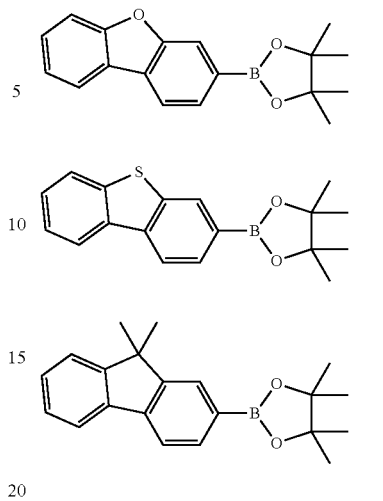

TABLE 1
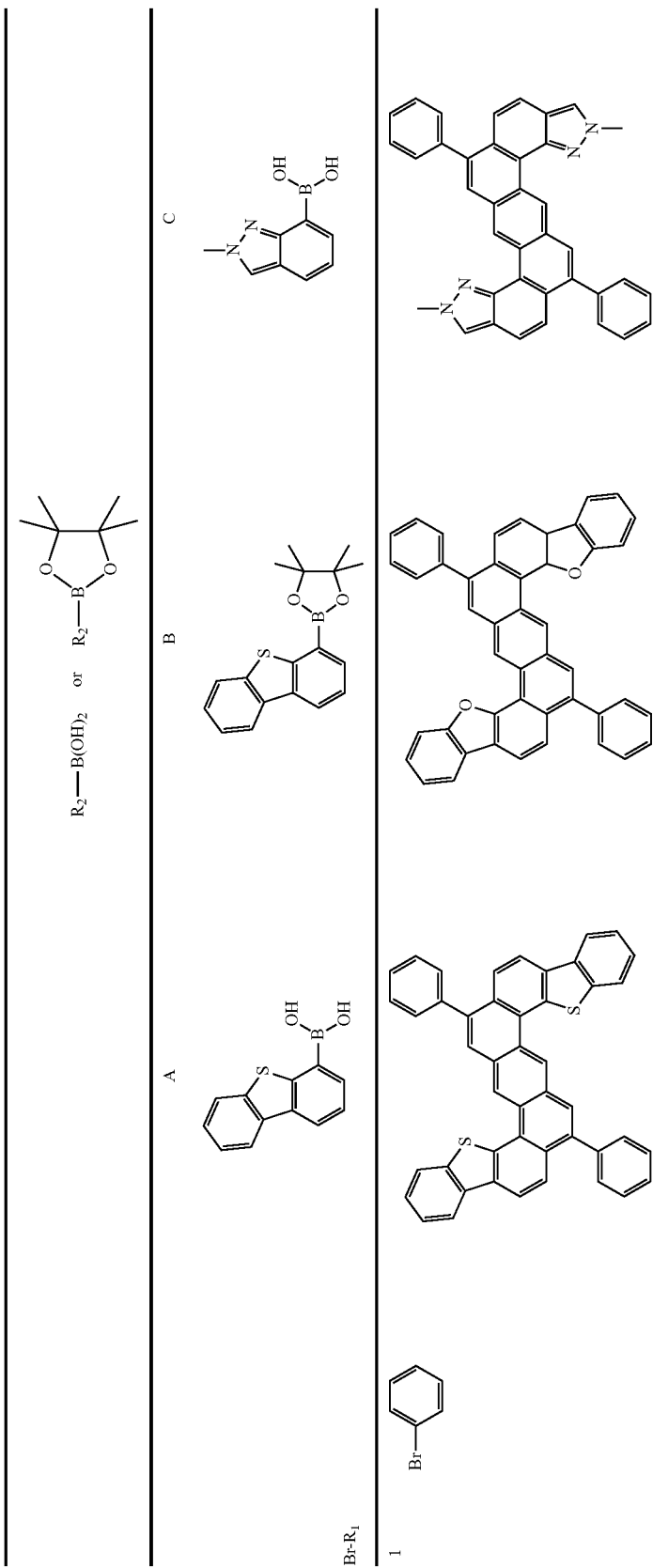

TABLE 1-continued
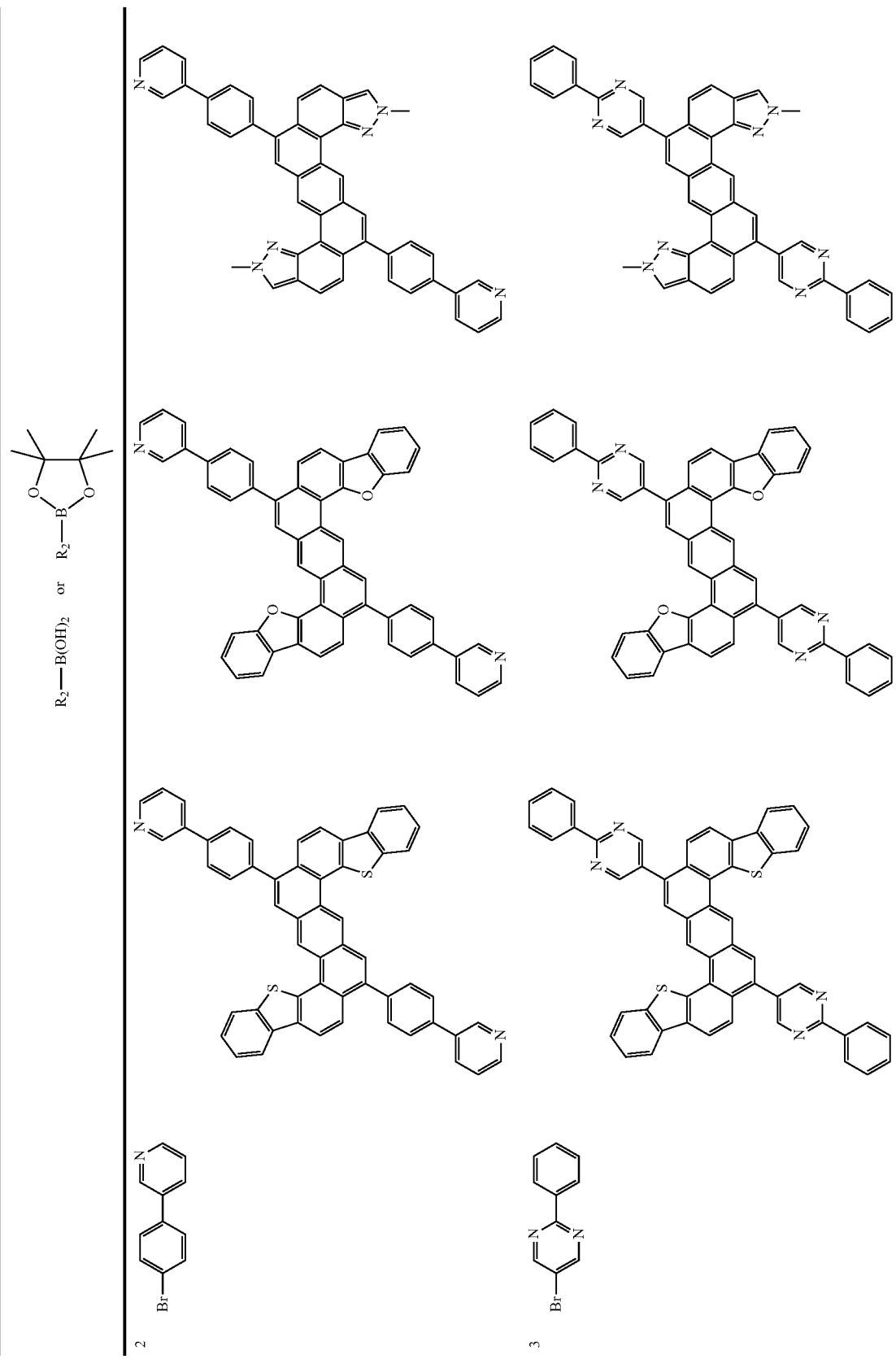

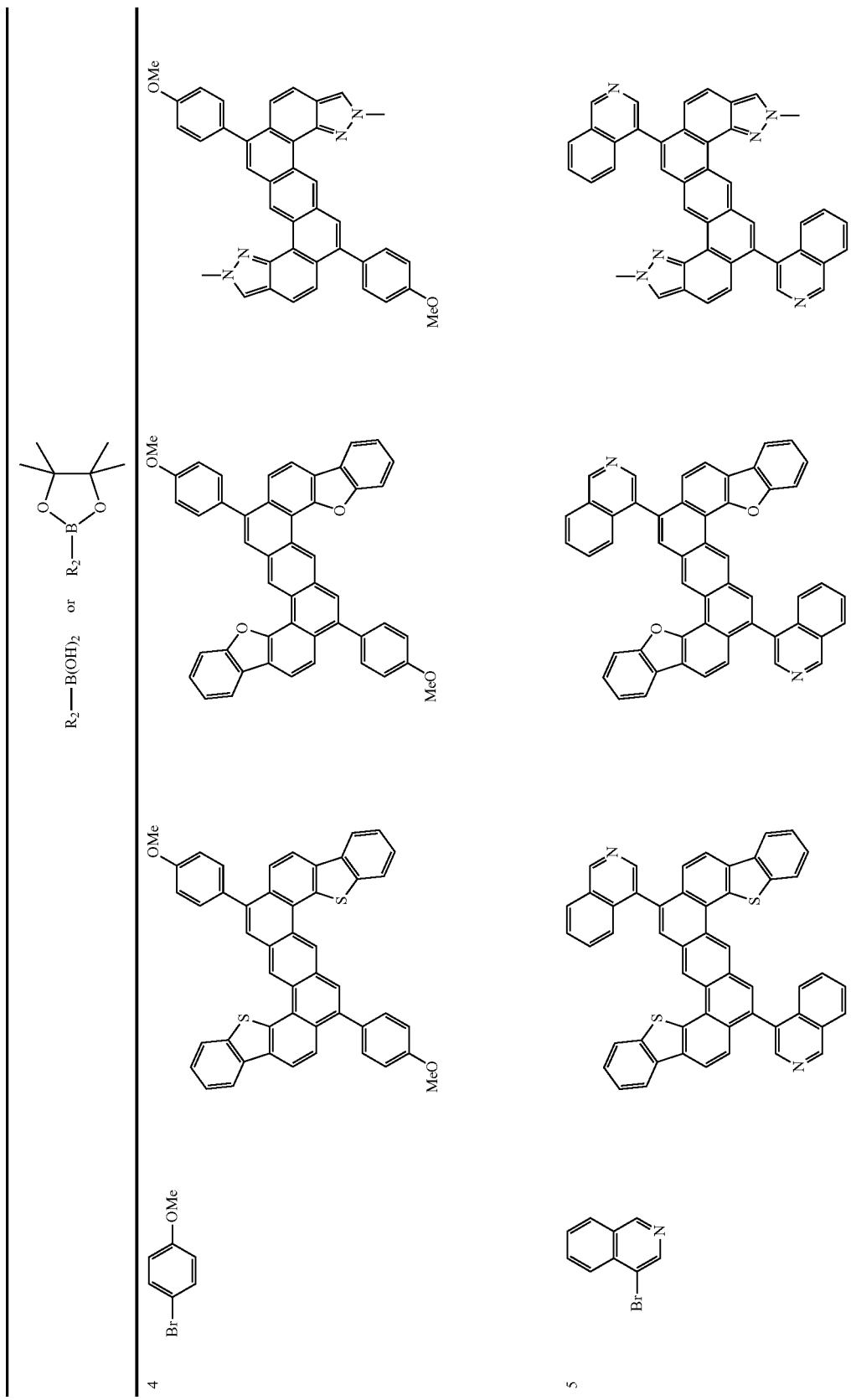

TABLE 1-continued
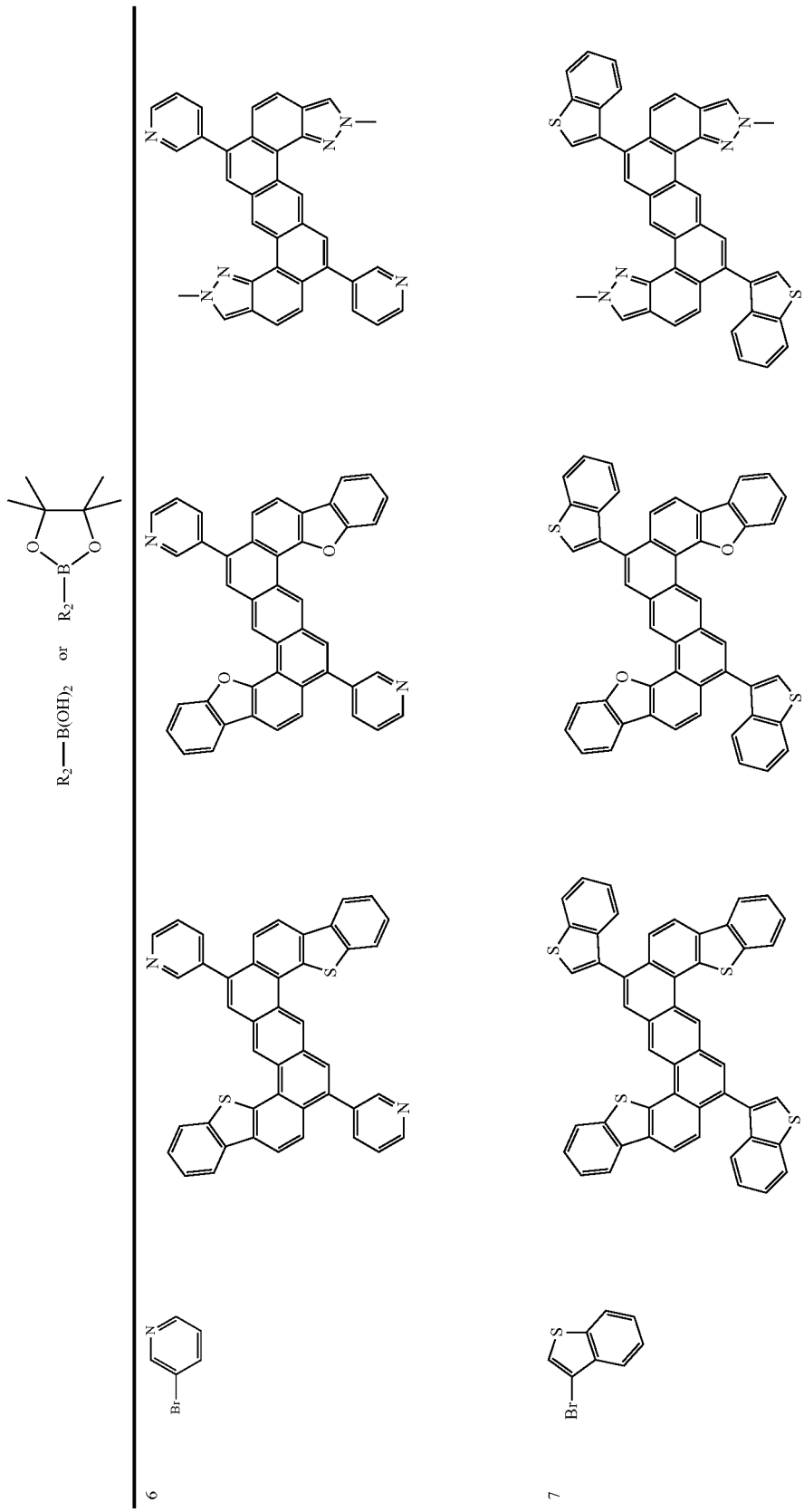

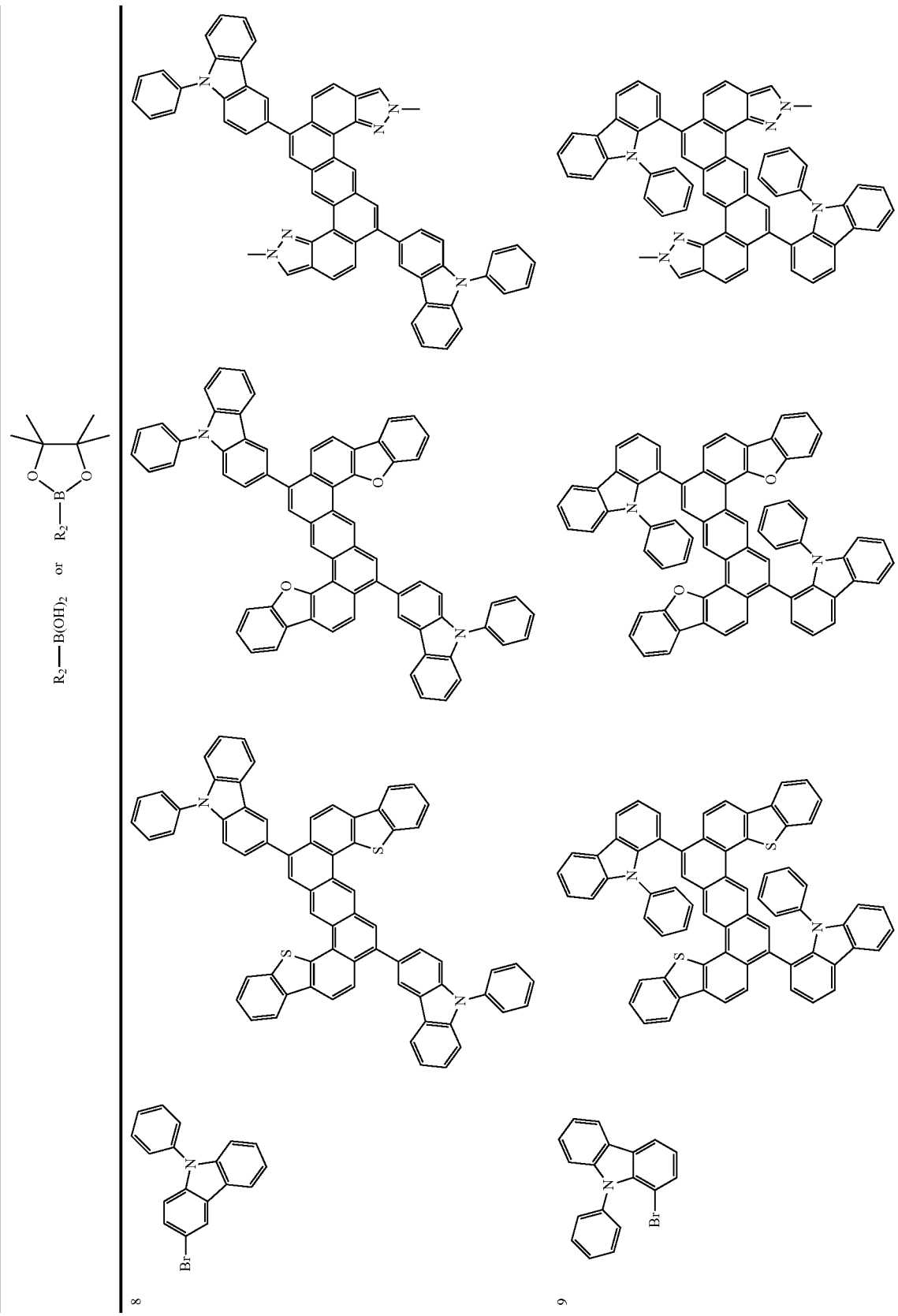

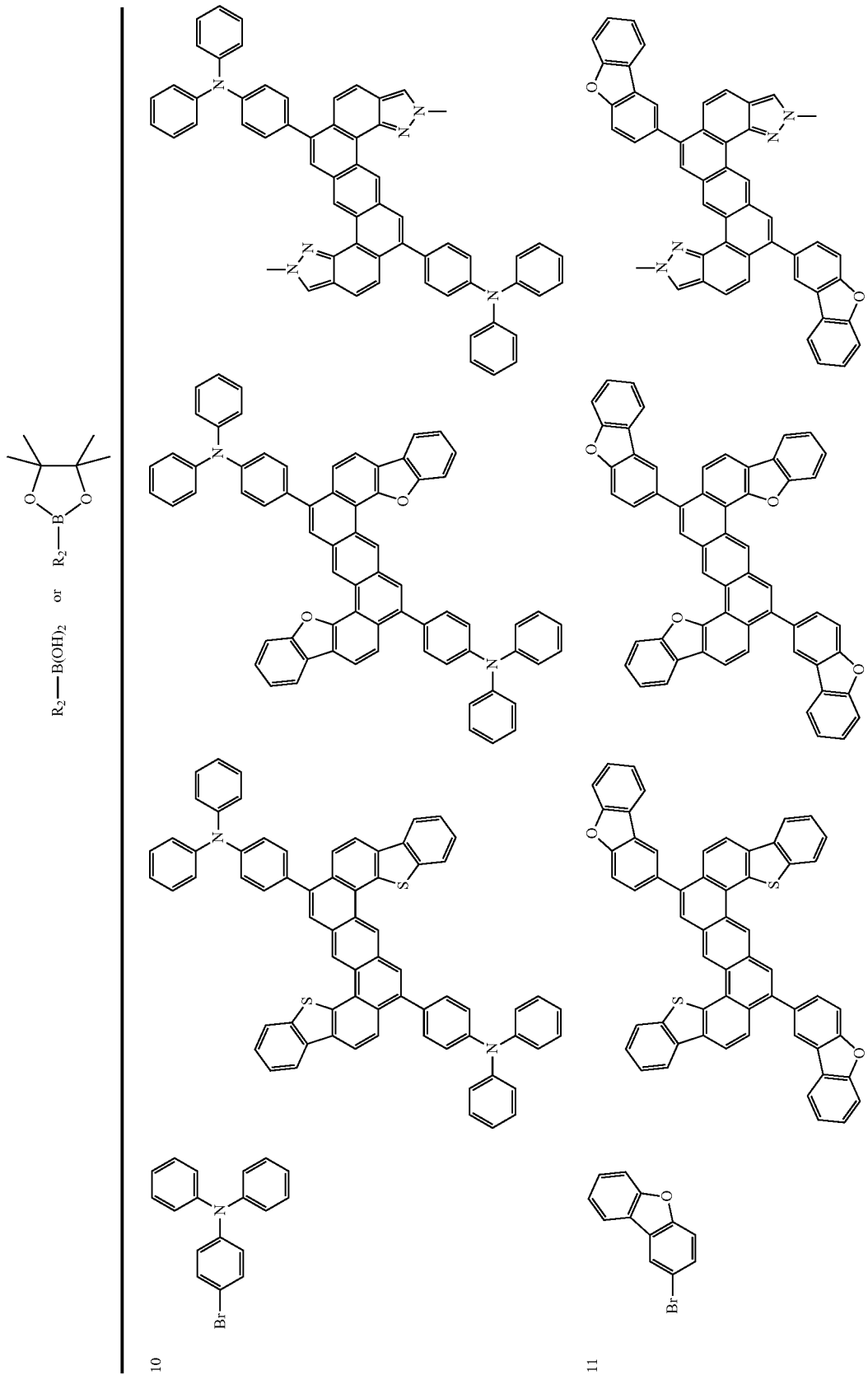

TABLE 1-continued
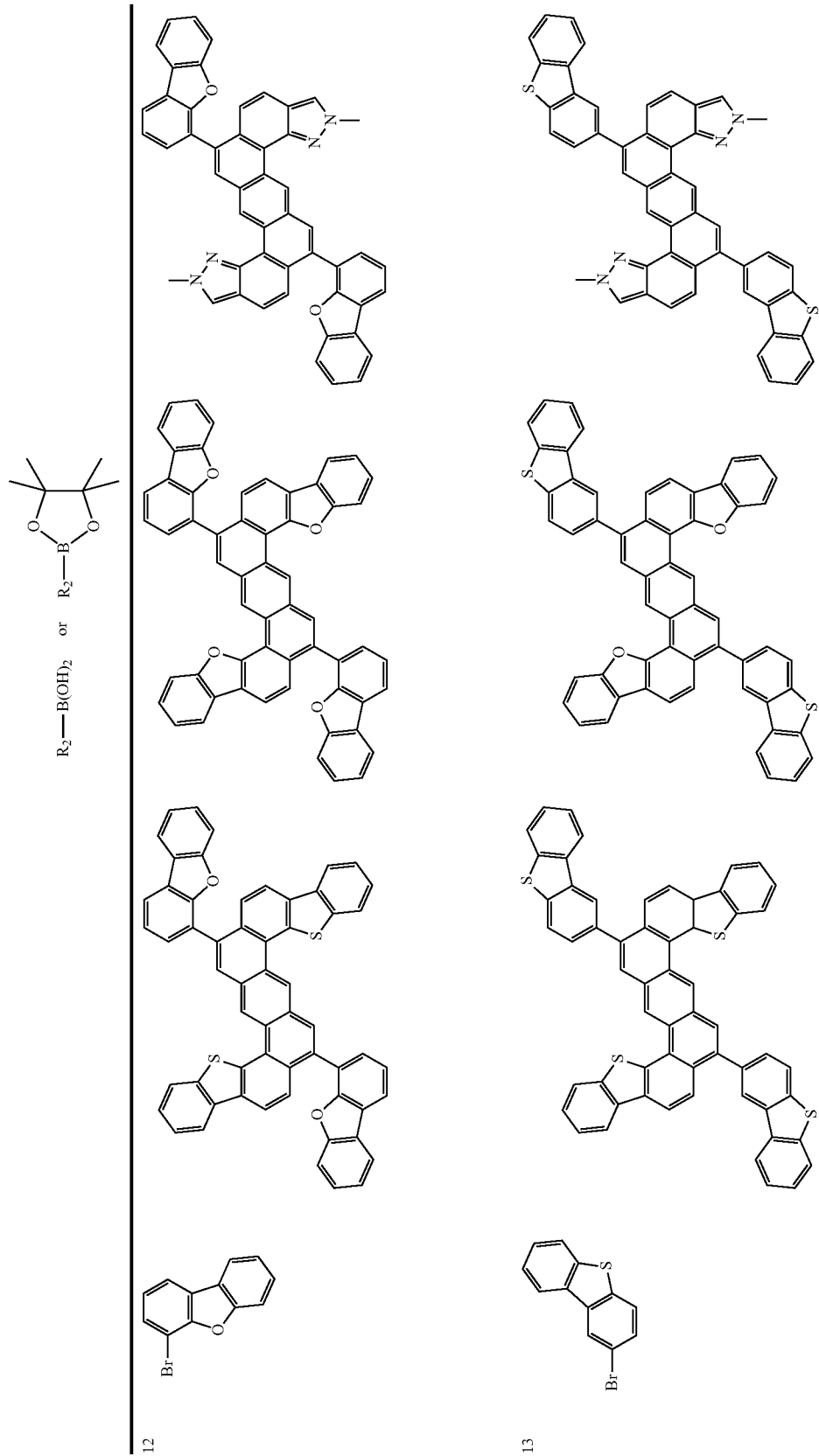

TABLE 1-continued
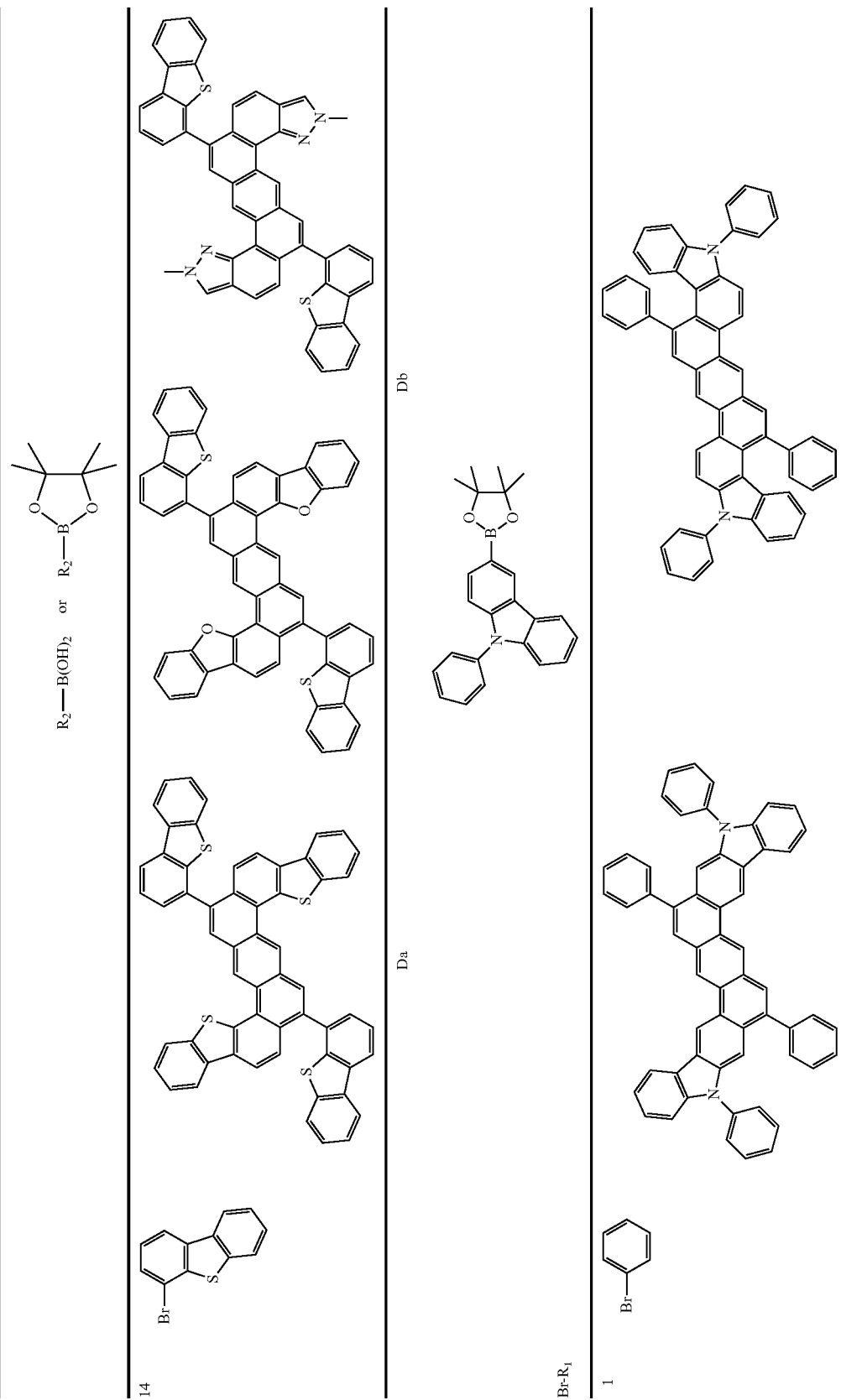

TABLE 1-continued
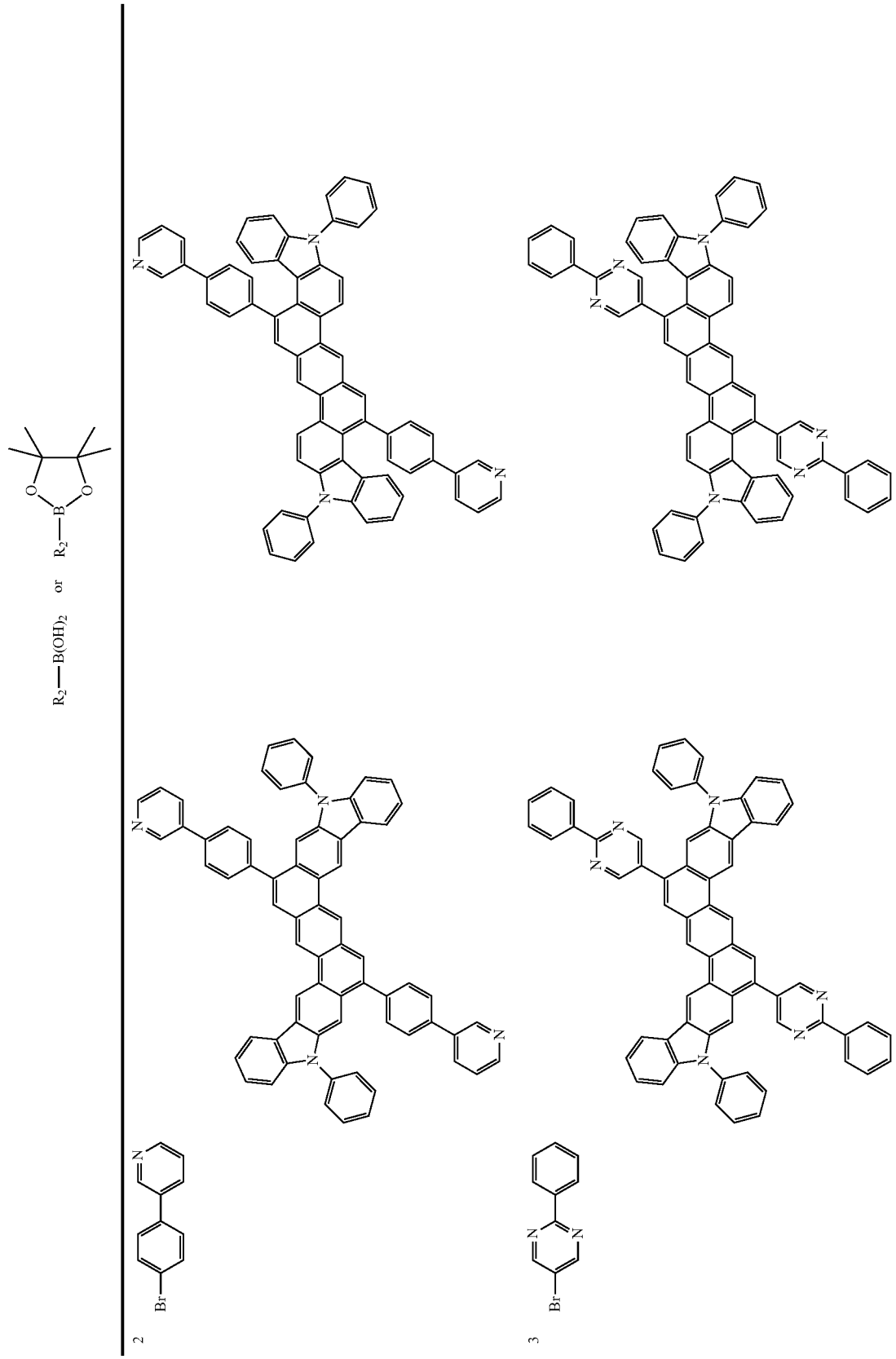

TABLE 1-continued
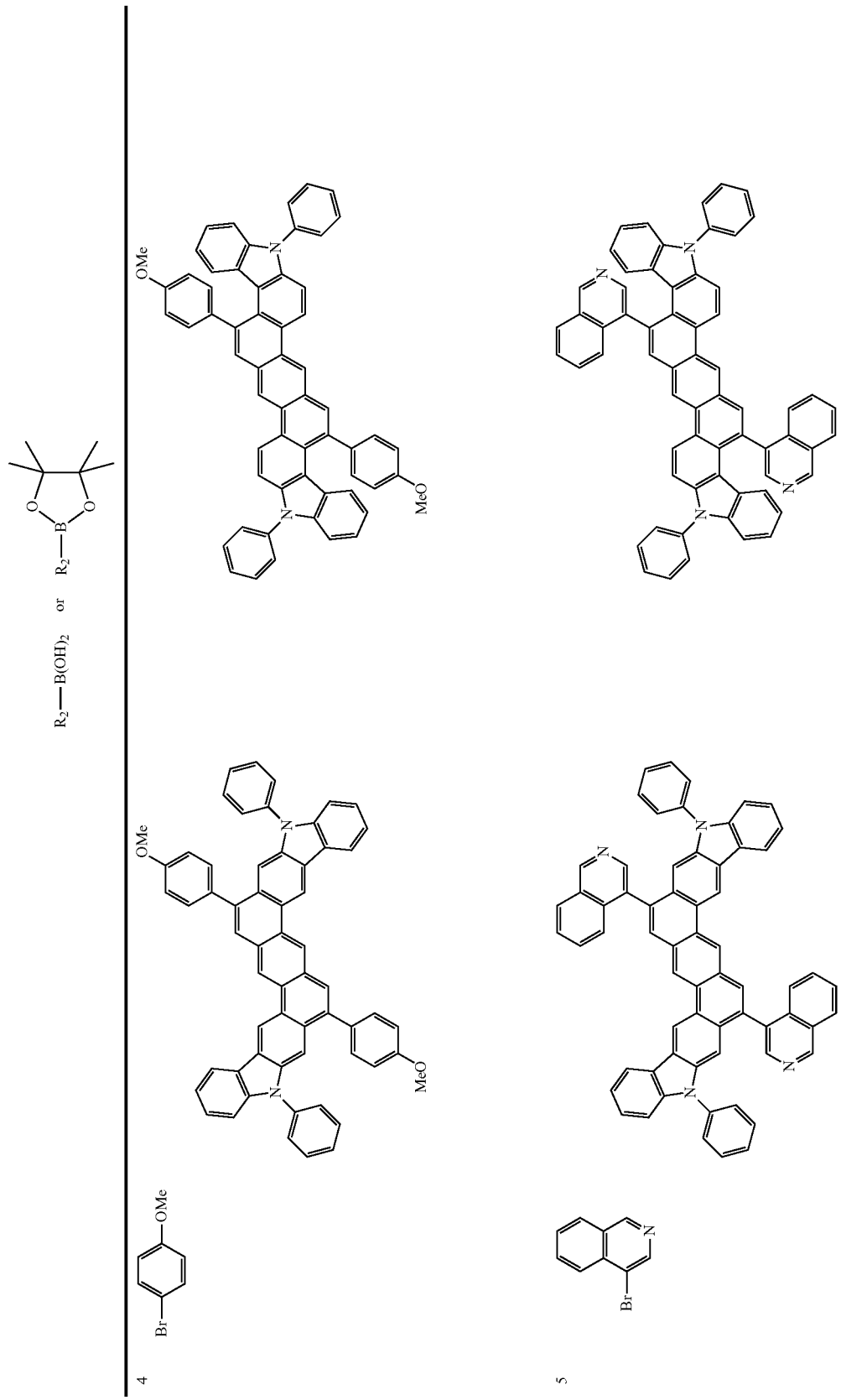

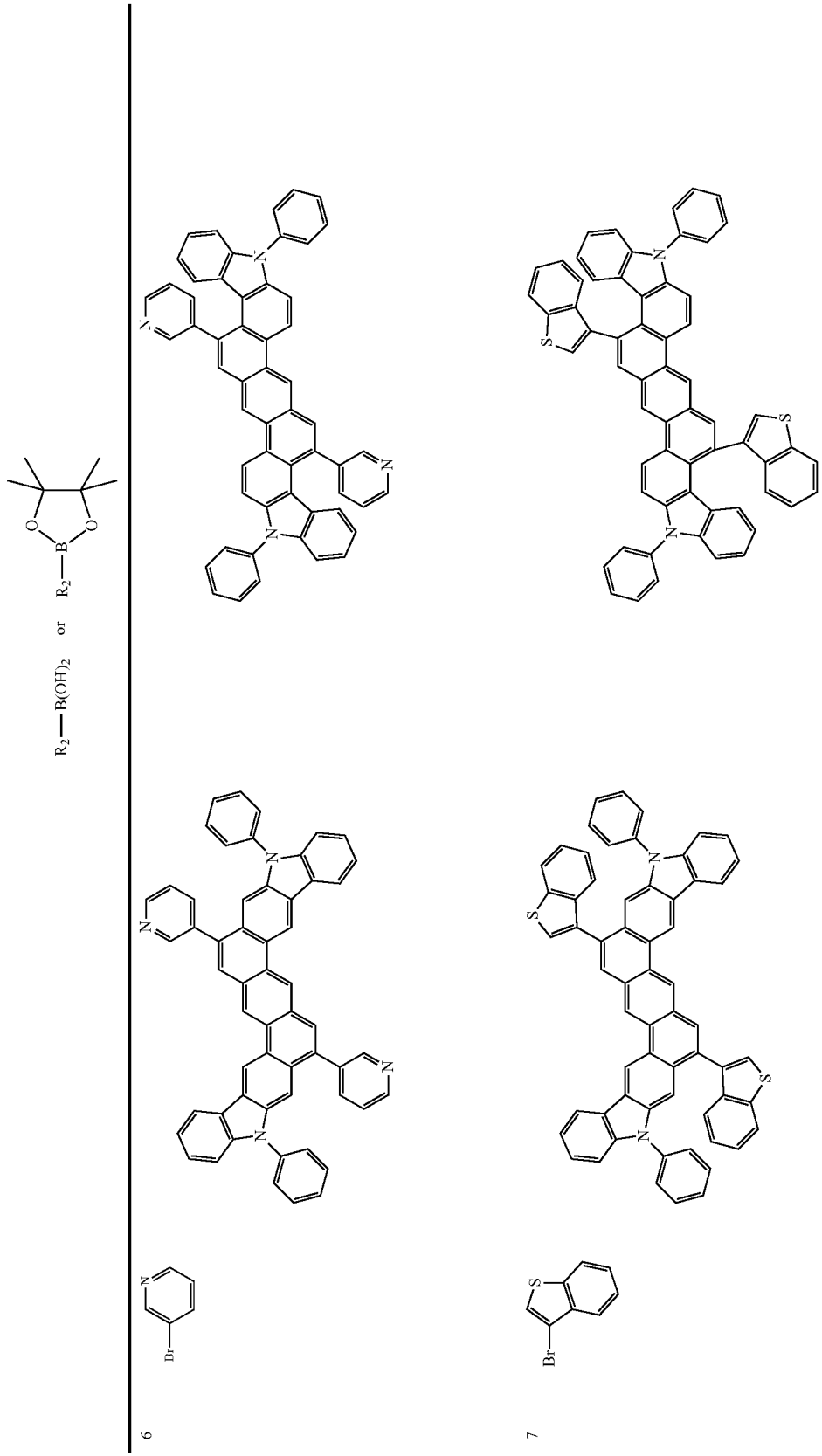

TABLE 1-continued
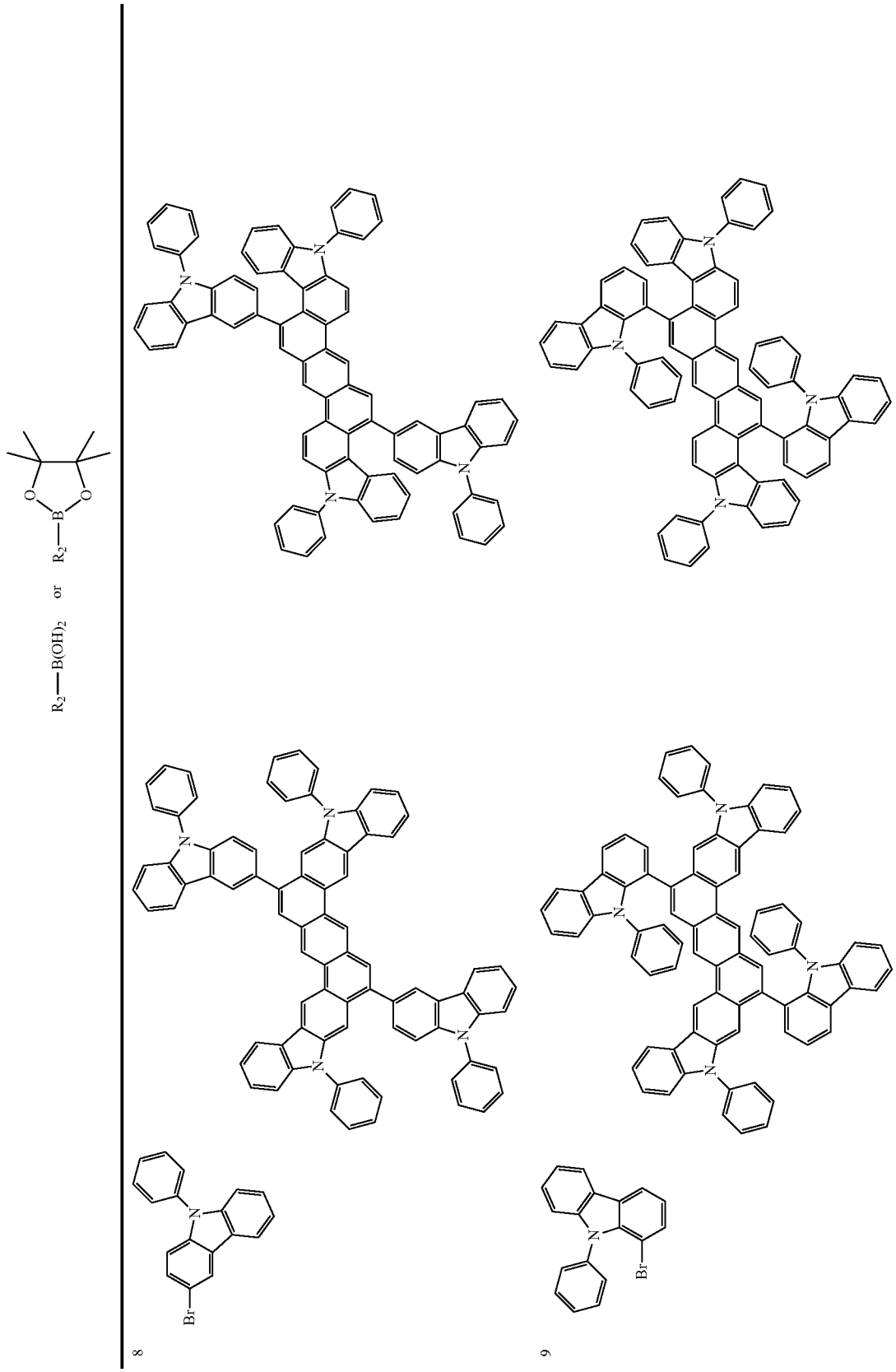

TABLE 1-continued
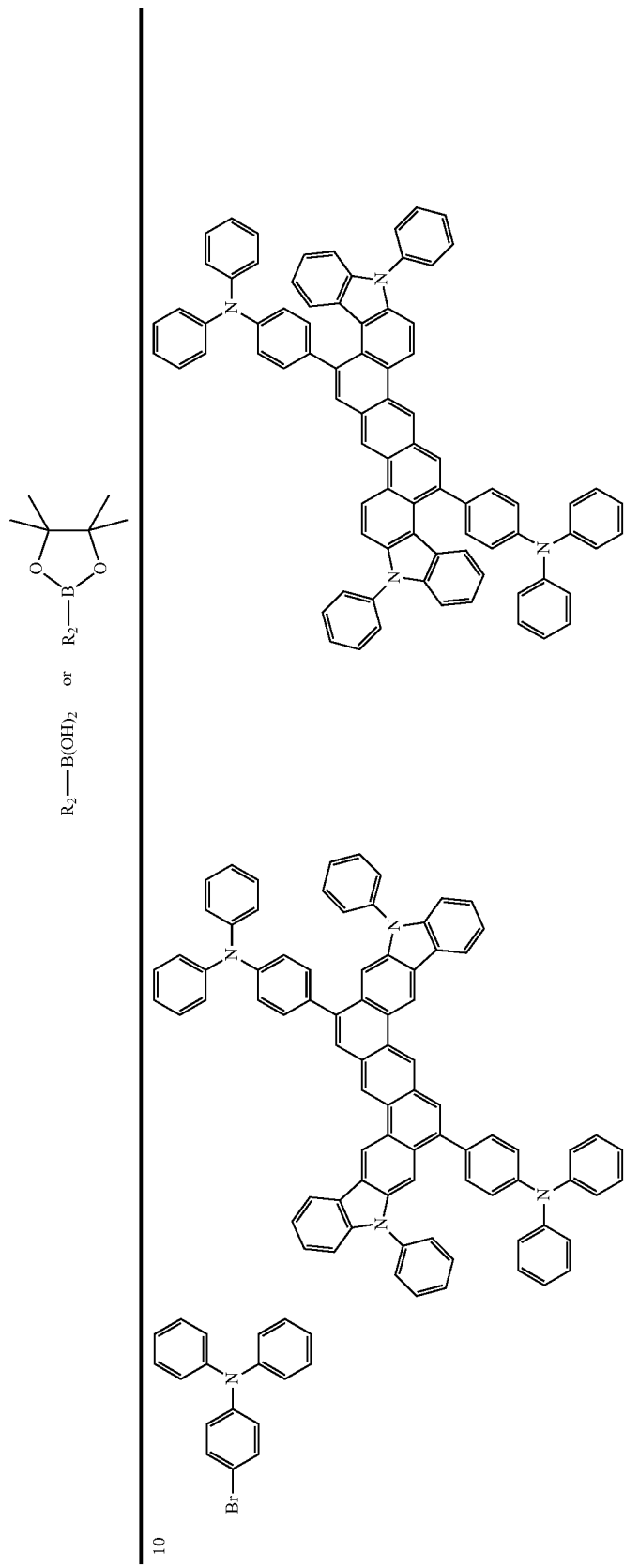

TABLE 1-continued
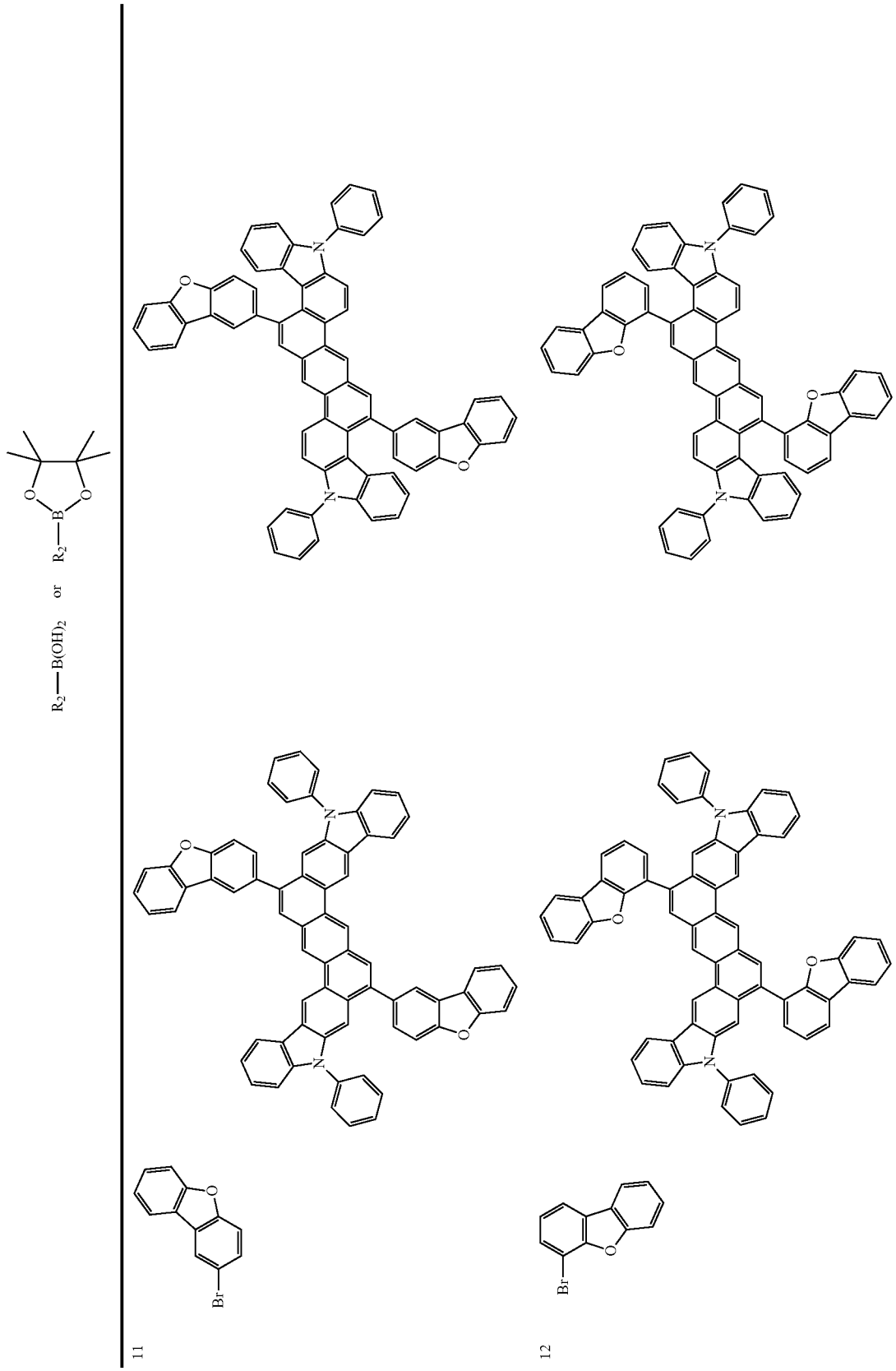

TABLE 1-continued
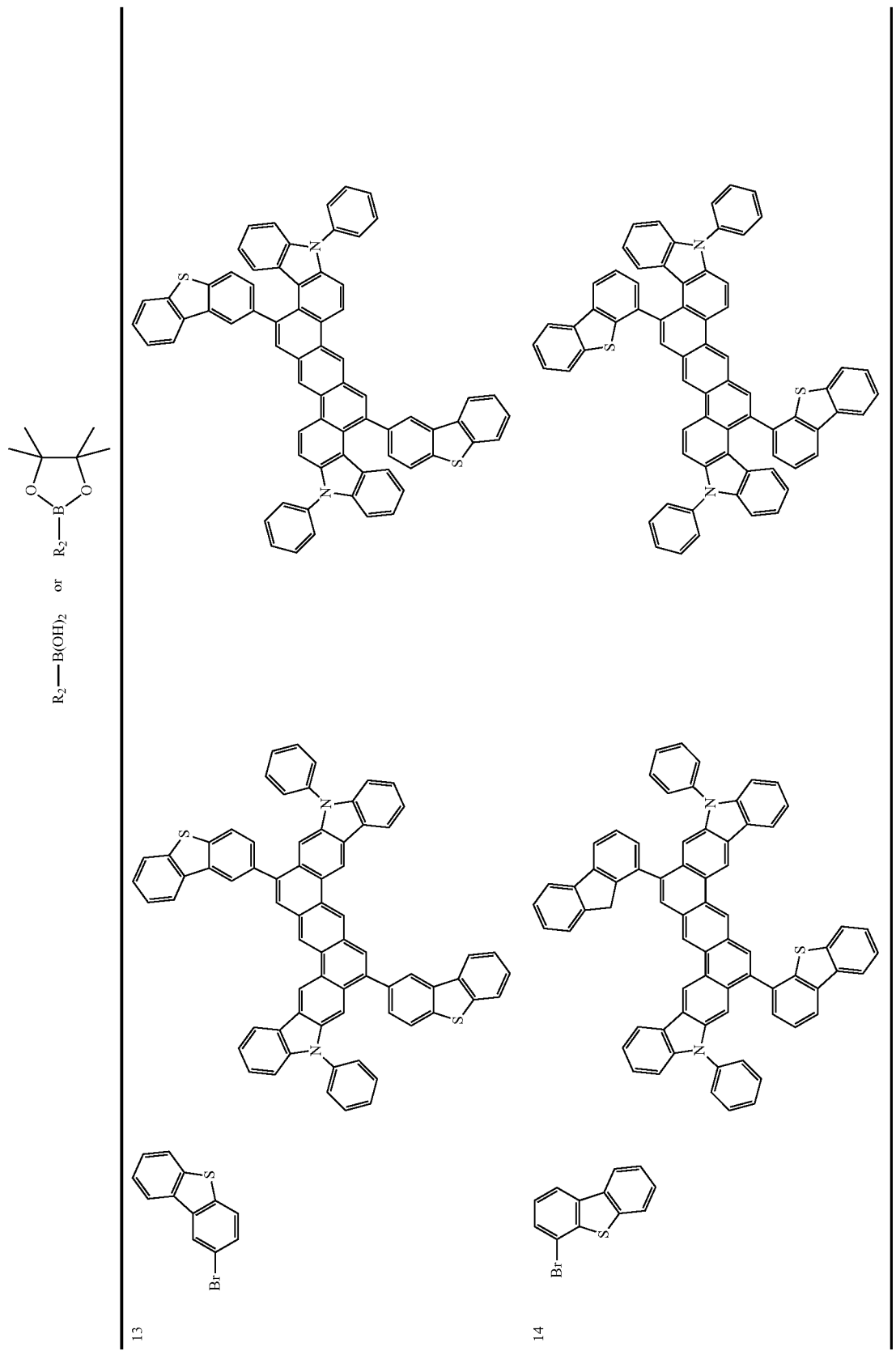

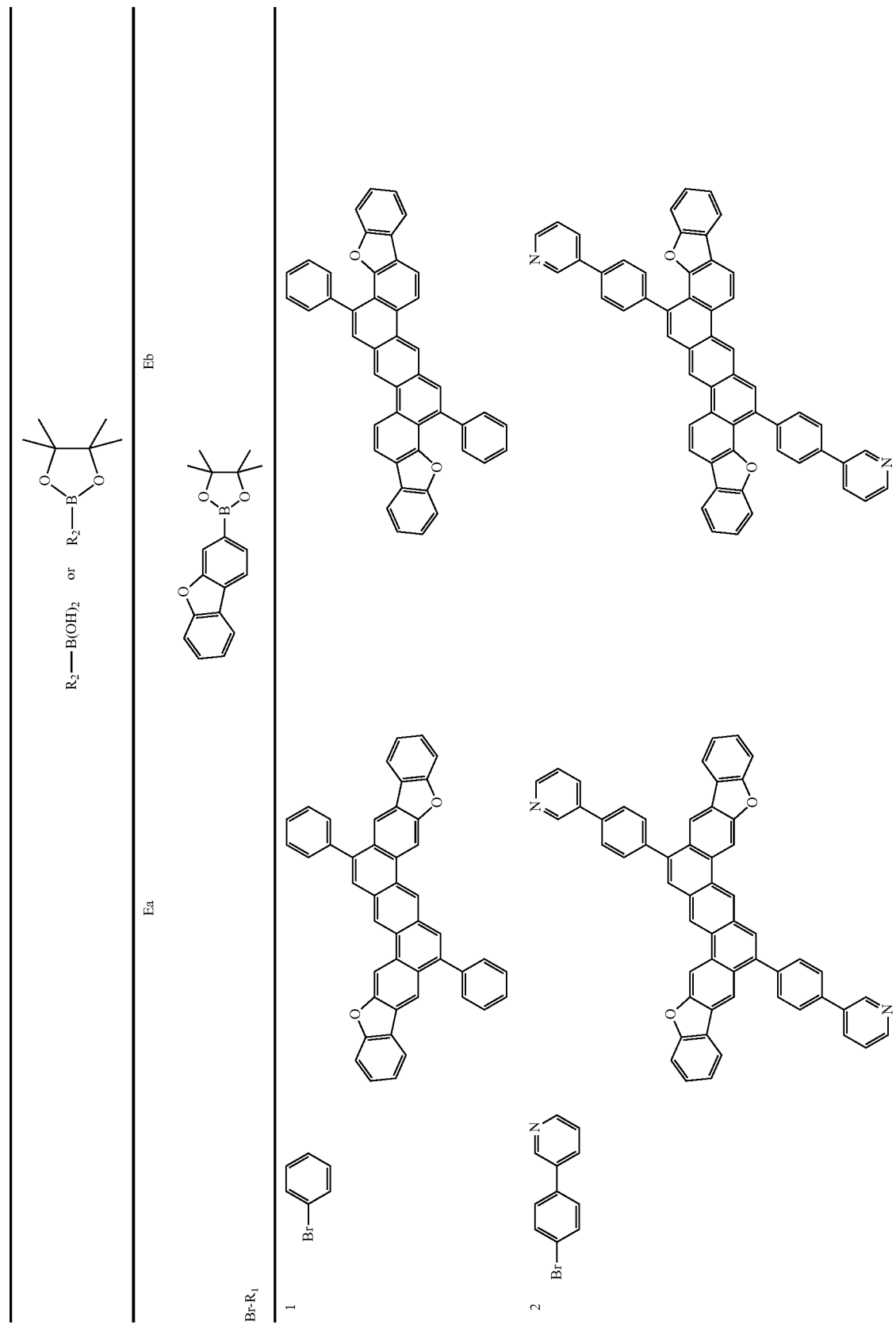

TABLE 1-continued
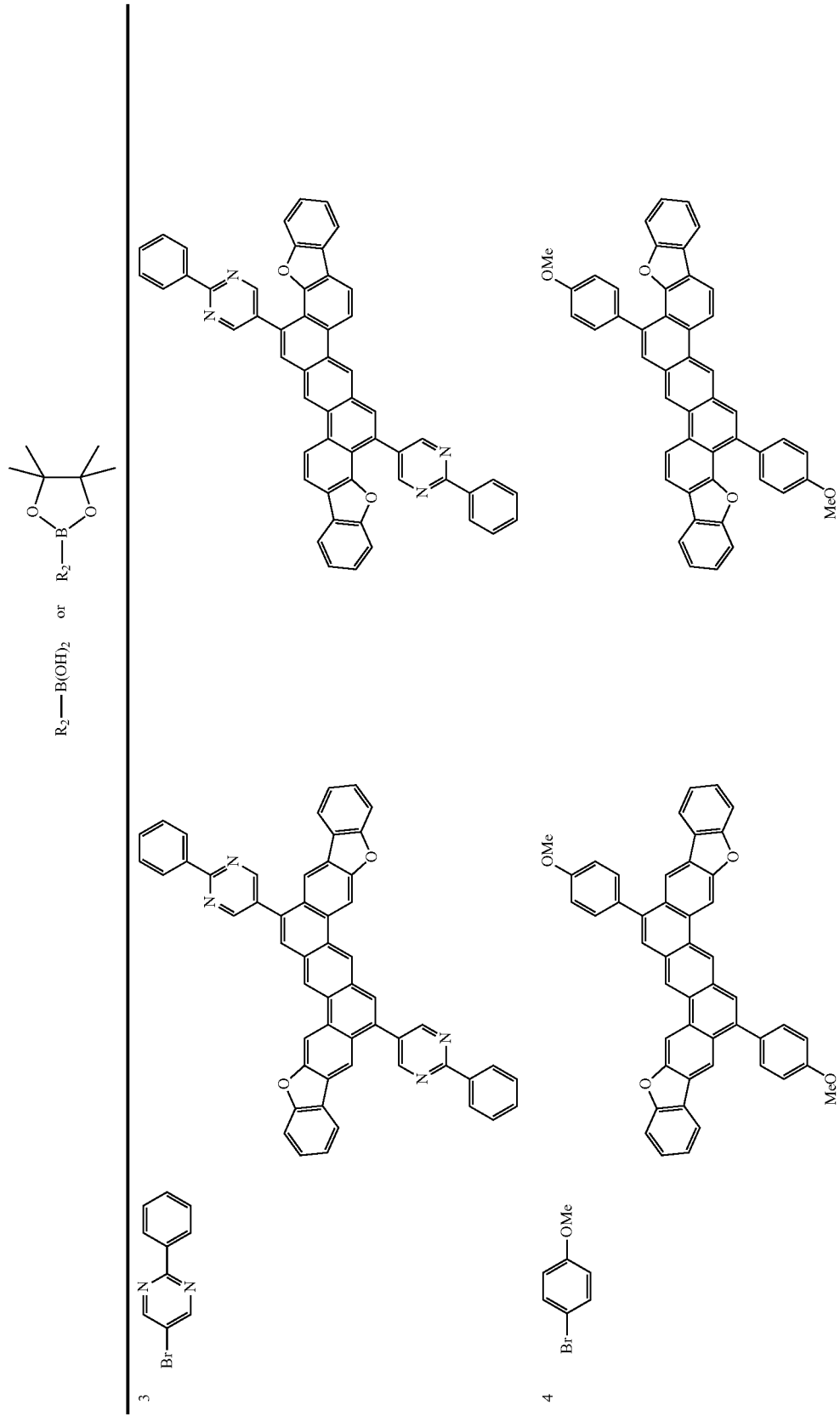

TABLE 1-continued
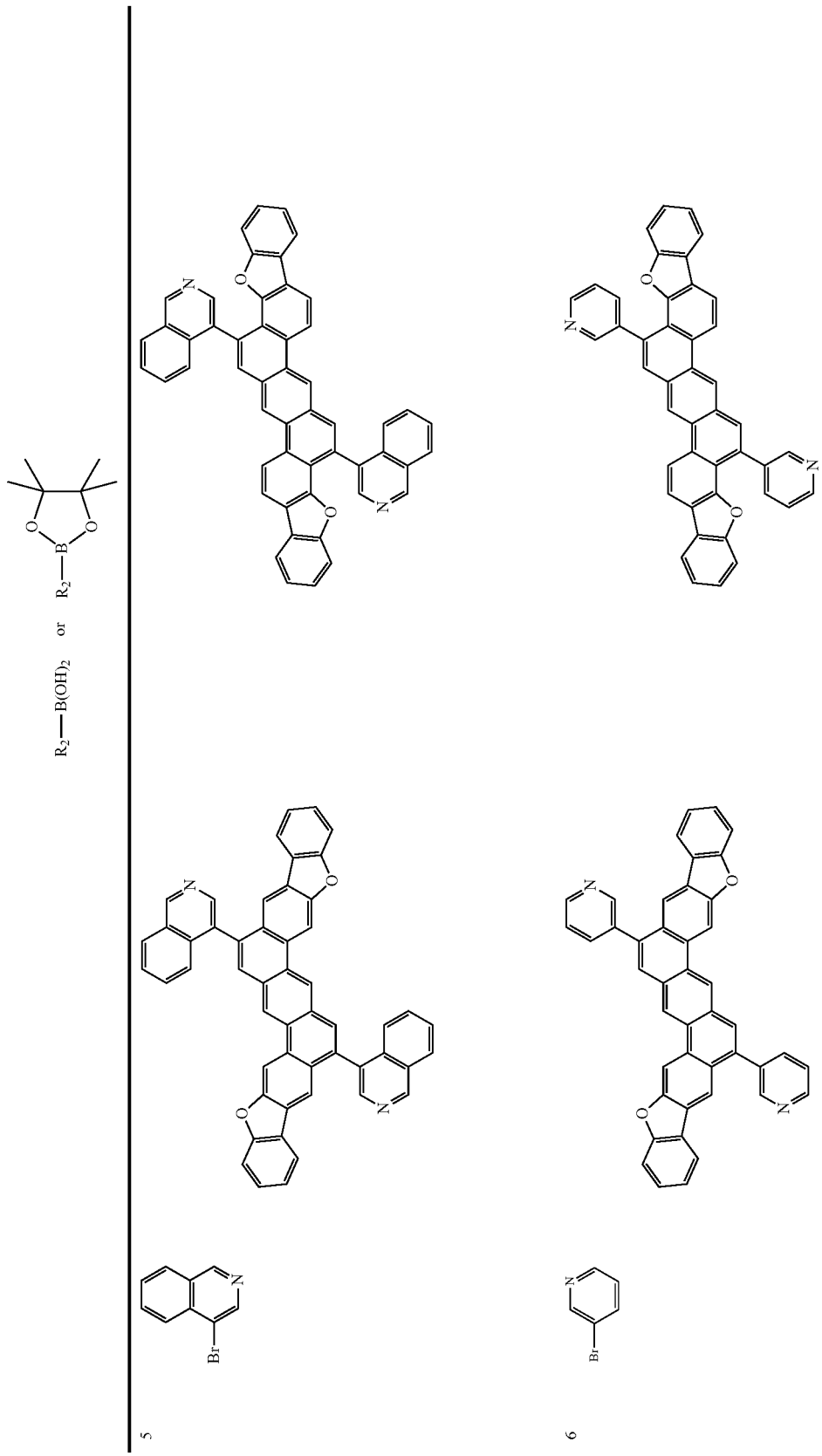

TABLE 1-continued
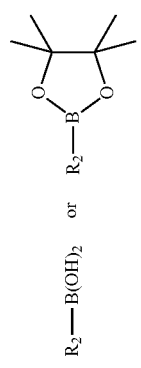
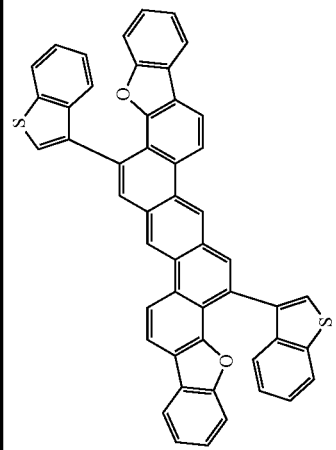
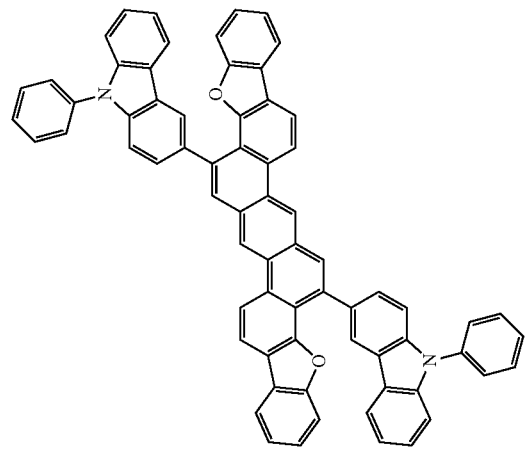
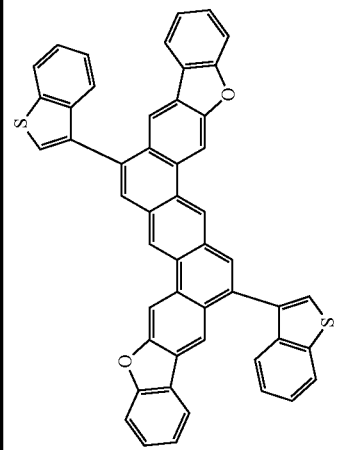
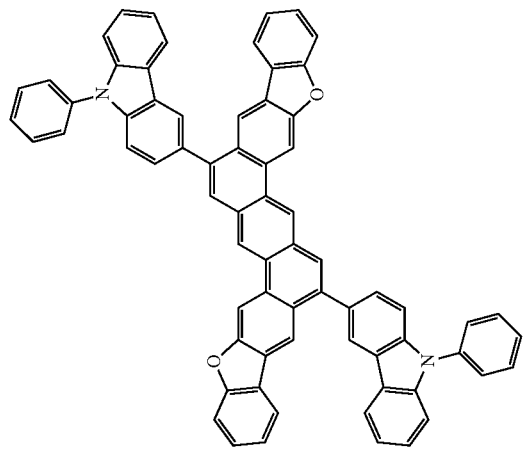
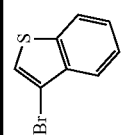
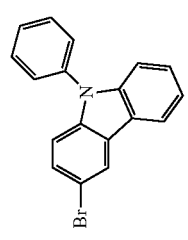

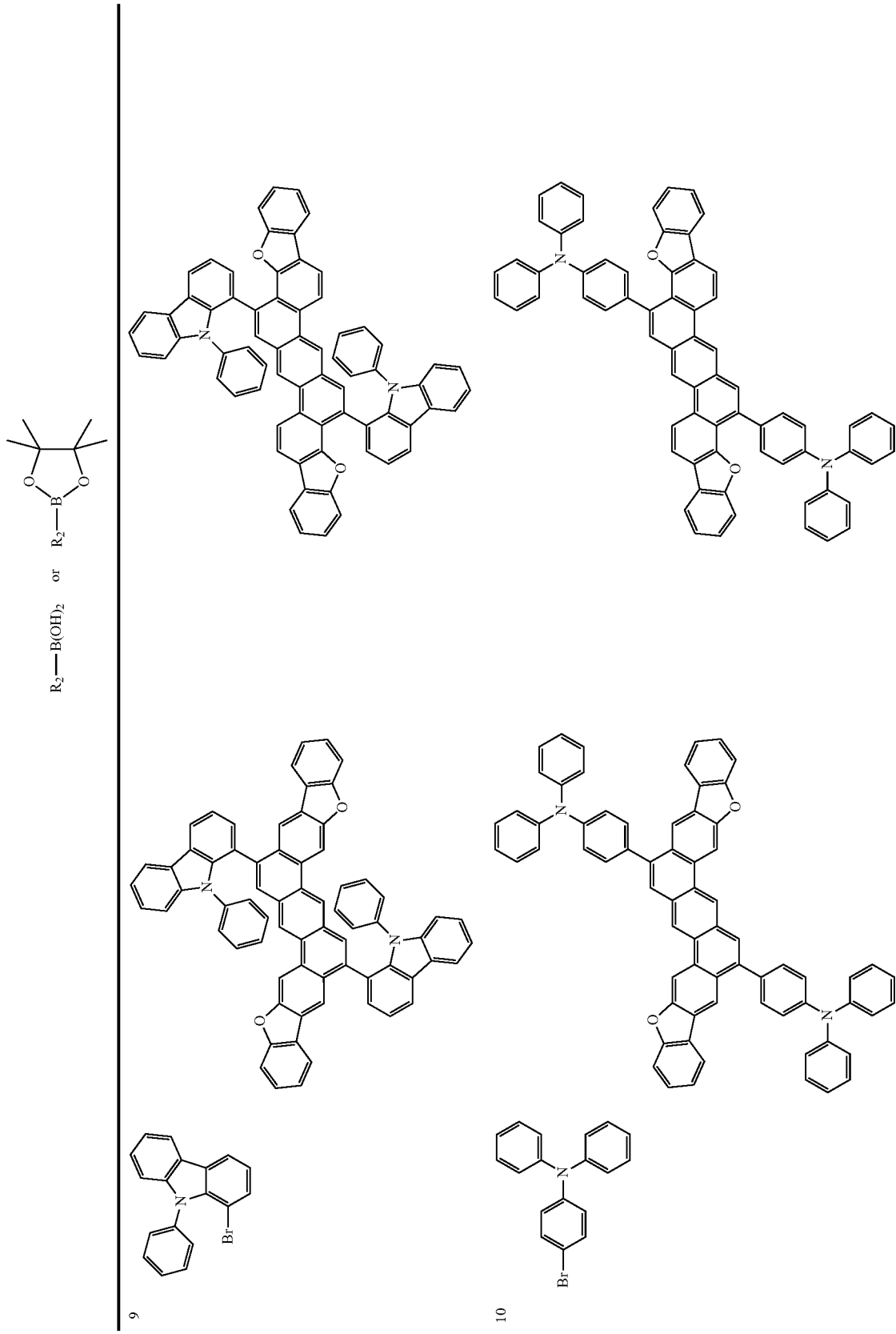

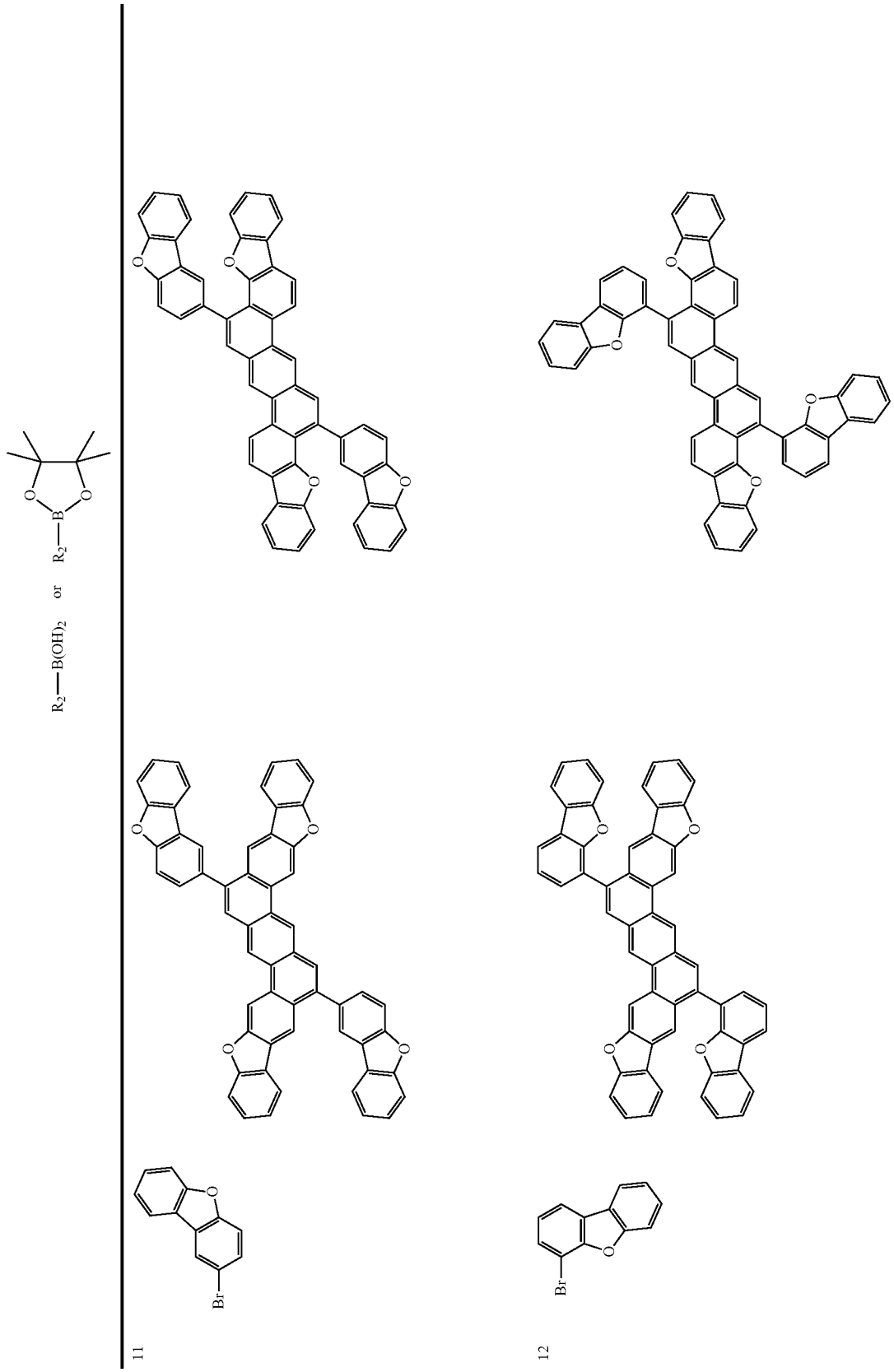

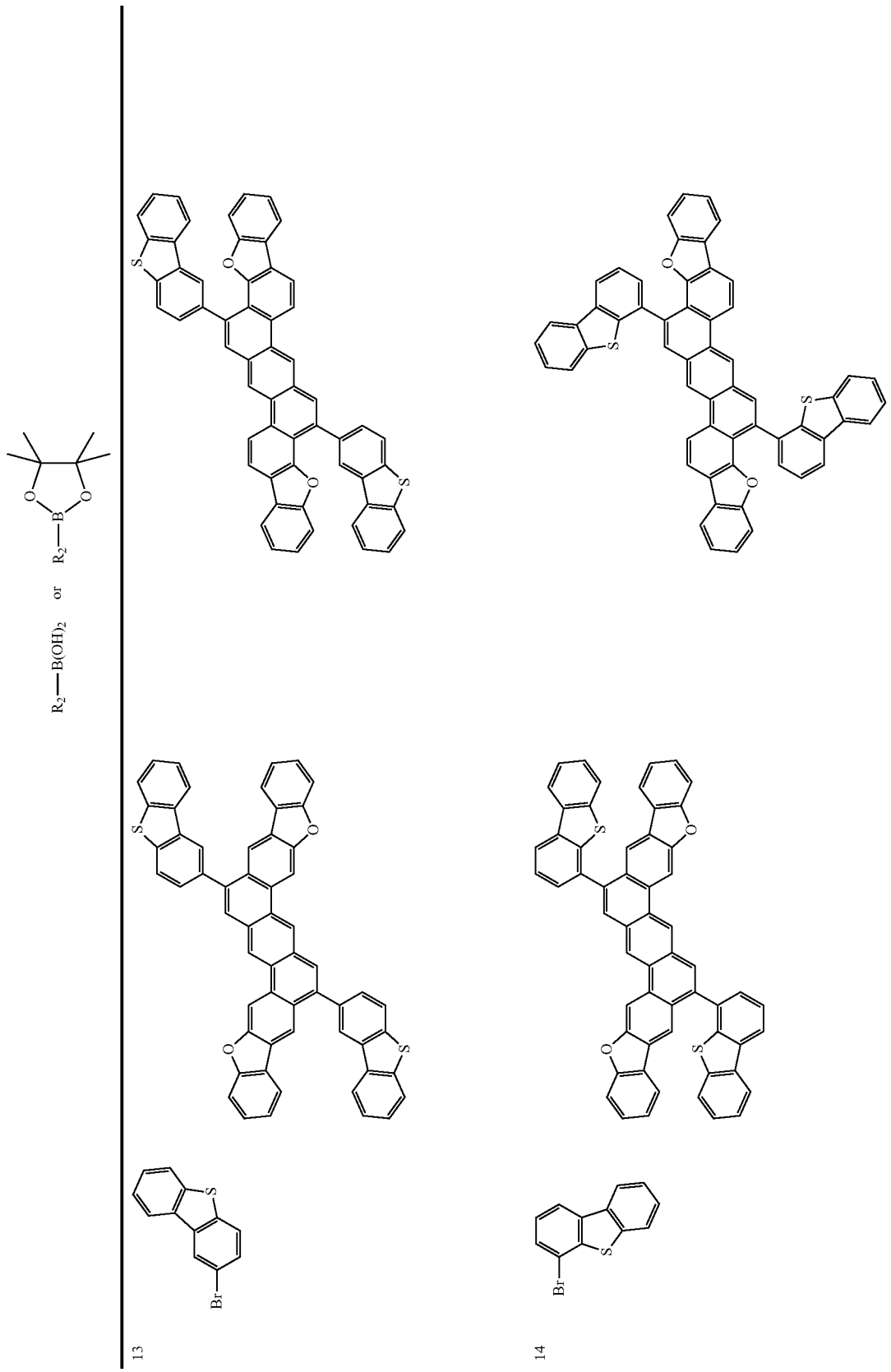

TABLE 2
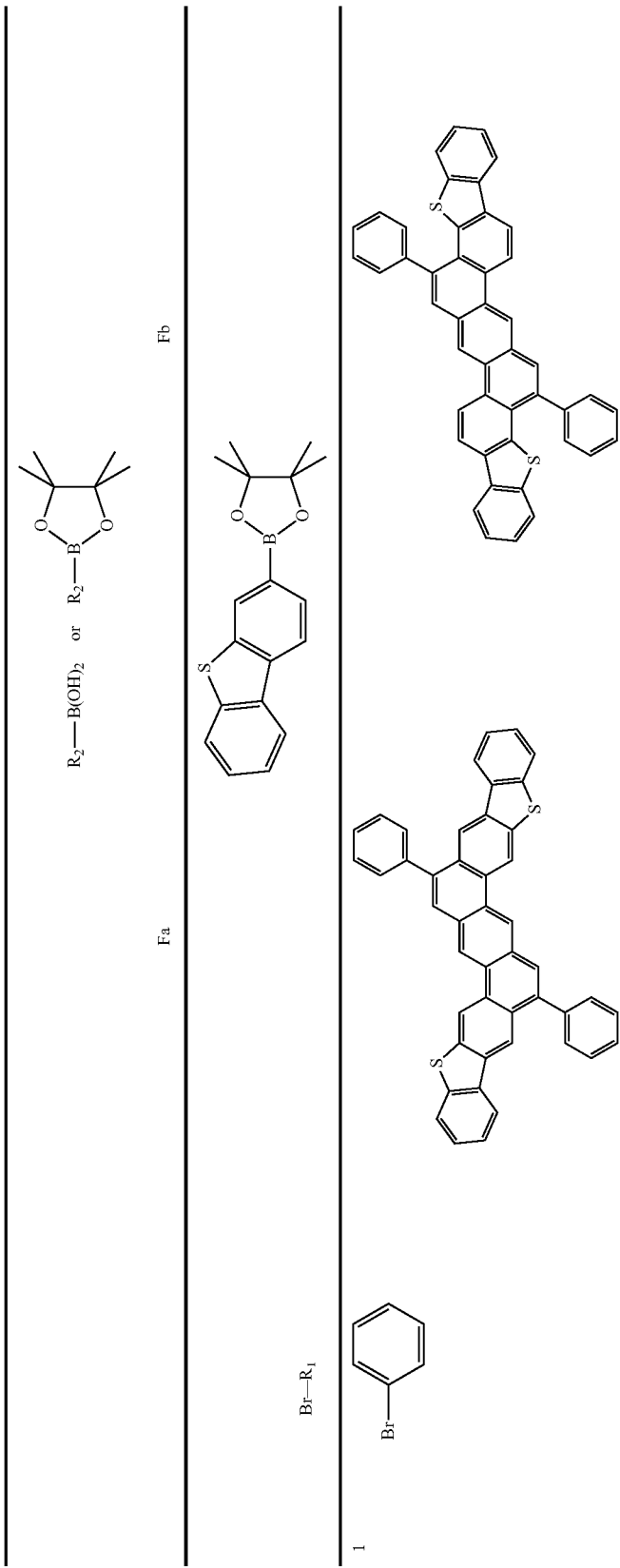

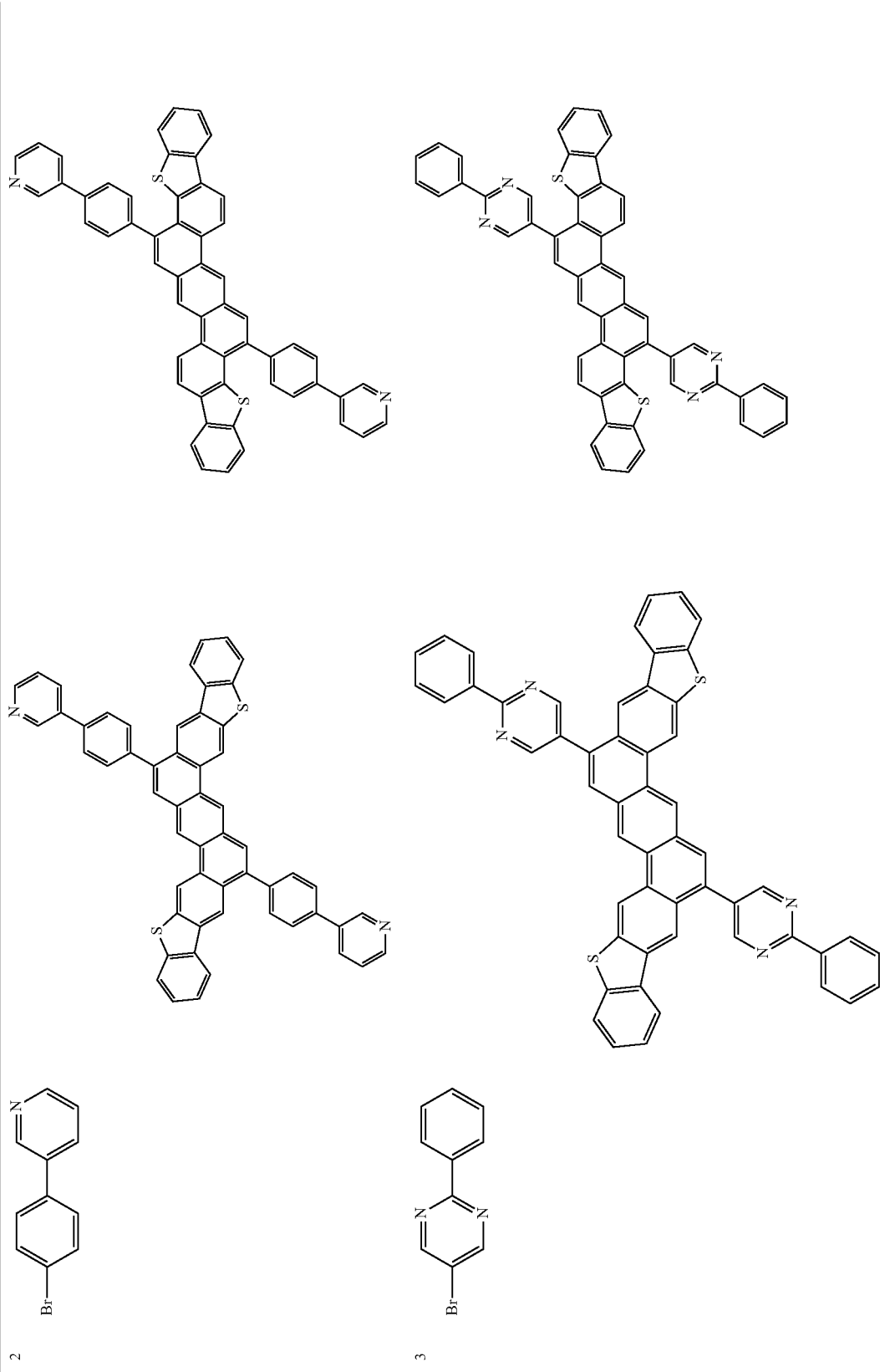

TABLE 2-continued
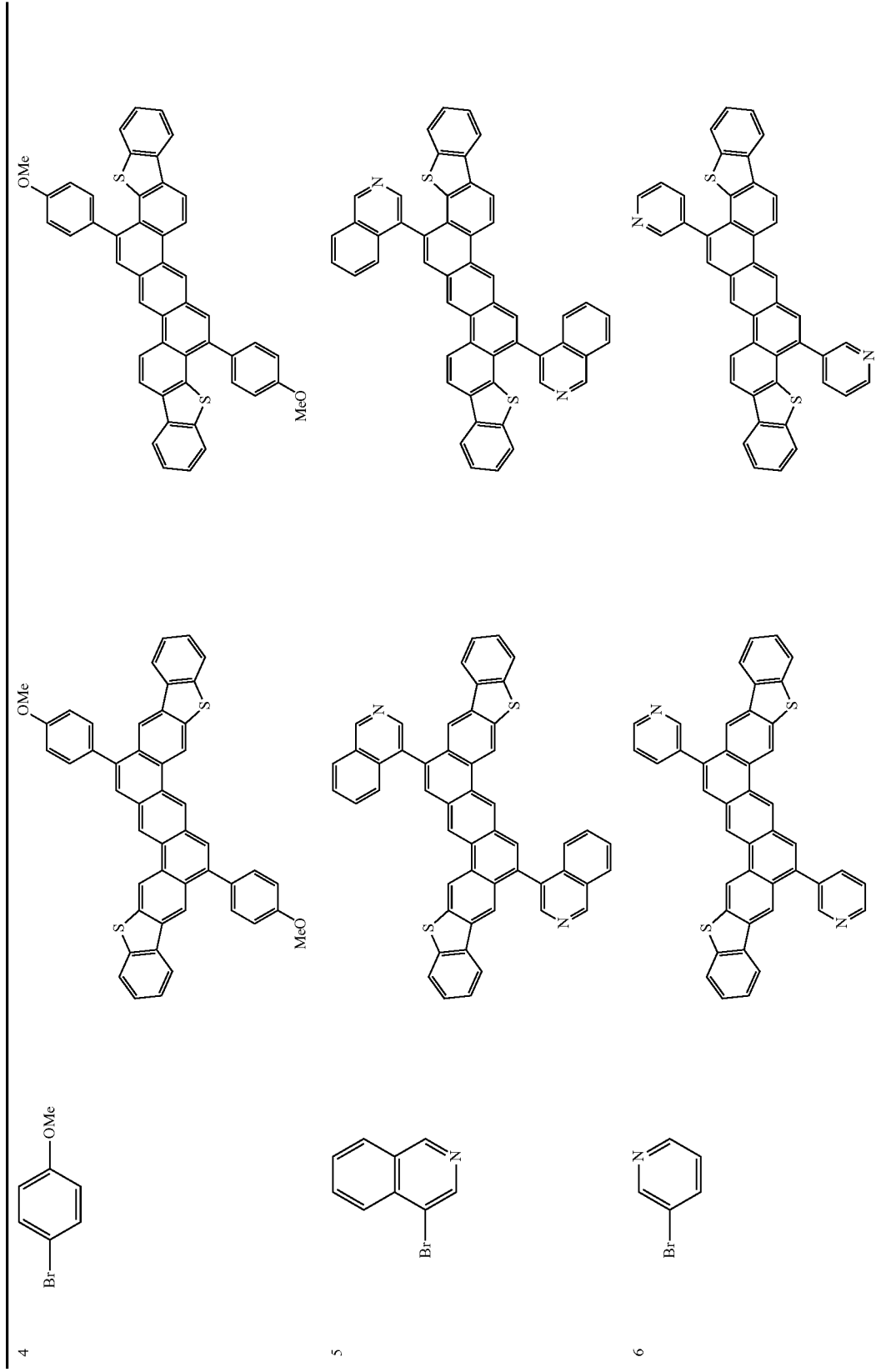

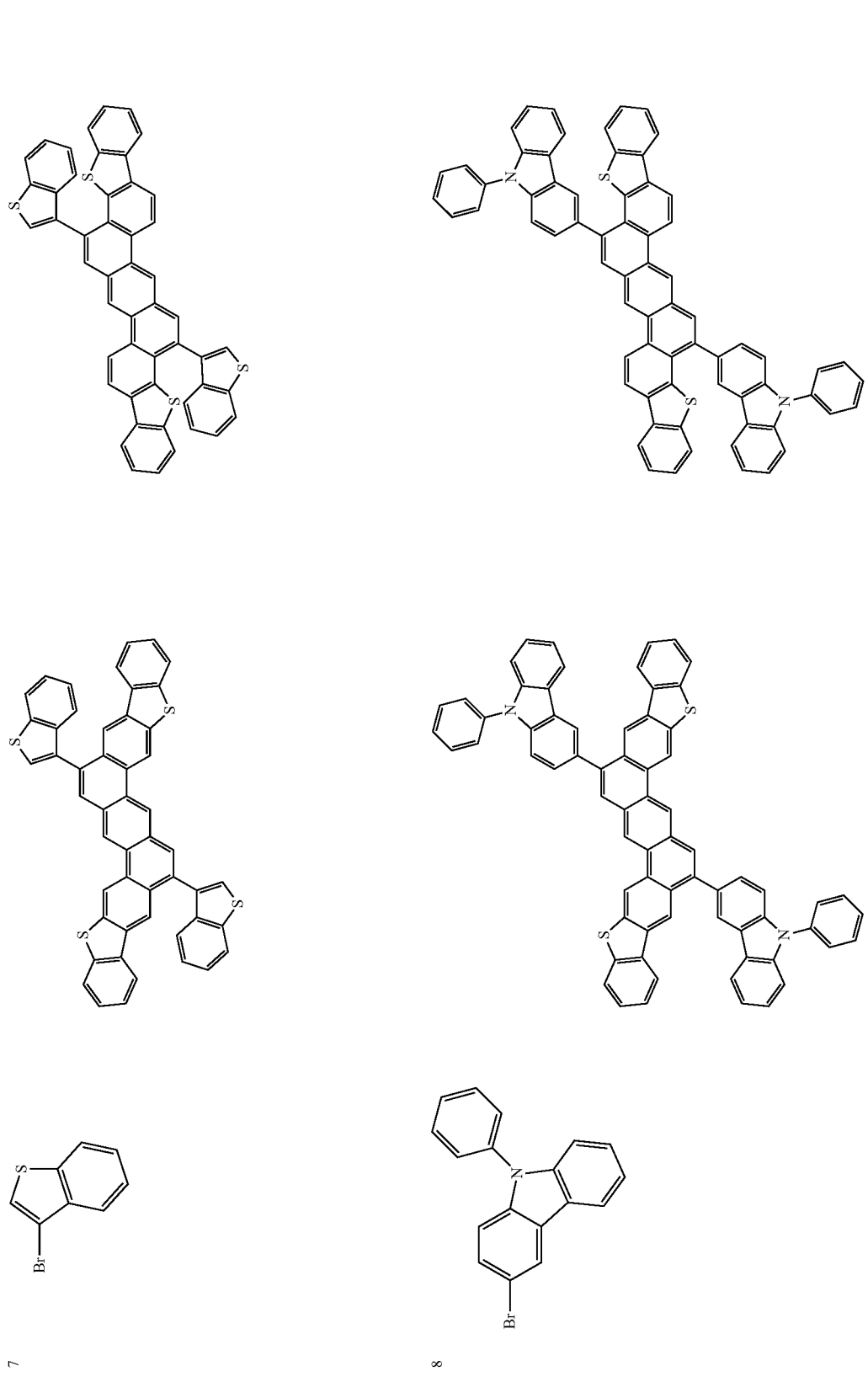

TABLE 2-continued
| | |
|---|---|
| 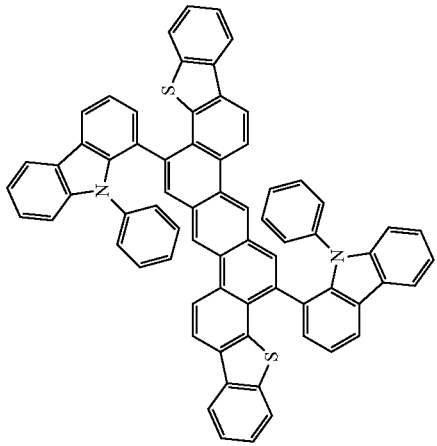 | 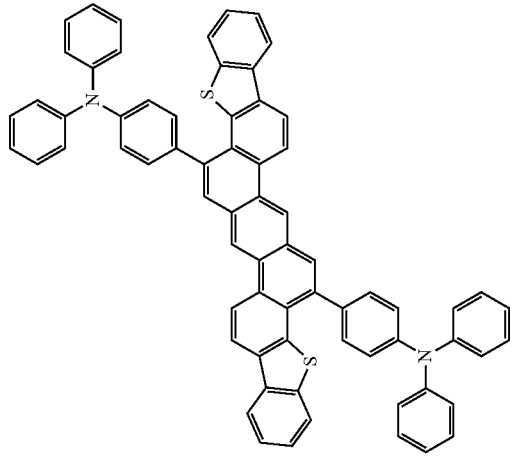 |
| 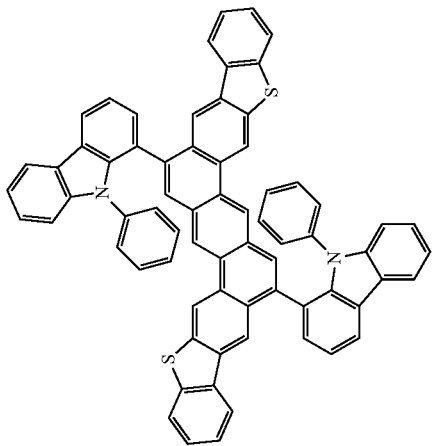 | 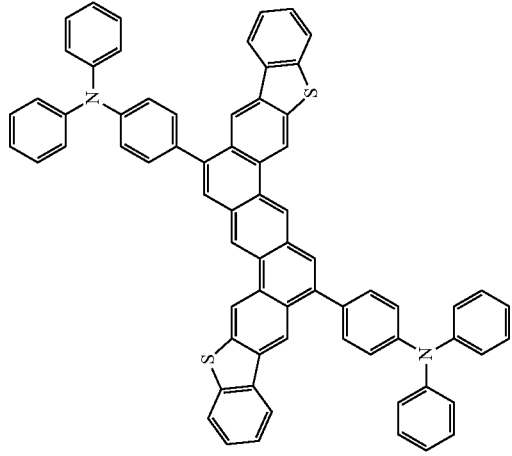 |
| 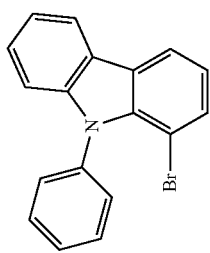 | 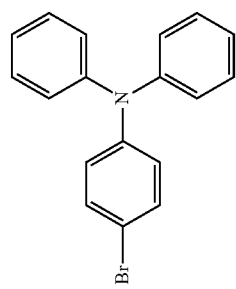 |
| 9 | 10 |

TABLE 2-continued
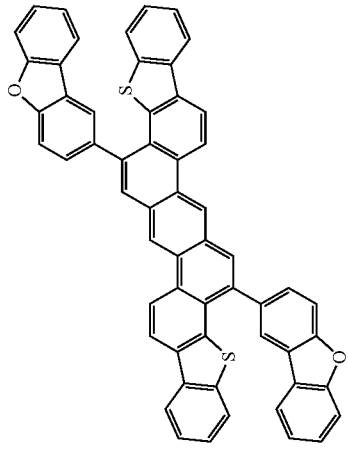 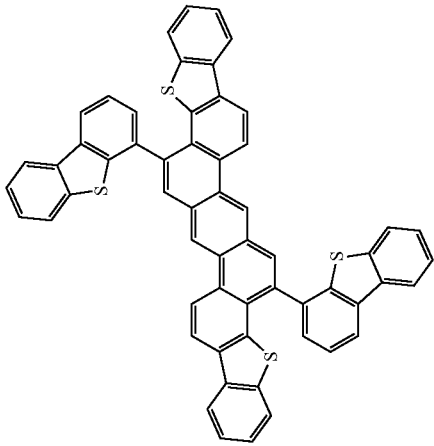
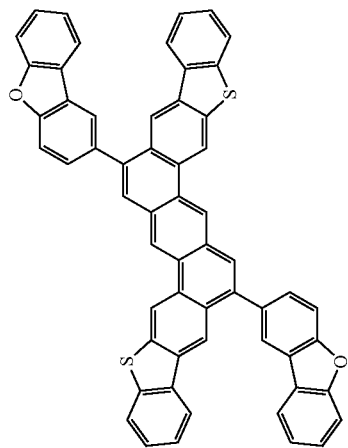 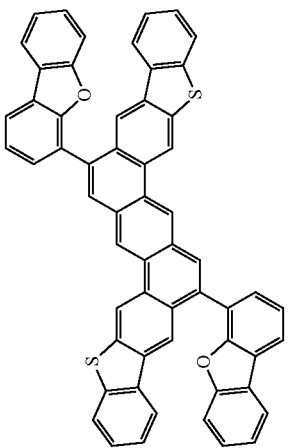
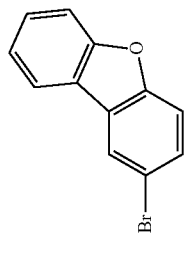 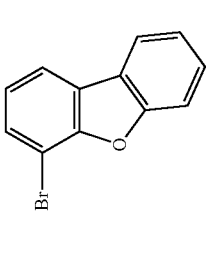
11 12

TABLE 2-continued
| | |
|---|---|
| 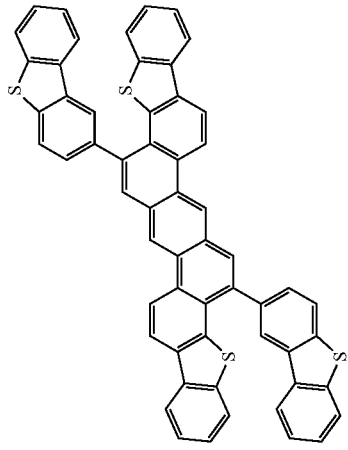 | 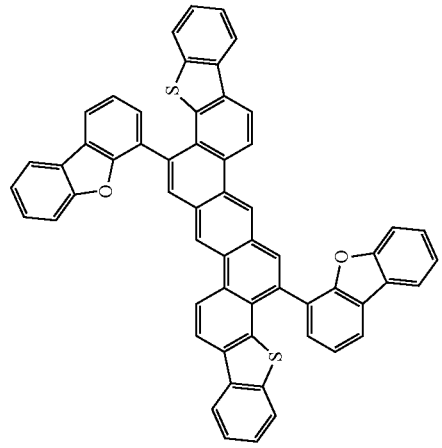 |
| 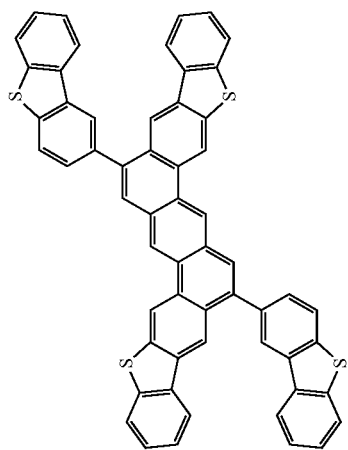 | 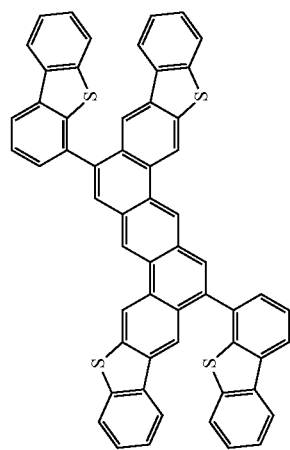 |
| 13 | 14 |

TABLE 2-continued
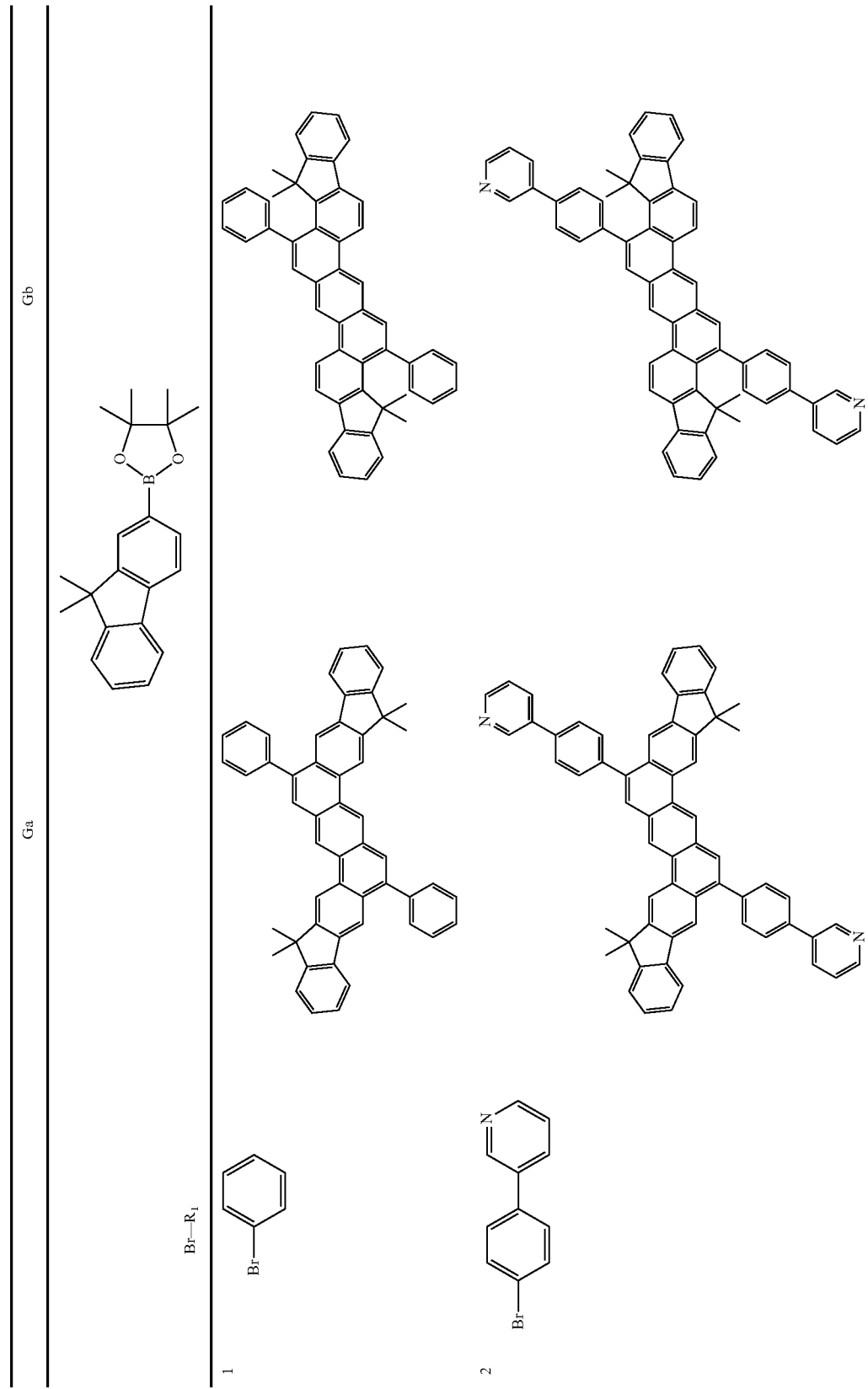

TABLE 2-continued
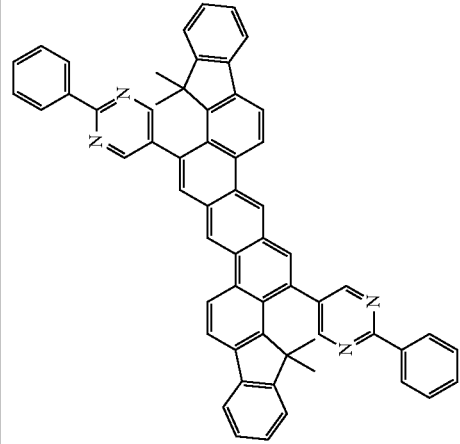
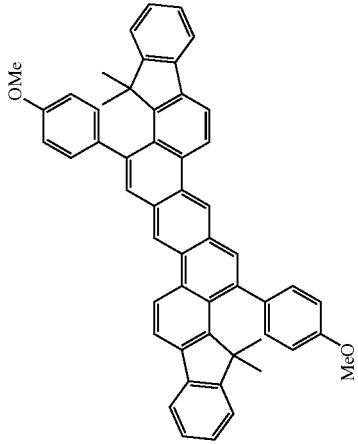
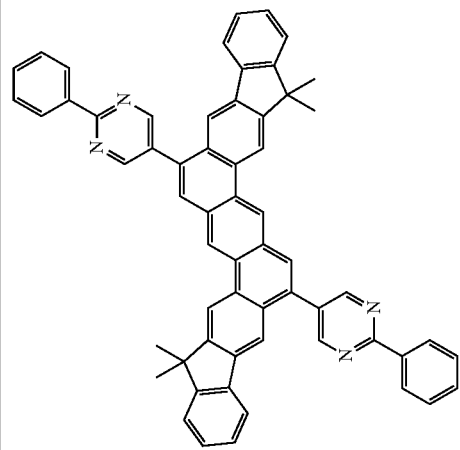
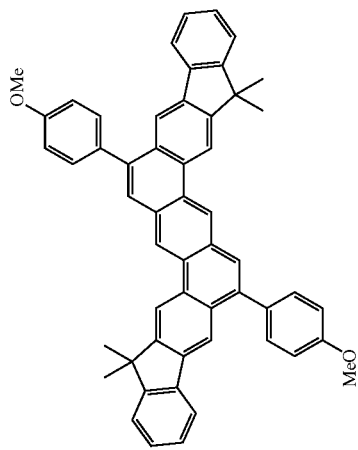
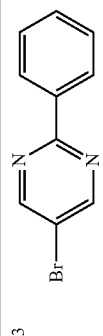
3
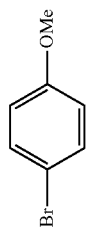
4

TABLE 2-continued
| 5 | 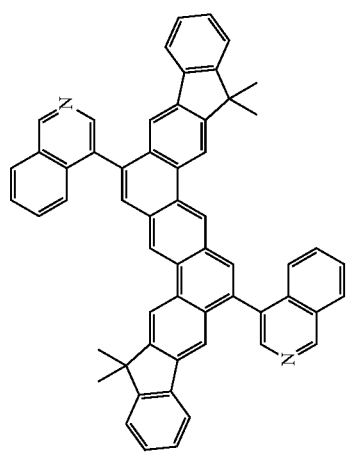 | 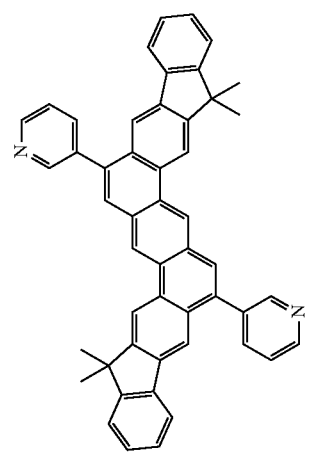 | 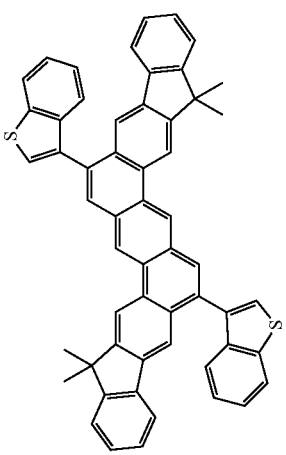 |
| --- | --- | --- | --- |
| 6 | 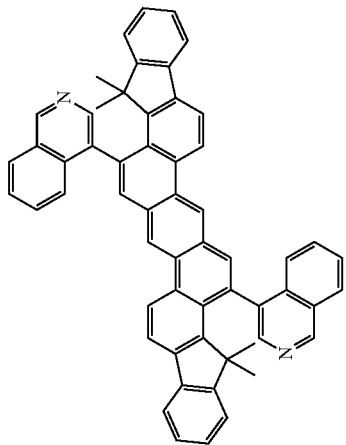 | 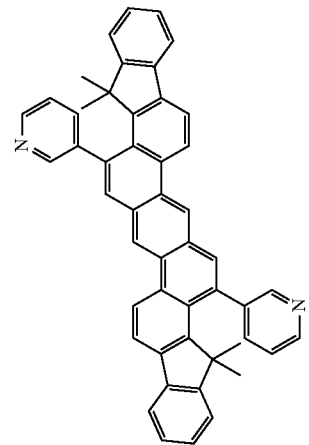 | 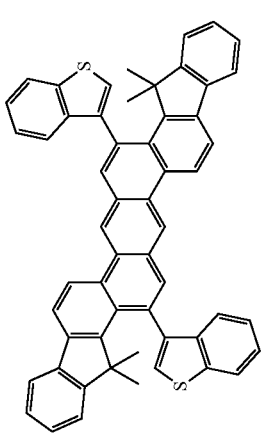 |
| 7 | 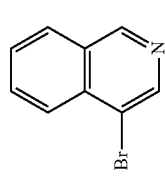 | 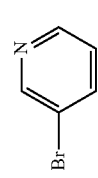 | 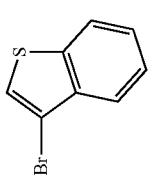 |

TABLE 2-continued
| | |
|---|---|
| 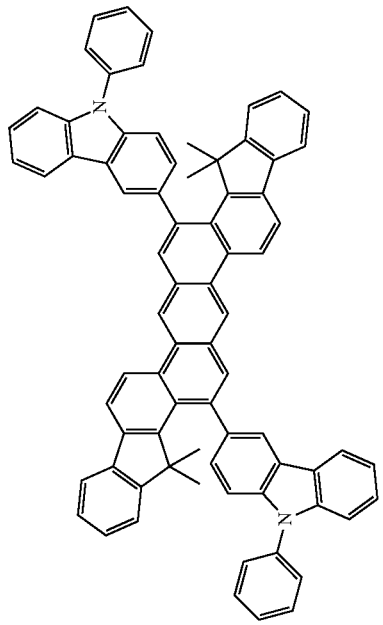 | 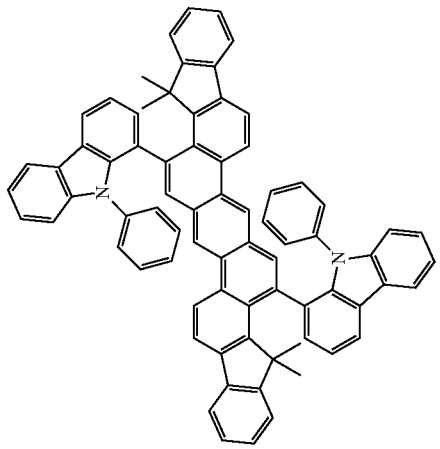 |
| 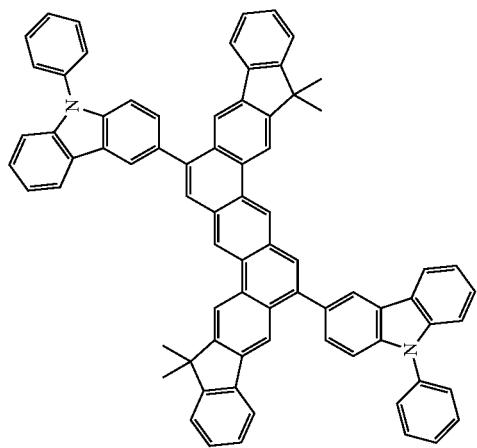 | 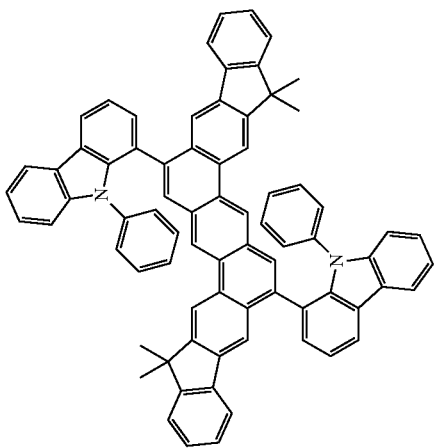 |
| 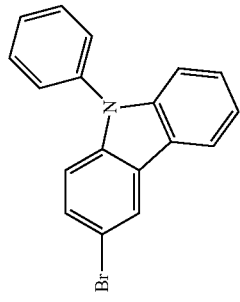 | 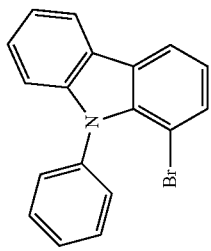 |
| 8 | 9 |

TABLE 2-continued
| | |
|---|---|
| 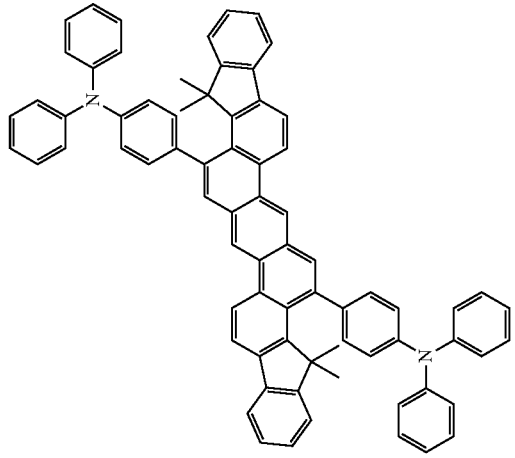 | 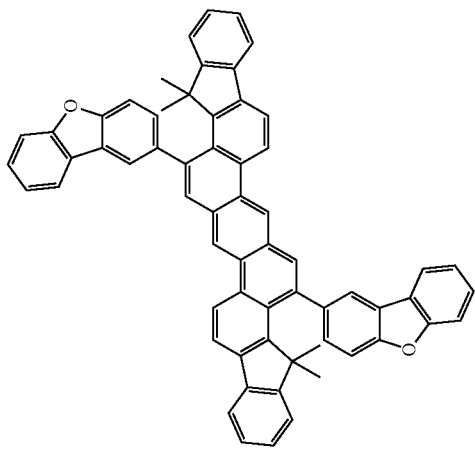 |
| 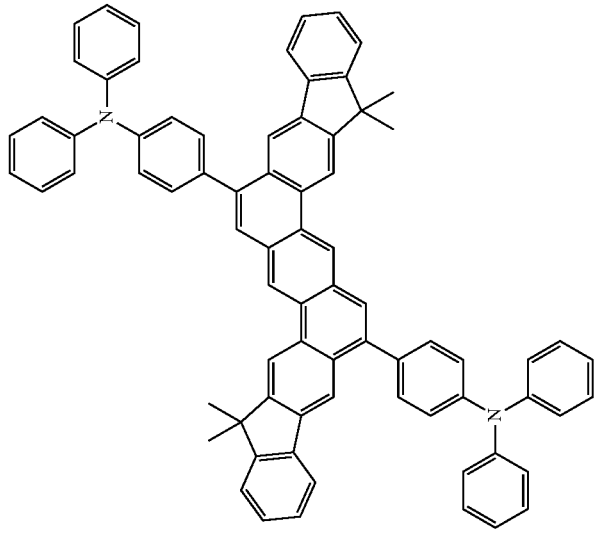 | 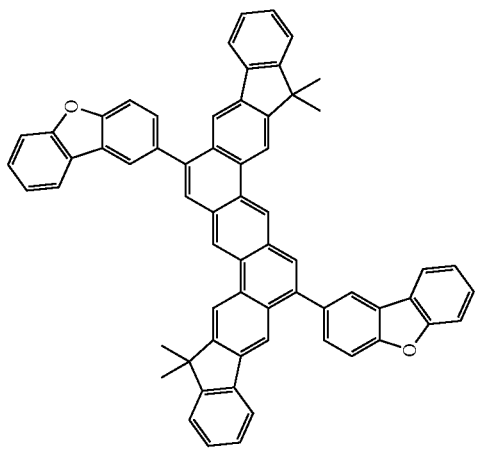 |
| 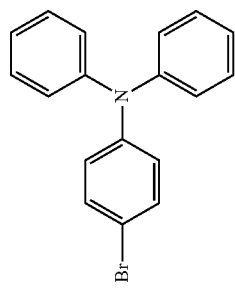<br>10 | 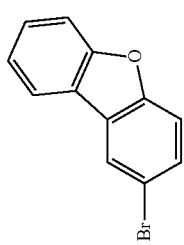<br>11 |

TABLE 2-continued
| | |
|---|---|
| 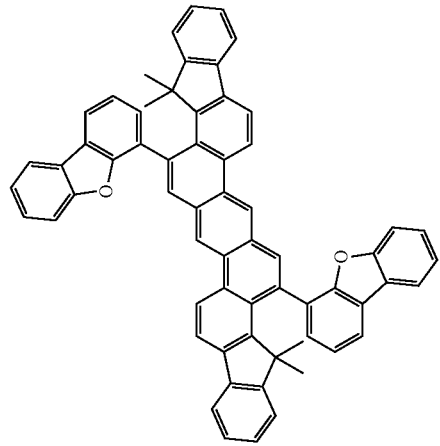 | 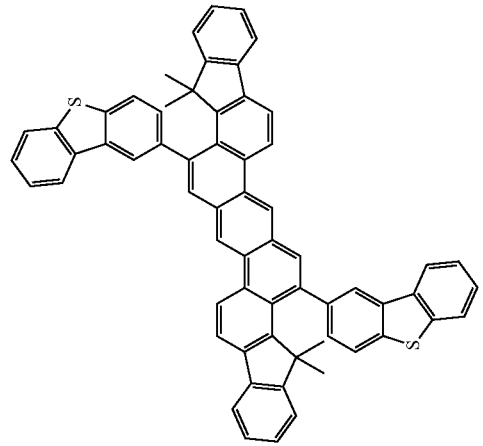 |
| 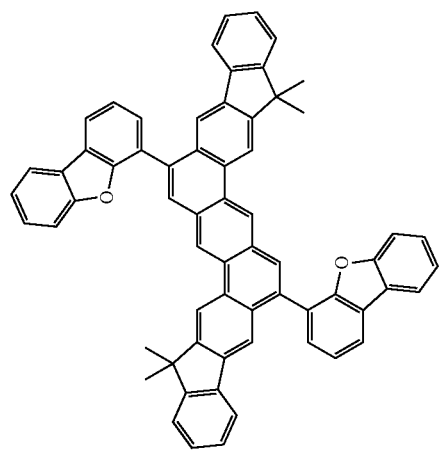 | 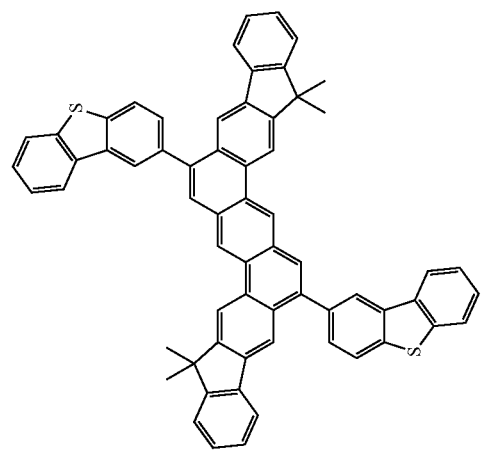 |
| 12 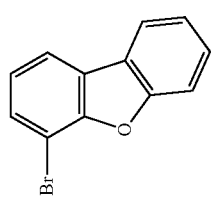 | 13 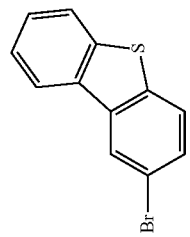 |

TABLE 2-continued
| | |
|---|---|
| 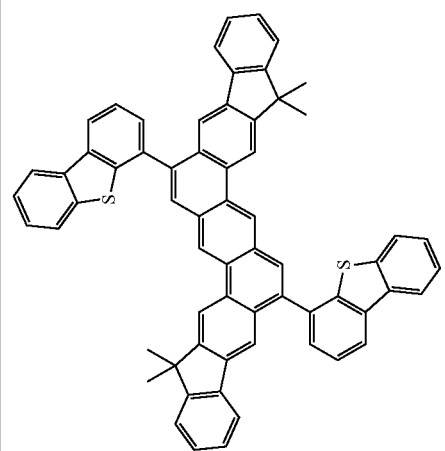 | 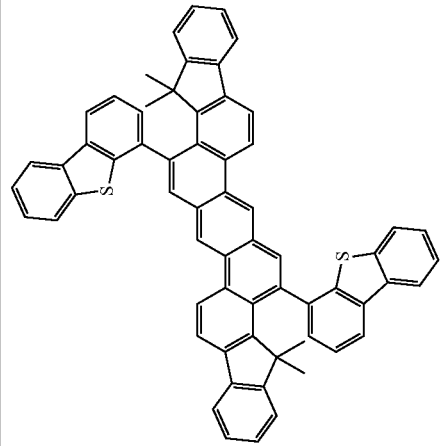 |
| 14 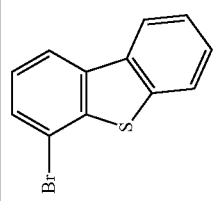 | |

According to an embodiment of the present invention, an organic light-emitting device includes: a first electrode; a second electrode; and an organic layer interposed between the first electrode and the second electrode, wherein the organic layer includes a first layer including the heterocyclic compound described above.

The first layer may include a hole injection layer (HIL), a hole transport layer (HTL), a functional layer having both hole injecting and hole transporting capabilities, an EML, an EIL, an ETL, or a functional layer having both electron injecting and electron transporting capabilities.

Alternatively, the first layer may be an EML, and the heterocyclic compounds of Formulae 1-4 may be used as a fluorescent host or a fluorescent dopant.

The organic layer of the organic light-emitting device may include an EML, an HTL, and an ETL. The first layer may be the EML, and the EML may further include an anthracene compound, an arylamine compound, or a styryl compound, all of which are well known.

At least one hydrogen atom of the anthracene compound, the arylamine compound, and the styryl compound may be substituted with the same substituent groups described above with reference to the C1-C60 alkyl group. The arylamine indicates a C5-C60 arylamine group.

The organic layer of the organic light-emitting device may include an EML, an HTL, and an ETL. The first layer may be the EML, and at least one of the red, green, blue, and white layers of the EML may further include a known phosphorescent compound.

The first layer of the organic light-emitting device may be a blue EML. If the first layer of the organic light-emitting device is a blue EML, the above describe heterocyclic compound may be used as a blue dopant.

Meanwhile, the first electrode may be an anode, and the second electrode may be a cathode, but the reverse is also possible.

For example, the organic light-emitting device according to the current embodiment may have a structure of first electrode/HIL/EML/second electrode, a structure of first electrode/HIL/HTL/EML/ETL/second electrode, or a structure of first electrode/HIL/HTL/EML/ETL/EIL/second electrode. The organic light-emitting device may also have a structure of first electrode/single layer having both hole injecting and hole transporting capabilities/EML/ETL/second electrode, or a structure of first electrode/single layer having both hole injecting and hole first electrode/HIL/HTL/EML/single layer having both electron injecting and electron transporting capabilities/second electrode.

The organic light-emitting device according to the current embodiment may be a top-emission type organic light-emitting device or a bottom-emission type organic light-emitting device.

The organic layer of the organic light-emitting device may include a HIL, a HTL, a functional layer having both hole injecting and hole transporting capabilities, an EML, a hole blocking layer (HBL), an ETL, an EIL, or a combination of at least two thereof, but is not limited thereto. At least one of the HIL, the HTL, and the functional layer having both hole injecting and hole transporting capabilities may further include a charge-generating material in addition to the heterocyclic compound according to an embodiment of the present invention, known hole injecting materials, and known hole transporting materials, in order to improve conductivity of the layers.

The charge-generating material may be a p-dopant. Examples of the p-dopant include a quinone derivative such as tetracyanoquinonedimethane (TCNQ) and 2,3,5,6-tetrafluoro-tetracyano-1,4-benzoquinonedimethane (F4TCNQ); a metal oxide such as tungsten oxide and molybdenum oxide; and a cyano group-containing compound such as Compound 100 below, but are not limited thereto.

Transporting capabilities/EML/ETL/EIL/second electrode. The organic light-emitting device may also have a structure of first electrode/HTL/EML/single layer having both electron injecting and electron transporting capabilities/second electrode, a structure of first electrode/HIL/EML/single layer having both electron injecting and electron transporting capabilities/second electrode, or a structure of

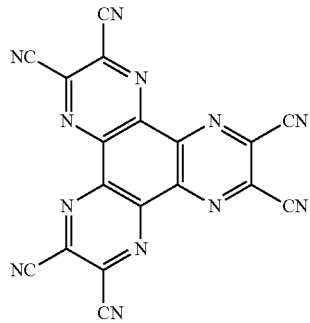

Compound 100

If the HIL, the HTL, or the functional layer having both hole injecting and hole transporting capabilities further includes the charge-generating material, the charge-generating material may be homogeneously or non-homogeneously dispersed between the layers, or a variety of modifications may be possible.

The ETL of the organic light-emitting device may include an electron-transporting organic compound and a metal-containing material. Examples of the electron-transporting compound include anthracene-based compounds such as 9,10-di(naphthalene-2-yl)anthracene) (ADN), and Compounds 101 and 102 below, but are not limited thereto.

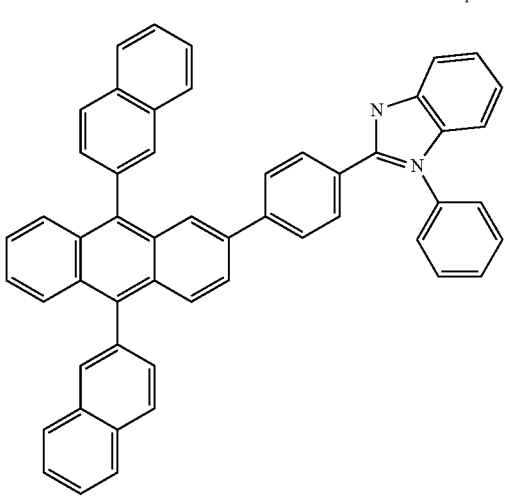

Compound 101

Compound 102

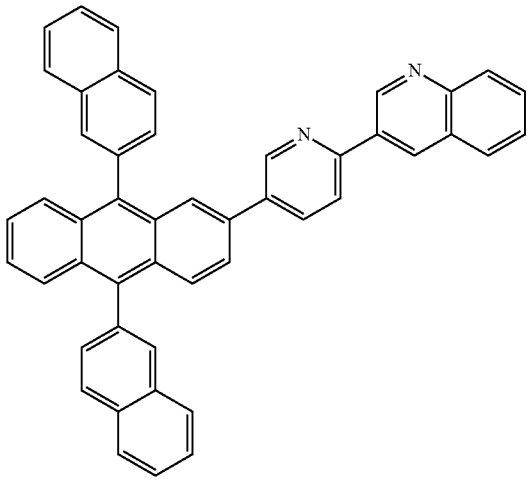

The metal-containing material may include a Li complex. Examples of the Li complex include lithium quinolate (LiQ) or Compound 103 below, but are not limited thereto.

Compound 103

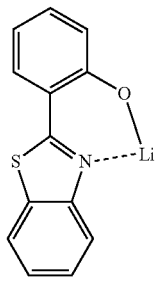

Hereinafter, a method of manufacturing an organic light-emitting device according to an embodiment of the present invention will be described with reference to FIG. 1. Referring to FIG. 1, the organic light-emitting device according to the present embodiment includes a substrate (not shown), a first electrode (anode), a HIL, a HTL, an EML, an ETL, an EIL, and a second electrode (cathode).

First, the first electrode is formed by depositing or sputtering a material for forming the first electrode having a high work function on a substrate. The first electrode may constitute an anode or a cathode. The substrate may be any substrate commonly used in organic light-emitting devices, and may (SnO$_2$), zinc oxide (ZnO), aluminum (Al), silver (Ag), magnesium (Mg), or the like, which has excellent conductivity, and may form a transparent or reflective electrode.

Then, a HIL may be formed on the first electrode by vacuum deposition, spin coating, casting, Langmuir Blodgett (LB) deposition, or the like.

When the HIL is formed using vacuum deposition, the deposition conditions may vary according to a compound that is used to form the HIL, and the structure and thermal characteristics of the HIL to be formed. For example, the deposition conditions may include a deposition temperature of 100 to 500° C., a vacuum pressure of $10^{-8}$ to $10^{-3}$ torr, and a deposition rate of 0.01 to 100 Å/sec.

When the HIL is formed using spin coating, coating conditions may vary according to a compound that is used to form the HIL, and the structure and thermal properties of the HIL to be formed. For example, the coating conditions may include a coating speed of about 2,000 rpm to about 5,000 rpm, and a thermal treatment temperature of about 80° C. to about 200° C., wherein the thermal treatment is for removing a solvent after coating.

The HIL may be formed of any material that is commonly used to form a HIL.

Examples of the material include a phthalocyanine compound such as copperphthalocyanine, 4,4',4"-tris(3-methylphenylphenylamino)triphenylamine (m-MTDATA), N,N'-di(1-naphthyl)-N,N'-diphenylbenzidine (NPB), TDATA, 2T-NATA, polyaniline/dodecylbenzene sulfonic acid (Pani/DBSA), poly(3,4-ethylenedioxythiophene)/poly(4-styrenesulfonate) (PEDOT/PSS), polyaniline/camphor sulfonicacid (Pani/CSA), and (polyaniline)/poly(4-styrenesulfonate) (PANI/PSS), but are not limited thereto include, for example, a glass substrate or a transparent plastic substrate with excellent mechanical strength, thermal stability, transparency, surface smoothness, ease of handling, and water resistance. The material for forming the first electrode may be indium tin oxide (ITO), indium zinc oxide (IZO), tin oxide

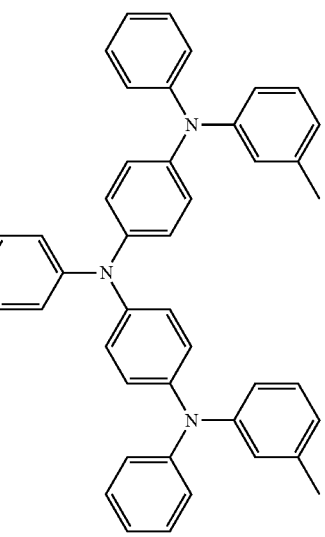

m-MTDATA

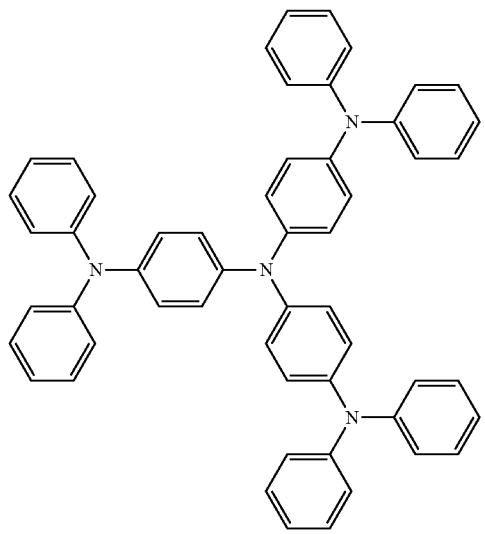

TDATA

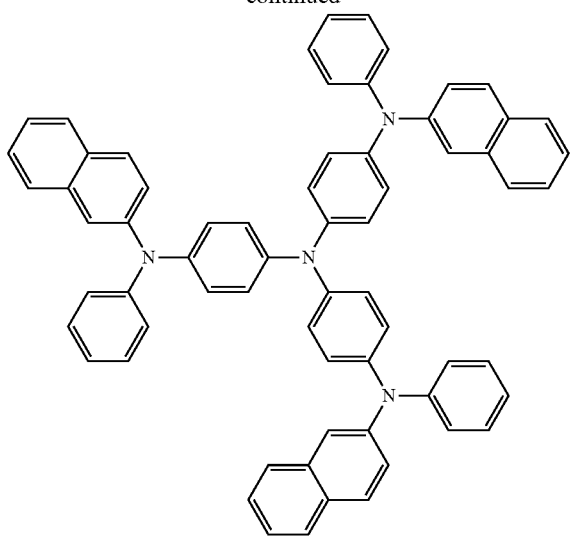

2T-NATA

The thickness of the HIL may be about 100 to 10,000 Å, and for example, 100 to 1,000 Å. When the HIL has a thickness within the above range, the HIL may have excellent hole injection characteristics without an increase in driving voltage.

Then, the HTL may be formed on the HIL using various methods, for example by vacuum deposition, spin coating, casting, and LB deposition. When the HTL is formed using vacuum deposition or spin coating, the deposition or coating conditions may be similar to those applied to form the HIL, although the deposition or coating conditions may vary according to a material used to form the HTL.

Alternatively, known HTL materials may be used. Examples of such HTL materials include, but are not limited to, carbazole derivatives such as N-phenylcarbazole or polyvinylcarbazole, and amine derivatives having an aromatic condensed ring, such as NPB and N,N'-bis(3-methylphenyl)-N,N'-diphenyl-[1,1-biphenyl]-4,4'-diamine (TPD).

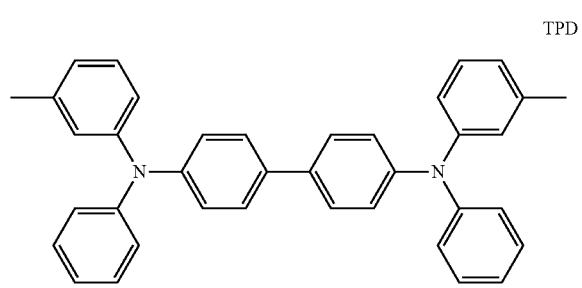

TPD

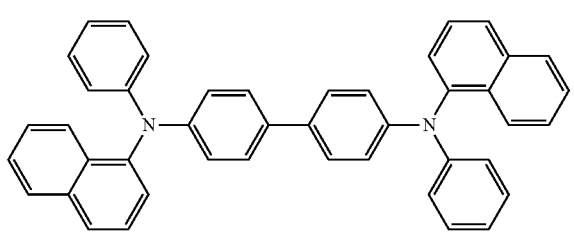

NPB

The HTL may have a thickness of about 50 Å to about 1,000 Å, for example, about 100 Å to about 600 Å. When the HTL has a thickness within the above range, the HTL may have excellent hole transporting characteristics without a substantial increase in driving voltage.

Then, the EML may be formed on the HTL using various methods, for example, vacuum deposition, spin coating, casting, and LB deposition. When the EML is formed using vacuum deposition or spin coating, the deposition or coating conditions may be similar to those applied to form the HIL, although the deposition and coating conditions may vary according to a material that is used to form the EML.

The EML may include the heterocyclic compound described above. In particular, the heterocyclic compound may be used as a host or a dopant. The EML may be formed using a variety of well-known light-emitting materials instead of the heterocyclic compound. Alternatively, the EML may also be formed using a well-known host and a dopant. The dopant for forming the EML may include either a fluorescent dopant or a phosphorescent dopant, which are widely known in the art.

Examples of the host include Alq3, 4,4'-N,N'-dicarbazole-biphenyl (CBP), poly(n-vinylcarbazole) (PVK), 9,10-di(naphthalene-2-yl)anthracene (ADN), TCTA, 1,3,5-tris(N-phenylbenzimidazole-2-yl)benzene (TPBI), 3-tert-butyl-9,10-di(naphtha-2-yl)anthracene (TBADN), E3, and distyrylarylene (DSA), bur are not limited thereto.

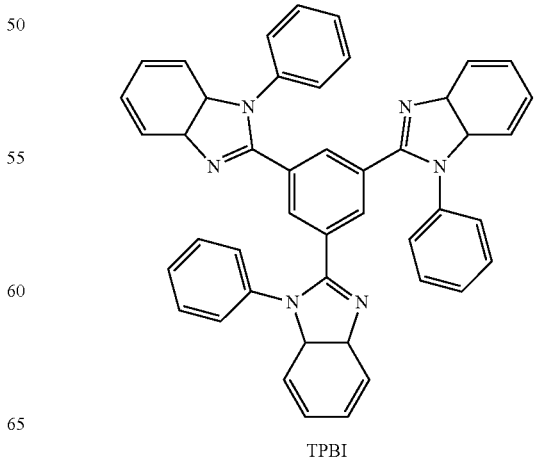

TPBI

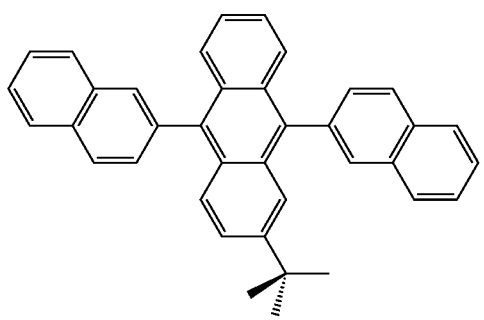

TBADN

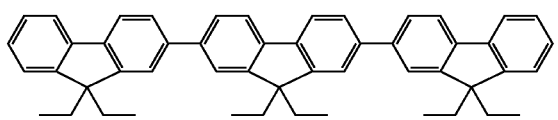

E3

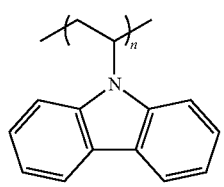

PVK

Examples of well-known red dopants include platinum(II) octaethylporphyrin (PtOEP), Ir(piq)₃, Btp₂Ir(acac), and DCJTB, but are not limited thereto.

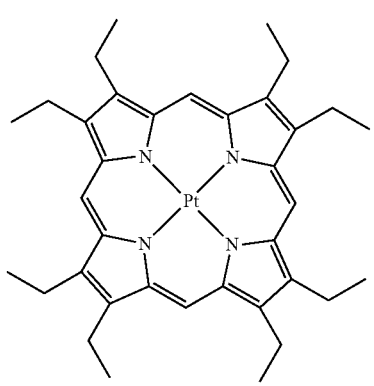

PtOEP

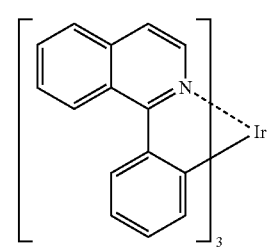

Ir(piq)₃

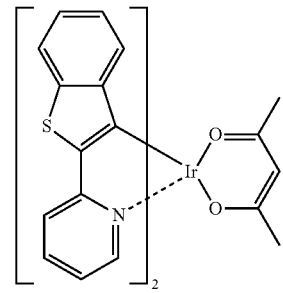

Btp₂Ir(acac)

Examples of known green dopants include Ir(ppy)₃ (where "ppy" denotes phenylpyridine), Ir(ppy)₂(acac), Ir(mpyp)₃, and C545T, but are not limited thereto.

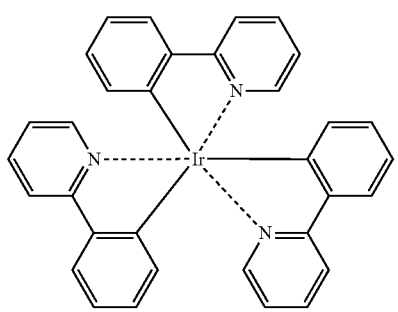

Ir(ppy)₃

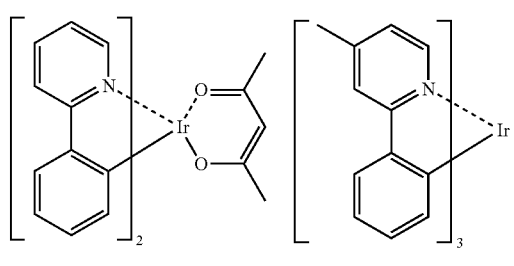

Ir(ppy)₂(acac)          Ir(mpyp)₃

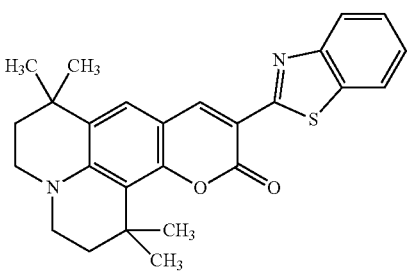

C545T

Meanwhile, examples of the blue dopant include the heterocyclic compound represented by Formula 1. Alternatively, examples of well-known blue dopants include F₂Irpic, (F₂ppy)₂Ir(tmd), Ir(dfppz)₃, ter-fluorene, 4,4'-bis(4-diphenylaminostyryl)biphenyl (DPAVBi), and 2,5,8,11-tetra-t-butyl pherylene (TBPe), but are not limited thereto.

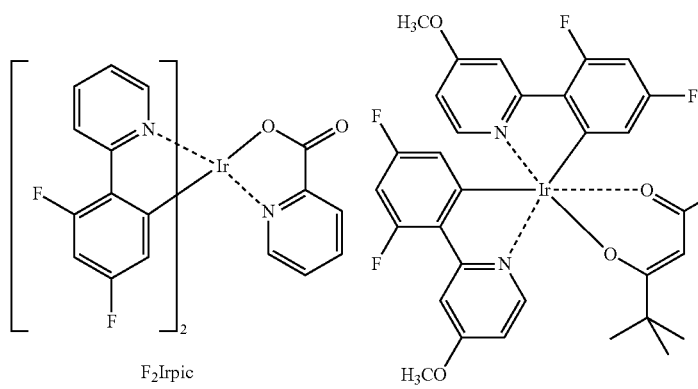

F₂Irpic     (F₂ppy)₂Ir(tmd)     Ir(dfppz)₃

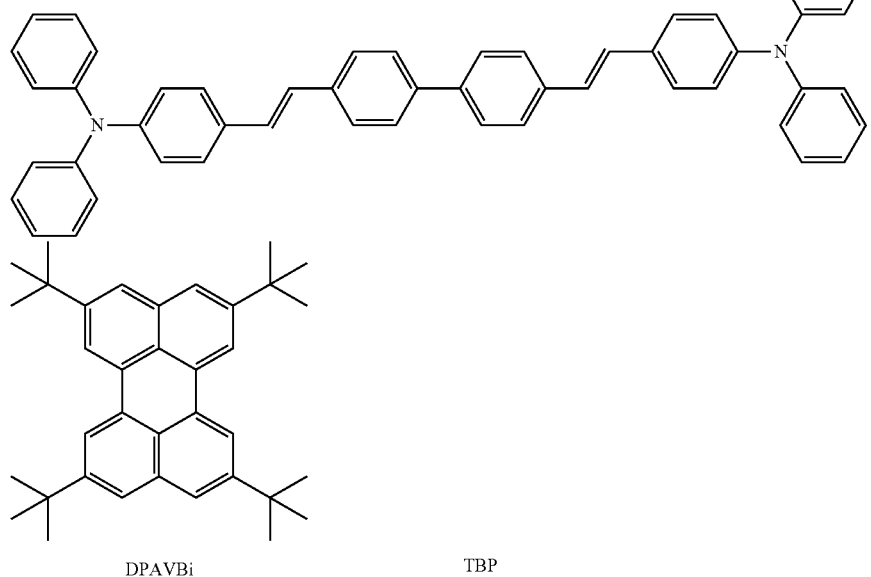

DPAVBi     TBP

The amount of the dopant may be in a range of about 0.1 to about 20 parts by weight, for example, about 0.5 to about 12 parts by weight, based on 100 parts by weight of the EML material (which is equivalent to the total weight of the host and the dopant). When the amount of the dopant is within the above range, concentration quenching may be substantially prevented.

The EML may have a thickness of about 100 Å to about 1,000 Å, for example, about 200 Å to about 600 Å. When the EML has a thickness within the above range, the EML may have excellent light-emitting characteristics without a substantial increase in driving voltage.

When the EML includes a phosphorescent dopant, an HBL (not shown in FIG. 1) may be formed on the EML in order to prevent diffusion of triplet excitons or holes into the ETL. In this case, the HBL may be formed of any material that is commonly used to form a HBL, without limitation. Examples of such HBL materials include oxadiazole derivatives, triazole derivatives, phenathroline derivatives, Balq, and BCP.

The HBL may have a thickness of about 50 Å to about 1,000 Å, for example, about 100 Å to about 300 Å. When the thickness of the HBL is within the range described above, the HBL may have excellent hole blocking characteristics without a substantial increase in driving voltage.

Then, the ETL is formed on the EML (or HBL) using various methods, for example, by vacuum deposition, spin coating, casting, or the like. When the ETL is formed using vacuum deposition or spin coating, the deposition or coating conditions may be similar to those applied to form the HIL, although the deposition and coating conditions may vary according to the material that is used to form the ETL.

The electron transporting material may include the heterocyclic compound described above. Alternatively, the ETL may be formed of any material that is widely known in the art. Examples of electron transporting materials include quinoline derivatives, such as tris(8-quinolinolate)aluminum (Alq3), TAZ, or Balq, but are not limited thereto.

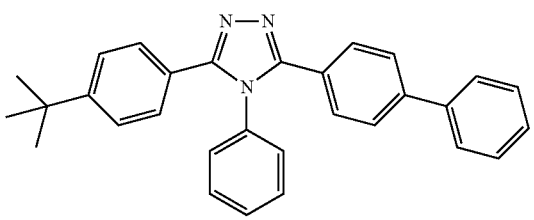

TAZ

BAlq

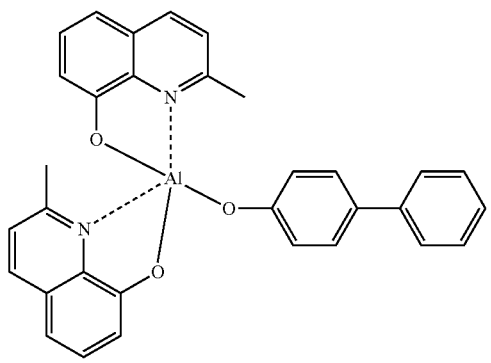

The ETL may have a thickness of about 100 Å to about 1,000 Å, for example, about 100 Å to about 500 Å. When the ETL has a thickness within the above range, the ETL may have excellent electron transporting characteristics without a substantial increase in driving voltage.

In addition, the EIL, which facilitates injection of electrons from the cathode, may be formed on the ETL.

Alternatively, well-known materials, such as LiF, NaCl, CsF, $Li_2O$, or BaO, may be used to form the EIL. The deposition or coating conditions for forming the EIL may be similar to those applied to form the HIL, although the deposition and coating conditions may vary according to the material that is used to form the EIL.

The EIL may have a thickness of about 1 Å to 100 Å, for example, about 5 Å to about 90 Å. When the EIL has a thickness within the above range, the EIL may have excellent electron injecting characteristics without a substantial increase in driving voltage.

Finally, the second electrode may be formed on the EIL using, for example, vacuum deposition, sputtering, or the like. The second electrode may constitute a cathode or an anode. The material for forming the second electrode may include a metal, an alloy, or an electrically conductive compound which has a low work function, or a mixture thereof. In this regard, the second electrode may be formed of lithium (Li), magnesium (Mg), aluminum (Al), aluminum (Al)-lithium (Li), calcium (Ca), magnesium (Mg)-indium (In), magnesium (Mg)-silver (Ag), or the like. In addition, in order to manufacture a top-emission type organic light-emitting device, a transparent cathode formed of a transparent material such as ITO or IZO may be used as the second electrode.

The organic light-emitting device according to the current embodiment may be included in various types of flat panel display devices, such as a passive matrix organic light-emitting display device or an active matrix organic light-emitting display device. In particular, when the organic light-emitting device is applied to an active matrix organic light-emitting display device including a thin-film transistor, the first electrode formed on the substrate may function as a pixel electrode, electrically connected to a source electrode or a drain electrode of the thin-film transistor. Moreover, the organic light-emitting device may also be applied to a flat panel display device having a double-sided screen.

According to an embodiment, an organic light-emitting device may include a plurality of organic layers, wherein at least one of the organic layers may be formed of the heterocyclic compound of the embodiments of the present application by using a deposition method or a wet method of coating a solution of the heterocyclic compound of the embodiments of the present application.

Hereinafter, one or more embodiments will be described in detail with reference to the following examples. However, theses examples are not intended to limit the purpose and scope of the invention.

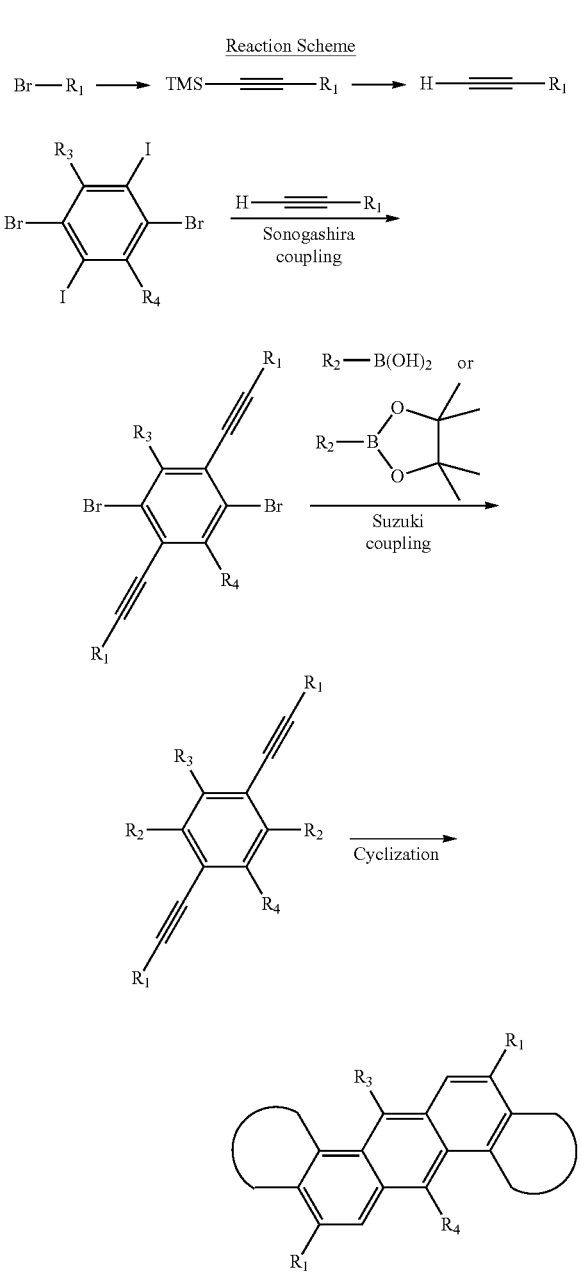

Reaction Scheme

A compound according to an embodiment of the present invention was synthesized by using known Sonogashira coupling, Suzuki coupling, and cyclization.

Representative Synthesis Example 1
Synthesis of Compound 8A
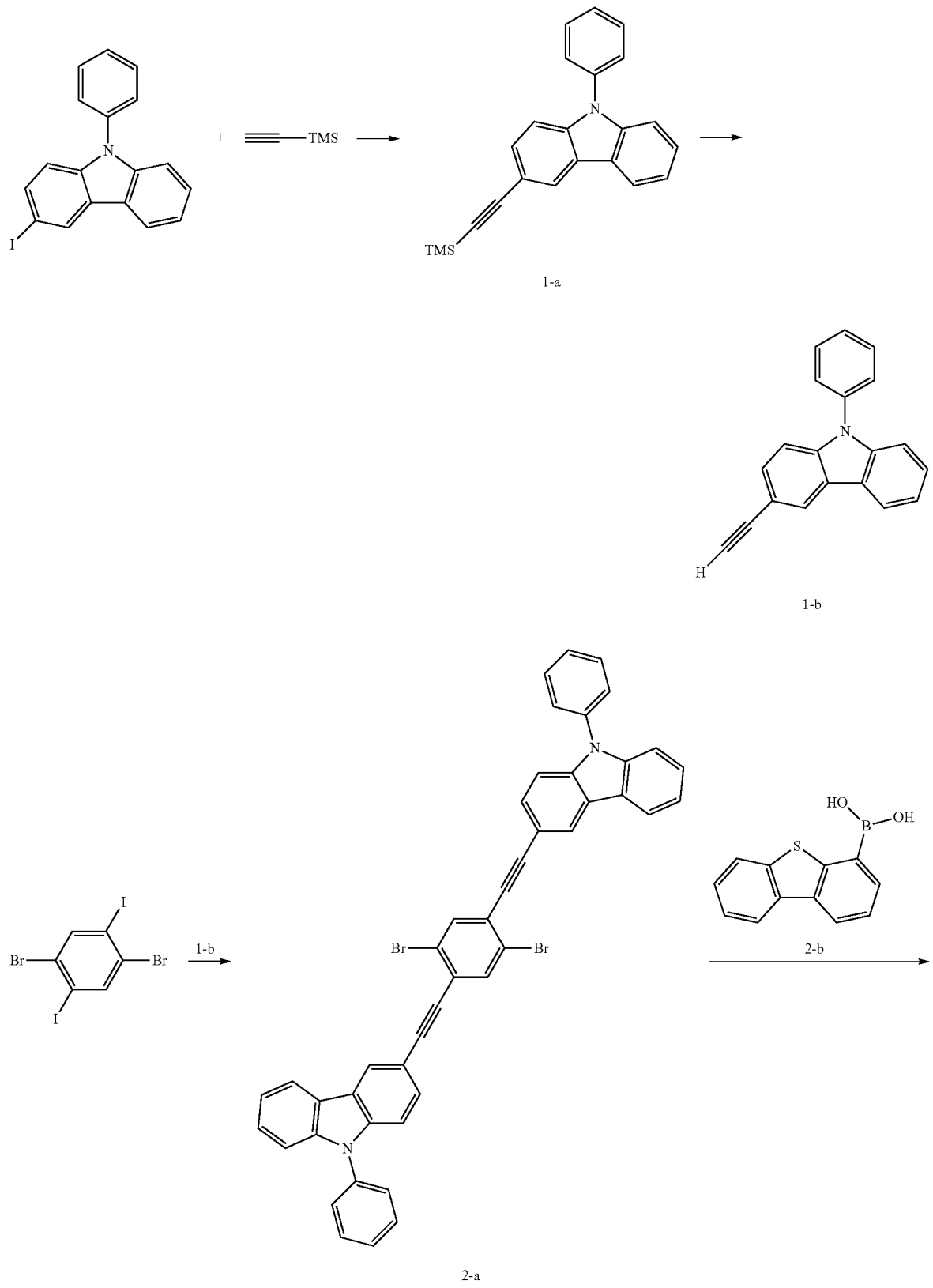

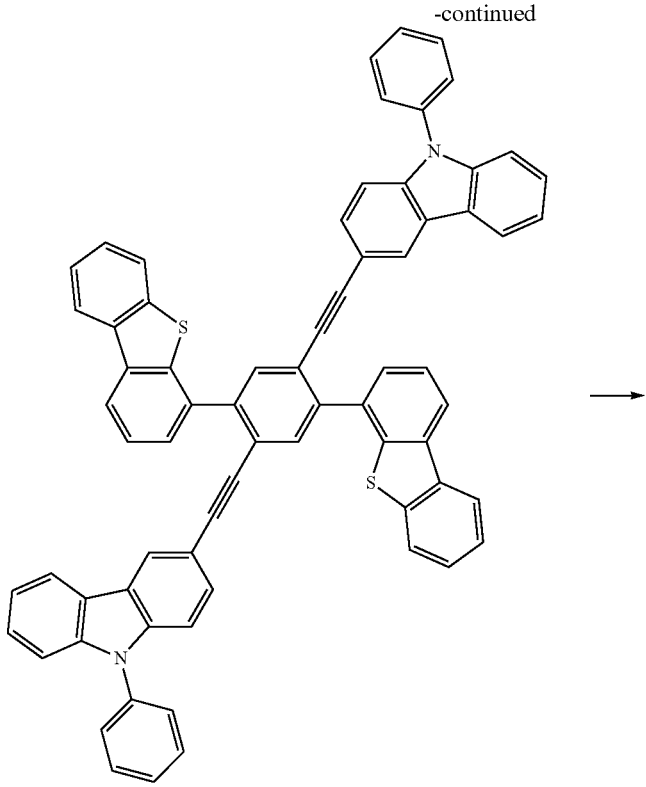

2-c

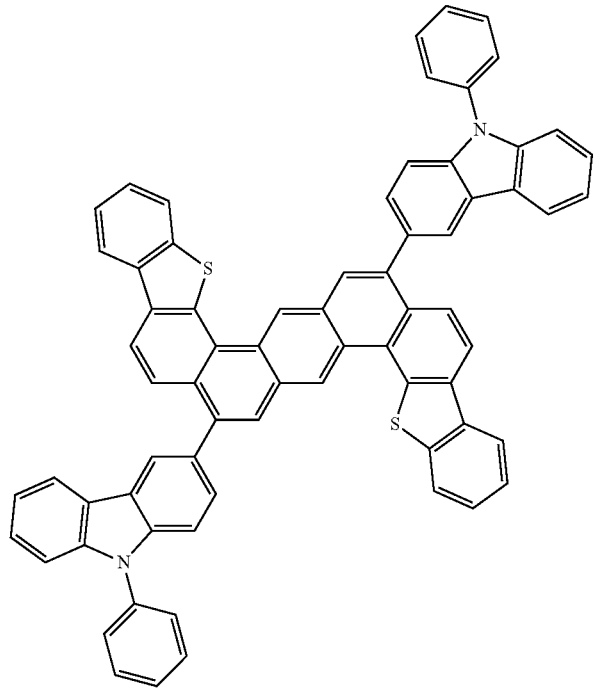 [SMILES: c1ccc(-n2c3ccccc3c3cc(-c4cc5cc6c(cc(-c7ccc8c(c7)c7ccccc7n8-c7ccccc7)c7ccc8c9ccccc9oc8c76)cc5c5c4ccc4c6ccccc6oc45)ccc32)cc1]

8A

Synthesis of Intermediate 1-a 22 g of 3-Iodo-9-phenyl-9H-carbazole, 2.8 g (0.04 eq) of Pd(PPh$_3$)$_4$, 914 mg (0.08 eq) of CuI were added to a flask, the flask was vacuumized, and N$_2$ gas was added to the flask. 200 mL of THF was added thereto, and the flask was stirred. Then, 10 mL (1.2 eq) of triethylamine and 10.0 g (1.2 eq) of TMS-acetylene were slowly added thereto, and the flask was stirred in a N$_2$ atmosphere at room temperature for 2 hours. The solvent was removed using a rotary evaporator, and the resultant was subjected to extraction twice with 200 mL of Et₂O and 150 mL of water. An organic layer was collected and dried using magnesium sulfate and the solvent was evaporated. The residue was separately purified using silica gel column chromatography to obtain 20 g of Intermediate I-a (Yield: 99%) The produced compound was identified using LC-MS. $C_{23}H_{21}N_1Si_1$:M+ 339.14

Synthesis of Intermediate 1-b 4.2 g of Intermediate 1-a was dissolved in 50 mL of THF, 30 mL (3 eq) of tetrabutylammonium fluoride in THF (1.0M) was added thereto in drops, and the mixture was stirred for 30 minutes. 50 mL of water was added thereto, and the mixture was subjected to extraction three times with 50 mL of ethyl ether. An organic layer was collected and dried using magnesium sulfate and the solvent was evaporated. The residue was separately purified using silica gel column chromatography to obtain 3.5 g of Intermediate I-b (Yield: 95%) The produced compound was identified using LC-MS. $C_{20}H_{13}N_1$: M+ 267.10

Synthesis of Intermediate 2-a 2.56 g (0.48 eq) of 1,4-dibromo-2,5-diiodo-benzene, 1.06 g (0.07 eq) of Pd(PPh₃)₄, and 350 mg (0.14 eq) of CuI were added to a flask, the flask was vacuumized, and N₂ gas was added to the flask. 50 mL of THF was added thereto, and the flask was stirred. Then, 4.0 mL (2.2 eq) of triethylamine and 3.5 g (1 eq) of Intermediate 1-b were slowly added thereto, and the flask was stirred in a N₂ atmosphere at room temperature for 2 hours. The solvent was removed using a rotary evaporator, 50 mL of water was added thereto, and the mixture was subjected to extraction three times with 50 mL of ethyl ether. An organic layer was collected and dried using magnesium sulfate and the solvent was evaporated. The residue was separately purified using silica gel column chromatography to obtain 6.32 g of Intermediate 2-a (Yield: 63%) The produced compound was identified using LC-MS. $C_{47}H_{27}Br_2N_2$: M+ 766.04

Synthesis of Intermediate 2-c 5.0 g of Intermediate 2-a, 3.27 g (2.2 eq) of Compound 2-b (available from Aldrich), 750 mg (0.10 eq) of Pd(PPh₃)₄, and 9.0 g (10 eq) of K₂CO₃ were dissolved in a mixture of 100 mL of THF and 30 mL of distilled water. The mixture was stirred at 120° C. while refluxing for 24 hours. The mixture was cooled to room temperature and subjected to extraction three times with 100 mL of water and 100 mL of diethyl ether. An organic layer was collected and dried using magnesium sulfate and the solvent was evaporated. The residue was separately purified using silica gel column chromatography to obtain 5.1 g of Intermediate 2-c (Yield: 81%) The produced compound was identified using LC-MS. $C_{70}H_{40}N_2S_2$: M+ 972.26

Synthesis of Compound 8A 3 g of Intermediate 2-c was dissolved in 50 mL of methylene chloride, and 8.6 mL (40 eq) of trifluoroacetic acid was slowly added thereto. The mixture was stirred at room temperature for 1 hour. Then, the mixture was subjected to extraction three times with 100 mL of water and 100 mL of diethyl ether. An organic layer was collected and dried using magnesium sulfate and the solvent was evaporated. The residue was separately purified using silica gel column chromatography to obtain 2.7 g of Compound 8A (Yield: 90%) The produced compound was identified using LC-MS. $C_{70}H_{40}N_2S_2$: M+ 972.26

Compounds 1A to 14Gb were synthesized in the same manner as in the synthesis of Compound 8A using the same molar ratio.

LC-MS and NMR data of the compounds are shown in Tables 3 to 18 below.

TABLE 3

| number | LC-MS | NMR |
|---|---|---|
| 1A | $C_{46}H_{26}S_2$ M+ 642.15 | 8.31(s, 2H), 8.13-8.12(d, 4H), 7.86(d, 2H), 7.82(d, 2H), 7.78(d, 2H), 7.48(d, 4H), 7.33-7.31(m, 8H), 7.22(m, 2H) |
| 2A | $C_{56}H_{32}N_2S_2$ M+ 796.20 | 8.81(s, 2H), 8.55(d, 2H), 8.31(s, 2H), 8.13-8.12(m, 4H), 7.97(d, 2H), 7.86(d, 2H), 7.82(d, 2H), 7.78(d, 2H), 7.54(d, 8H), 7.44(m, 2H), 7.33-7.31(m, 4H) |
| 3A | $C_{54}H_{36}N_4S_2$ M+ 798.19 | 8.84 (s, 4H), 8.31(s, 2H), 8.13-8.12(m, 4H), 7.86-7.78(m, 6H), 7.48(d, 4H), 7.33-7.31(m, 8H), 7.22(t, 2H) |
| 4A | $C_{43}H_{36}O_2S_2$ M+ 702.17 | 8.31(s, 2H), 8.13-8.12(m, 4H), 7.86-7.78(m, 6H), 7.37(d, 4H), 7.33-7.32(m, 4H), 6.83(d, 4H), 3.73(s, 6H) |
| 5A | $C_{52}H_{23}N_2S_2$ M+ 744.17 | 9.11(s, 2H), 8.67(s ,2H), 8.31(s, 2H), 8.13-8.12(m, 4H), 7.87-7.86(m, 4H), 7.82(d, 2H), 7.78(d, 2H), 7.71(d, 2H), 7.57-7.50(m, 4H), 7.33-7.31(m, 4H) |
| 6A | $C_{44}H_{24}N_2S_2$ M+ 644.14 | 8.81(s, 2H), 8.55(d, 2H), 8.31(s, 2H), 8.13-8.12(m, 4H), 7.97(d, 2H), 7.86-7.78(m, 6H), 7.44(m, 2H), 7.33-7.31(m, 4H) |
| 7A | $C_{50}H_{28}S_4$ M+ 754.09 | 8.31(s, 2H), 8.13-8.12(m, 4H), 7.86-7.80(m, 10H), 7.40(s, 2H), 7.33-7.30(m, 8H) |
| 8A | $C_{70}H_{40}N_2S_2$ M+ 972.26 | 8.31(s, 2H), 8.13-8.12(m, 4H), 7.86-7.77(m, 8H), 7.77-7.30(m, 22H), 7.08-7.00(m, 4H) |
| 9A | $C_{70}H_{40}N_2S_2$ M+ 972.26 | 8.31(s, 2H), 8.13-8.12(m, 4H), 7.86-7.77(m, 8H), 7.77-7.30(m, 22H), 7.08-7.00(m, 4H) |
| 10A | $C_{70}H_{44}N_2S_2$ M+ 976.29 | 8.31(s, 2H), 8.13-8.12(m, 4H), 7.86-7.78(m, 6H), 7.33-7.31(m, 4H), 7.23(d, 4H), 7.01(m, 8H), 6.62(m, 4H), 6.52-6.46(m, 12H) |

TABLE 4

| number | LC-MS | NMR |
|---|---|---|
| 11A | $C_{53}H_{30}O_2S_2$ M+ 822.17 | 8.31(s, 2H), 8.13-8.12(m, 4H), 7.86-7.71(m, 8H), 7.49-7.31(m, 12H), 7.19-7.13(m, 4H) |
| 12A | $C_{53}H_{30}O_2S_2$ M+ 822.17 | 8.31(s, 2H), 8.13-8.12(m, 4H), 7.86-7.78(m, 6H), 7.49-7(m, 12H), 7.19-13(m, 6H) |
| 13A | $C_{53}H_{30}S_4$ M+ 854.12 | 8.31(s, 2H), 8.13-8.12(m, 4H), 8.0-7.78(m, 14H), 7.53(d, 2H), 7.33-7.31(m, 8H) |
| 14A | $C_{53}H_{30}S_4$ M+ 854.12 | 8.31(s, 2H), 8.13-8.12(m, 4H), 7.86-7.74(m,12H), 7.53(d, 2H), 7.39-7.31(m, 10H) |
| 1B | $C_{48}H_{28}O_2$ M+ 610.19 | 8.31(s, 2H), 8.13-8.12(m, 4H), 7.82(d, 2H), 7.49-7.13(m, 18H) |
| 2B | $C_{58}H_{32}N_2O_2$ M+ 764.25 | 8.81(s, 2H), 8.55(d, 2H), 8.31(s, 2H), 8.13-8.12(m, 4H), 7.97(d, 2H), 7.82(d, 2H) 7.54-7.42 (m, 14H), 7.19-7.13(m, 4H) |

TABLE 4-continued

| number | LC-MS | NMR |
|---|---|---|
| 3B | $C_{54}H_{30}N_4O_2$ M+ 766.24 | 8.84(s, 4H), 8.31(s, 2H), 8.13-8.12(m, 4H), 7.82(d, 2H), 7.49-7.13(m, 18H) |
| 4B | $C_{48}H_{30}O_4$ M+ 670.21 | 8.31(s, 2H), 8.13-8.12(m, 4H), 7.82(d, 2H), 7.49-7.13(m, 12H), 6.83(d, 4H), 3.73(s, 6H) |
| 5B | $C_{52}H_{23}N_2O_2$ M+ 712.22 | 9.11(s, 2H), 8.67(s, 2H), 8.31(s, 2H), 8.13-8.12(m, 4H), 7.87-7.13(m, 18H) |
| 6B | $C_{44}H_{24}N_2O_2$ M+ 612.18 | 8.81(s, 2H), 8.55(d, 2H), 8.31(s, 2H), 8.13-8.12(m, 4H), 7.97(d, 2H), 7.82(d, 2H), 7.49-7.42(m, 6H), 7.19-7.13(m, 4H) |

TABLE 5

| number | LC-MS | NMR |
|---|---|---|
| 7B | $C_{50}H_{26}O_2S_2$ M+ 722.14 | 8.31(s, 2H), 8.13-8.12(m, 4H), 7.92-7.8(m, 6H), 7.49-7.13(m, 14H) |
| 8B | $C_{70}H_{40}N_2O_2$ M+ 940.31 | 8.31(s, 2H), 8.13-8.12(m, 4H), 8.22-8.17(m, 4H), 7.55-7.00(m, 30H) |
| 9B | $C_{70}H_{40}N_2O_2$ M+ 940.31 | 8.31(s, 2H), 8.13-8.12(m, 4H), 7.82(d, 2H), 7.55-7.00(m, 32H) |
| 10B | $C_{70}H_{44}N_2O_2$ M+ 944.34 | 8.31(s, 2H), 8.13-8.12(m, 4H), 7.82(d, 2H), 7.49-7.42(m, 4H), 7.23-7.01(m, 16H), 6.62-6.46(m, 16H) |
| 11B | $C_{58}H_{30}O_4$ M+ 790.21 | 8.31(s, 2H), 8.13-8.12(m, 4H), 7.82(d, 2H), 7.71(s, 2H), 7.49-7.42(m, 12H), 7.19-7.13(m, 8H) |
| 12B | $C_{58}H_{30}O_4$ M+ 790.21 | 8.31(s, 2H), 8.13-8.12(m, 4H), 7.82(d, 2H), 7.49-7.42(m, 8H) 7.19-7.13(m, 14H) |
| 13B | $C_{58}H_{30}O_2S_2$ M+ 822.17 | 8.31(s, 2H), 8.13-7.78(m, 14H), 7.53-7.13(m, 14H) |
| 14B | $C_{58}H_{30}O_2S_2$ M+ 822.17 | 8.31(s, 2H), 8.13-8.12(m, 4H), 7.82-7.74(m, 8H), 7.53-7.13(m, 16H) |
| 1C | $C_{35}H_{28}N_4$ M+ 538.22 | 8.31(s, 2H), 8.13-8.12(m, 4H), 8.00(s, 2H), 7.82(d, 2H), 7.48-7.32(m, 10H), 3.80(s, 6H) |
| 2C | $C_{48}H_{32}N_6$ M+ 692.27 | 8.81(s, 2H), 8.55(d, 2H), 8.31(s, 2H), 8.13-8.12(m, 4H), 8.01-7.96(m, 4H), 7.82(d, 2H), 7.54-7.44(m, 10H), 3.80(s, 6H) |

TABLE 6

| number | LC-MS | NMR |
|---|---|---|
| 3C | $C_{46}H_{30}N_3$ M+ 694.26 | 8.84(s, 4H), 8.31(s, 2H), 8.13-8.12(m, 4H), 8.00(s, 2H), 7.82(d, 2H), 7.48-7.32(m, 10H), 3.80(s, 6H) |
| 4C | $C_{40}H_{30}N_4O_2$ M+ 598.24 | 8.31(s, 2H), 8.13-8.12(m, 4H), 8.00(s, 2H), 7.82(d, 2H), 7.37(d, 4H), 6.83(d, 4H), 3.80(s, 6H), 3.73(s, 6H) |
| 5C | $C_{44}H_{23}N_6$ M+ 670.24 | 9.11(s, 2H), 8.67(s, 2H), 8.31(s, 2H), 8.13-8.12(m, 4H), 8.00-7.82(m, 6H), 7.71(d, 2H), 7.57-7.50(m, 4H), 3.80(s, 6H) |
| 6C | $C_{36}H_{24}N_6$ M+ 540.21 | 8.81(s, 2H), 8.55(d, 2H), 8.31(s, 2H), 8.13-8.12(m, 4H), 8.00-7.97(m, 4H), 7.82(d, 2H), 7.44((m, 2H), 3.80(s, 6H) |
| 7C | $C_{42}H_{26}N_4S_2$ M+ 650.16 | 8.31(s, 2H), 8.13-8.12(m, 4H), 8.00(s, 2H), 7.91-7.80(m, 6H), 7.40-7.31(m, 6H), 3.80(s, 6H) |
| 8C | $C_{62}H_{40}N_6$ M+ 868.33 | 8.31(s, 2H), 8.13-8.12(m, 4H), 8.00(s, 2H), 7.82-7.77(m, 4H), 7.55-7.30(m,18H), 7.08-7.00(m, 4H), 3.80(s, 6H) |
| 9C | $C_{62}H_{44}N_6$ M+ 868.33 | 8.31(s, 2H), 8.13-8.12(m, 4H), 8.00(s, 2H), 7.82(d, 2H), 7.55-7.30(m, 18H), 7.08-7.00(m, 6H), 3.80(s, 6H) |
| 10C | $C_{62}H_{44}N_6$ M+ 872.36 | 8.31(s, 2H), 8.13-8.12(m, 4H), 8.00(s, 2H), 7.82(d, 2H), 7.23(d, 4H), 7.01(m, 8H), 6.62-6.46(m, 16H), 3.80(s, 6H) |
| 11C | $C_{50}H_{30}N_4O_2$ M+ 718.24 | 8.31(s, 2H), 8.13-8.12(m, 4H), 8.00(s, 2H), 7.82(d, 2H), 7.71(s, 2H), 7.49-7.41(m, 8H), 7.19-7.13(m, 4H), 3.80(s, 6H) |
| 12C | $C_{50}H_{30}N_4O_2$ M+ 718.24 | 8.31(s, 2H), 8.13-8.12(m, 4H), 8.00(s, 2H), 7.82(d, 2H), 7.45-7.41(m, 8H), 7.19-7.13(m, 6H), 3.80(s, 6H) |

TABLE 7

| number | LC-MS | NMR |
|---|---|---|
| 13C | $C_{58}H_{30}N_4S_2$ M+ 718,24 | 8.31(s, 2H), 8.13-8.12(m, 4H), 8.00(s, 4H), 7.92-7.78(m, 8H), 7.53(d, 2H), 7.33-7.31(m,4H) 3.80(s, 6H) |
| 14C | $C_{40}H_{30}N_4O_2$ M+ 598.24 | 8.31(s, 2H) 8.13-8.12(m, 4H), 8.00(s, 2H) 7.86-7.74(m, 8H), 7.53(d, 2H), 7.39-7.31(m, 6H) 3.80(s, 6H) |
| 1Da | $C_{53}H_{30}N_2$ M+ 760.29 | 8.93(s, 2H), 8.31(s, 2H), 8.13-8.12(m, 4H), 7.55-7.00(m, 28H) |
| 2Da | $C_{63}H_{42}N_4$ M+ 914.34 | 8.93(s, 2H), 8.81(s, 2H), 8.55(d, 2H), 8.31(s, 2H), 8.13-8.12(m, 4H), 7.97(s, 2H), 7.54-7.00 (m, 28H) |

TABLE 7-continued

| number | LC-MS | NMR |
| --- | --- | --- |
| 3Da | $C_{68}H_{40}N_6$ M+ 916.33 | 8.93(s, 2H), 8.84(s, 4H), 8.31(s, 2H), 8.13-8.12(m, 4H), 7.54-7.00(m, 28H) |
| 4Da | $C_{86}H_{40}N_2O_2$ M+ 820.31 | 8.93(s, 2H), 8.31(s, 2H), 8.13-8.12(m, 4H), 7.55-6.83(m, 26H), 3.80(s, 6H) |
| 5Da | $C_{64}H_{34}N_4$ M+ 862.31 | 9.11(s, 2H), 8.93(s, 2H), 8.67(s, 2H), 8.31(s, 2H), 8.13-8.12(m, 4H), 7.87-7.00(m, 26H) |
| 6Da | $C_{56}H_{34}N_4$ M+ 762.28 | 8.93(s, 2H), 8.81(s, 2H), 8.55(d, 2H), 8.31(s, 2H), 8.13-8.12(m, 4H), 7.97(d, 2H), 7.55-7.00(m, 20H) |
| 7Da | $C_{62}H_{36}N_2S_2$ M+ 872.23 | 8.93(s, 2H), 8.31(s, 2H), 8.13-8.12(m, 4H), 7.90-7.80(m, 4H), 7.55-7.00(24H) |
| 8Da | $C_{32}H_{30}N_4$ M+ 1090.40 | 8.93(s, 2H), 8.31(s, 2H), 8.13-8.12(m, 4H), 7.77(s, 2H), 7.55-7.00(m, 40H) |

TABLE 8

| number | LC-MS | NMR |
| --- | --- | --- |
| 9Da | $C_{82}H_{50}N_4$ M+ 1090.40 | 8.93(s, 2H), 8.31(s, 2H), 8.13-8.12(m, 4H), 7.77(s, 2H), 7.55-7.00(m, 40H) |
| 10Da | $C_{82}H_{54}N_4$ M+ 1090.43 | 8.93(s, 2H), 8.31(s, 2H), 8.13-8.12(m, 4H), 7.55-7.00(m, 3H), 6.62-6.46(m, 16H) |
| 11Da | $C_{70}H_{40}N_2O_2$ M+ 940.31 | 8.93(s, 2H), 8.31(s, 2H), 8.13-8.12(m, 4H), 7.71(s, 2H), 7.55-7.00(m, 30H) |
| 12Da | $C_{70}H_{40}N_2O_2$ M+ 940.31 | 8.93(s, 2H), 8.31(s, 2H), 8.13-8.12(m, 4H), 7.71(s, 2H), 7.55-7.00(m, 30H) |
| 13Da | $C_{70}H_{40}N_2O_2$ M+ 972.26 | 8.93(s, 2H), 8.31(s, 2H), 8.13-8.12(m, 4H), 8.00-7.78(m, 8H), 7.55-7.00(m, 24H) |
| 14Da | $C_{70}H_{40}N_2S_2$ M+ 972.26 | 8.93(s, 2H), 8.31(s, 2H), 8.13-8.12(m, 4H), 7.86-7.74(m, 6H), 7.55-7.00(m, 26H) |
| 1Db | $C_{58}H_{86}N_2$ M+ 760.29 | 8.93(s, 2H), 8.31(s, 2H), 8.13(s, 2H), 7.88(d, 2H), 7.55-7.00(m, 28H) |
| 2Db | $C_{63}H_{42}N_4$ M+ 914.34 | 8.93(d, 2H), 8.81(s, 2H), 8.55(d, 2H), 8.13(s, 2H), 7.97(d, 2H), 7.88(d, 2H), 7.55-7.00(m, 30H) |
| 3Db | $C_{66}H_{40}N_6$ M+ 916.33 | 8.93(d, 2H), 8.84(s, 4H), 8.31(s, 2H), 8.13(s, 2H), 7.88(d, 2H), 7.55-7.00(m, 28H) |
| 4Db | $C_{80}H_{40}N_2O_2$ M+ 820.31 | 8.93(d, 2H), 8.31(s, 2H), 8.13(s, 2H), 7.88(d, 2H), 7.55-6.83(m, 26H), 3.73(s, 6H) |

TABLE 9

| number | LC-MS | NMR |
| --- | --- | --- |
| 5Db | $C_{64}H_{53}N_4$ M+ 862.31 | 9.11(s, 2H), 8.93(d, 2H), 8.67(s, 2H), 8.31(s, 2H), 8.13(s, 2H), 7.88-7.00(m, 28H) |
| 6Db | $C_{56}H_{34}N_4$ M+ 762.28 | 8.93(d, 2H), 8.81(s, 2H), 8.55(d, 2H), 8.31(s, 2H), 8.13(s, 2H), 7.97(d, 2H), 7.88(d, 2H), 7.55-7.00(m, 20H) |
| 7Db | $C_{62}H_{36}N_2S_2$ M+872.23 | 8.93(d, 2H), 8.31(s, 2H), 8.13(s, 2H), 7.90-7.80(m, 6H), 7.55-7.00(m, 24H) |
| 8Db | $C_{82}H_{50}N_4$ M+ 1090.40 | 8.93(d, 2H), 8.31(s, 2H), 8.13(s, 2H), 7.88(d, 2H), 7.77(s, 2H), 7.55-7.00(40H) |
| 9Db | $C_{82}H_{56}N_4$ M+ 1090.40 | 8.93(d, 2H), 8.31(s, 2H), 8.13(s, 2H), 7.88(d, 2H), 7.55-7.00(42H) |
| 10Db | $C_{82}H_{54}N_4$ M+ 1094.43 | 8.93(d, 2H), 8.31(s, 2H), 8.13(s, 2H), 7.88(d, 2H), 7.55-7.00(m, 30H), 6.62-6.46(m, 16H) |
| 11Db | $C_{70}H_{40}N_2O_2$ M+ 940.31 | 8.93(d, 2H), 8.31(s, 2H), 8.13(s, 2H), 7.88(d, 2H), 7.71(s, 2H), 7.55-7.00(m, 30H) |
| 12Db | $C_{70}H_{40}N_2O_2$ M+ 940.31 | 8.93(d, 2H), 8.31(s, 2H), 8.13(s, 2H), 7.88(d, 2H), 7.55-7.00(m, 32H) |
| 13Db | $C_{70}H_{40}N_2S_2$ M+ 972.26 | 8.93(d, 2H), 8.31(s, 2H), 8.13(s, 2H), 8.00-7.78(m, 10H), 7.55-7.00(m, 24H) |
| 14Db | $C_{70}H_{40}N_2S_2$ M+ 972.26 | 8.93(d, 2H), 8.31(s, 2H), 8.13(s, 2H), 7.88-7.74(m, 4H), 7.55-7.00(m, 30H) |

TABLE 10

| number | LC-MS | NMR |
| --- | --- | --- |
| 1Ea | $C_{46}H_{26}O2$ M+ 610.19 | 8.93(s, 2H), 8.31(s, 2H), 8.13-8.12(d, 4H), 7.55-7.13(m, 20H) |

TABLE 10-continued

| number | LC-MS | NMR |
|---|---|---|
| 2Ea | $C_{56}H_{32}N_2O_2$<br>M+ 764.25 | 8.93(s, 2H), 8.81(s, 2H), 8.55(d, 2H), 8.31(s, 2H), 8.13-8.12(d, 4H), 7.97(d, 2H), 7.54-7.42(m, 14H), 7.19-7.13(m, 4H) |
| 3Ea | $C_{54}H_{30}N_4O_2$<br>M+766.24 | 8.93(s, 2H), 8.84(s, 4H), 8.31(s, 2H), 8.13-8.12(d, 4H), 7.48-7.13(m, 18H) |
| 4Ea | $C_{43}H_{50}N_4$<br>M+ 670.21 | 8.93(s, 2H), 8.31(s, 2H), 8.13-8.12(d, 4H), 7.49-7.13(m, 12H), 6.83(d, 4H), 3.73(s, 6H) |
| 5Ea | $C_{52}H_{23}N_2O_2$<br>M+ 712.22 | 9.11(s, 2H), 8.93(s, 2H), 8.67(s, 2H), 8.31(s, 2H), 8.13-8.12(d, 4H), 7.87(d, 2H), 7.71(d, 2H), 7.57-7.42(m, 8H), 7.19-7.13(m, 4H) |
| 6Ea | $C_{44}H_{24}N_2O_2$<br>M+ 612.18 | 8.93(s, 2H), 8.81(s, 2H), 8.55(d, 2H), 8.31(s, 2H), 8.13-8.12(d, 4H), 7.97(d, 2H) 7.49-7.42(m, 6H), 7.19-7.13(m, 4H) |
| 7Ea | $C_{50}H_{26}O_2S_2$<br>M+ 722.14 | 8.93(s, 2H), 8.31(s, 2H), 8.13-8.12(d, 4H), 7.90-7.80(m, 4H), 7.49-7.13(m, 14H) |
| 8Ea | $C_{70}H_{40}N_2O_2$<br>M+ 940.31 | 8.93(s, 2H), 8.31(s, 2H), 8.13-8.12(d, 4H), 7.77(s, 2H), 7.55-7.00(m, 30H) |
| 9Ea | $C_{70}H_{40}N_2O_2$<br>M+ 940.31 | 8.93(s, 2H), 8.31(s, 2H), 8.13-8.12(d, 4H), 7.55-7.00(m, 30H) |
| 10Ea | $C_{70}H_{44}N_2O_2$<br>M+ 944.34 | 8.93(s, 2H), 8.31(s, 2H), 8.13-8.12(d, 4H), 7.49-7.01(m, 20H), 6.62-6.46(m, 16H) |

TABLE 11

| number | LC-MS | NMR |
|---|---|---|
| 11Ea | $C_{58}H_{30}O_4$<br>M+ 790.21 | 8.93(s, 2H), 8.31(s, 2H), 8.13-8.12(d, 4H), 7.71(s, 2H), 7.49-7.13(m, 20 H) |
| 12Ea | $C_{58}H_{30}O_4$<br>M+ 790.21 | 8.93(s, 2H), 8.31(s, 2H), 8.13-8,12(d, 4H), 7.49-7.13(m, 20 H) |
| 13Ea | $C_{58}H_{30}O_2S_2$<br>M+ 822.17 | 8.93(s, 2H), 8.31(s, 2H), 8.13-7.78(m, 12H), 7.53-7.13(m, 14H) |
| 14Ea | $C_{58}H_{30}O_2S_2$<br>M+ 822.17 | 8.93(s, 2H), 8.31(s, 2H), 8.13-8.12(d, 4H), 7.86-7.74(m, 6H), 7.53-7.13(m, 16H) |
| 1Eb | $C_{46}H_{26}O_2$<br>M+ 610.19 | 8.93(s, 2H), 8.31(s, 2H), 8.13(s, 21), 7.88(d, 2H), 7.49-7.13(m, 18H) |
| 2Eb | $C_{56}H_{32}N_2O_2$<br>M+ 764.25 | 8.93(s, 2H), 8.81(s, 2H), 8.55(d, 2H), 8.31(s, 2H), 8.13 (s, 2H), 7.97-88(m, 4H), 7.54-7.13 (m, 18H) |
| 3Eb | $C_{34}H_{30}O_4S_2$<br>M+ 766.24 | 8.91(s, 2H), 8.84(s, 4H), 8.31(s, 2H), 8.13(s, 2H), 7.88(d, 2H), 7.49-7.13(m, 18H) |
| 4Eb | $C_{48}H_{30}N_4$<br>M+ 670.21 | 8.91(s, 2H), 8.31(s, 2H), 8.13(s, 2H), 7.88(d, 2H), 7.49-7.13(m, 12H), 6.83(d, 4H), 3.73(s, 6H) |
| 5Eb | $C_{52}H_{22}N_2O_2$<br>M+ 712.22 | 9.11(s, 2H), 8.93(s, 2H), 8.67(s, 2H), 8.31(s, 2H), 8.13(s, 2H), 7.87-7.42(m, 14H), 7.19-7.13 (m, 4H) |
| 6Eb | $C_{44}H_{24}N_2O_2$<br>M+ 612.18 | 8.93(s, 2H), 8.81(s, 2H), 8.55(d, 2H), 8.31(s, 2H), 8.13 (s, 2H), 7.97-7.88(m, 4H), 7.49-7.13 (m, 10H) |

TABLE 12

| number | LC-MS | NMR |
|---|---|---|
| 7Eb | $C_{50}H_{26}O_2S_2$<br>M+ 722.14 | 8.93(d, 2H), 8.31(s, 2H), 8.13(s, 2H), 7.90-7.80(m, 61), 7.49-7.13(m, 14H) |
| 8Eb | $C_{70}H_{40}N_2O_2$<br>M+ 940.31 | 8.93(d, 2H), 8.31(s, 2H), 8.13(s, 2H), 7.88(d, 2H), 7.77(s, 2H), 7.55-7.00(m, 30H) |
| 9Eb | $C_{70}H_{40}N_2O_2$<br>M+ 940.31 | 8.93(d, 2H), 8.31(s, 2H), 8.13(s, 2H), 7.88(d, 2H), 7.55-7.00(m, 30H) |
| 10Eb | $C_{70}H_{44}N_2O_2$<br>M+ 944.34 | 8.93(d, 2H), 8.31(s, 2H), 8.13(s, 2H), 7.88(d, 2H), 7.49-7.01(m, 20H), 6.62-6.46(m, 16H) |
| 11Eb | $C_{53}H_{30}O_4$<br>M+ 790.21 | 8.93(d, 2H), 8.31(s, 2H), 8.13(s, 2H), 7.88(d, 2H), 7.71(s, 2H), 7.49-7.13(m, 20H) |
| 12Eb | $C_{58}H_{30}O_4$<br>M+ 790.21 | 8.93(d, 2H), 8.31(s, 2H), 8.13(s, 2H), 7.88(d, 2H), 7.49-7.13(m, 22H) |
| 13Eb | $C_{58}H_{30}O_2S_2$<br>M+ 822.17 | 8.93(d, 2H), 8.31(s, 21), 8.13(s, 2H), 8.00-7.78(m, 10H), 7.53-7.13(m, 14H) |
| 14Eb | $C_{52}H_{30}O_2S_2$<br>M+ 822.17 | 8.93(d, 2H), 8.31(s, 2H), 8.13(s, 2H), 7.88-7.74(m, 8H), 7.53-7.13(m, 16H) |
| 1Fa | $C_{46}H_{28}S_2$<br>M+ 642.15 | 8.93(s, 2H), 8.31(s, 2H), 8.13-8.12(d, 4H), 7.86-7.78(m, 4H), 7.48-7.22(m, 14H) |

TABLE 12-continued

| number | LC-MS | NMR |
|---|---|---|
| 2Fa | $C_{56}H_{32}N_2O_2$ M+ 796.20 | 8.93(s, 2H), 8.81(s, 2H), 8.55(d, 2H), 8.31(s, 2H), 8.13-8.12(d, 4H), 7.97-7.78(m, 6H), 7.54-7.31(m, 14H) |

TABLE 13

| number | LC-MS | NMR |
|---|---|---|
| 3Fa | $C_{54}H_{30}N_4O_2$ M+ 798.19 | 8.93(s, 2H), 8.84(s, 4H), 8.31(9, 2H), 8.13-8.12(d, 4H), 7.86-7.78(m, 4H), 7.48-7.22(m, 14H) |
| 4Fa | $C_{43}H_{30}O_2S_2$ M+ 702.17 | 8.93(s, 2H), 8.31(s, 2H), 8.13-8.12(d, 4H), 7.86-7.78(m, 4H), 7.37-7.31(s, 8H), 6.83(d, 4H), 3.73(s, 6H) |
| 5Fa | $C_{52}H_{28}N_2S_2$ M+ 744.17 | 9.11(s, 2H), 8.93(s, 2H), 8.67(s, 2H), 8.31(s, 2H), 8.13-8.12(d, 4H), 7.86-7.31(m, 16H) |
| 6Fa | $C_{44}H_{24}N_2S_2$ M+ 644.14 | 8.93(s, 2H), 8.81(s, 2H), 8.55(d, 2H), 8.31(s, 2H), 8.13-8.12(d, 4H), 7.97-7.78(m, 6H), 7.44-7.31(m, 6H) |
| 7Fa | $C_{50}H_{26}S_4$ M+ 754.09 | 8.93(s, 2H), 8.31(s, 2H), 8.13-8.12(d, 4H), 7.86-7.80(m, 8H), 7.40-7.31(m, 10H) |
| 8Fa | $C_{70}H_{40}N_2S_2$ M+ 972.26 | 8.93(s, 2H), 8.31(s, 2H), 8.13-8.12(d, 4H), 7.86-7.77(m, 6H), 7.55-7.00(m, 26H) |
| 9Fa | $C_{70}H_{40}N_2S_2$ M+ 972.26 | 8.93(s, 2H), 8.31(s, 2H), 8.13-8.12(d, 4H), 7.86-7.77(m, 6H), 7.55-7.00(m, 26H) |
| 10Fa | $C_{70}H_{44}N_2S_2$ M+ 976.29 | 8.93(s, 2H), 8.31(s, 2H), 8.13-8.12(d, 4H), 7.86-7.78(m, 4H), 7.33-7.01(m, 16H), 6.62-6.46(m, 16H) |
| 11Fa | $C_{52}H_{30}O_2S_2$ M+ 822.17 | 8.93(s, 2H), 8.31(s, 2H), 8.13-8.12(d, 4H), 7.86-7.71(m, 4H), 7.48-7.13(m, 18H) |
| 12Fa | $C_{53}H_{30}O_2S_2$ M+ 822.17 | 8.93(s, 2H), 8.31(s, 2H), 8.13-8.12(d, 4H), 7.86-7.78(m, 4H), 7.49-7.13(m, 18H) |

TABLE 14

| number | LC-MS | NMR |
|---|---|---|
| 13Fa | $C_{58}H_{30}N_4$ M+ 854.12 | 8.93(s, 2H), 8.31(s, 2H), 8.13-8.12(d, 4H), 8.00-7.78(m, 12H), 7.53-7.31(m, 10H) |
| 14Fa | $C_{58}H_{30}N_4$ M+ 854.12 | 8.93(s, 2H), 8.31(s, 2H), 8.13-8.12(d, 4H), 7.86-7.74(m, 10H), 7.53-7.31(m, 12H) |
| 1Fb | $C_{46}H_{26}S_2$ M+ 642.15 | 8.93(d, 2H), 8.31(s, 2H), 8.13(s, 2H), 7.88-7.78(m, 6H), 7.48-7.22(m, 14H) |
| 2Fb | $C_{36}H_{32}N_2S_2$ M+ 796.20 | 8.93(d 2H), 8.81(s, 2H), 8.55(d, 2H), 8.31(s, 2H), 8.13(s, 2H) 7.97-7.78(m, 8H) 7.54-7.31(m, 14H) |
| 3Fb | $C_{54}H_{38}N_4S_2$ M+ 798.97 | 8.93(d, 2H), 8.84(s, 2H), 8.31(s, 2H), 8.13(s, 2H), 7.86-7.78(m, 6H), 7.48-7.22(m, 16H) |
| 4Fb | $C_{48}H_{30}O_2S_2$ M+702.17 | 8.93(d, 2H) 8.31(s, 2H), 8.13(s, 2H) 7.88-7.78(m, 6H), 7.37-7.31(m, 8H), 6.83(d, 4H) 3.73(s, 6H) |
| 5F | $C_{52}H_{23}N_2S_2$ M+ 744.17 | 9.11(s, 2H), 8.93(d, 2H), 8.67(s, 2H), 8.31(s, 2H), 8.13(s, 2H), 7.87-7.31(m, 18H) |
| 6Fb | $C_{44}H_{24}N_2S_2$ M+ 644.14 | 8.93(d, 2H) 8.81(s, 2H), 8.55(d, 2H) 8.31(s, 2H), 8.13(s, 2H), 7.97-7.78(m, 8H), 7.44-7.31(m, 6H) |
| 7Fb | $C_{50}H_{28}S_4$ M+ 754.09 | 8.93(d, 2H), 8.31(s, 2H), 8.13(s, 2H), 7.90-7.78(m, 10H), 7.40-7.30(m, 10H) |
| 8Fb | $C_{70}H_{40}N_2S_2$ M+ 972.26 | 8.93(d, 2H), 8.31(s, 2H), 8.13(s, 2H), 7.86-7.78(m, 8H), 7.55-7.00(m, 26H) |

TABLE 15

| number | LC-MS | NMR |
|---|---|---|
| 9Fb | $C_{70}H_{40}N_2S_2$ M+ 972.26 | 8.93(d,. 2H), 8.31(s, 2H), 8.13(s, 2H), 7.86-7.78(m, 8H), 7.55-7.00(m, 26H) |
| 10Fb | $C_{70}H_{44}N_2S_2$ M+ 976.29 | 8.93(d, 2H), 8.31(s, 2H), 8.13(s, 2H), 7.86-7.78(m, 6H), 7.31-7.01(m, 16H), 6.62-6.46(m, 16H) |
| 11Fb | $C_{58}H_{30}O_2S_2$ M+ 822.17 | 8.93(d, 2H), 8.31(s, 2H), 8.13(s, 2H), 7.88-7.71(m, 8H), 7.49-7.13(m, 16H) |
| 12Fb | $C_{58}H_{30}O_2S_2$ M+ 822.17 | 8.93(d, 2H), 8.31(s, 2H), 8.13(s, 2H), 7.86-7.74(m, 12H), 7.53-7.31(m, 12H) |
| 13Fb | $C_{58}H_{30}S_4$ M+ 854.12 | 8.93(d, 2H), 8.31(s, 2H), 8.13(s, 2H), 8.00-7.78(14H), 7.53(d, 2H), 7.33-7.31(m, 8H) |
| 14Fb | $C_{58}H_{30}S_4$ M+ 854.12 | 8.93(d, 2H), 8.31(s, 2H), 8.13(s, 2H), 7.86-7.78(m, 6H), 7.49-7.13(m, 18H) |
| 1Ga | $C_{52}H_{38}$ M+ 662.30 | 8.86(s, 2H), 8.31-8.26(d, 4H), 8.13-8.06(m, 4H), 7.61-7.22(m,,16H), 1.80(s, 12H) |

TABLE 15-continued

| number | LC-MS | NMR |
|---|---|---|
| 2Ga | $C_{62}H_{44}N_2$ M+ 816.35 | 8.86(s, 2H), 8.81(s, 2H), 8.55(d, 2H), 8.31-8.26(d, 4H), 8.13-8.06(m, 4H), 7.97(d, 2H), 7.61-7.24(m, 16H), 1.80(s, 12H) |
| 3Ga | $C_{80}H_{42}N_4$ M+ 818.34 | 8.86-8,84(d, 6H), 8.31-8.26(d, 4H), 8.13-8.06(m, 4H), 7.61-7.22(m, 16H), 1.80(s, 12H) |
| 4Ga | $C_{54}H_{42}O_2$ M+ 722.32 | 8.86(s, 2H), 8.31-8.26(d, 4H), 8.13-8.06(m, 4H), 7.61-7.24(m, 10H), 6.83(d, 4H), 3.73(s, 6H), 1.80(s, 12H) |

TABLE 16

| number | LC-MS | NMR |
|---|---|---|
| 5Ga | $C_{58}H_{40}N_2$ M+ 764.32 | 9.11(s, 2H), 8.86(s, 2H), 8.67(s, 2H), 8.31(s, 2H), 8.26(s, 2H), 8.13-8.06(m, 4H), 7.87-7.24(m, 14H), 1.80(s, 12H) |
| 6Ga | $C_{50}H_{36}N_2$ M+ 664.29 | 8.86(s, 2H), 8.81(s, 2H), 8.55(d, 2H), 8.31-8.26(d, 4H), 8.13-8.06(m, 4H), 7.97(d, 2H), 7.61(d, 2H), 7.44-7.24(m, 6H), 1.80(s, 12H) |
| 7Ga | $C_{56}H_{38}S_2$ M+ 774.24 | 8.86(s, 2H), 8.31-8.26(d, 4H), 8.13-8.06(m, 4H), 7.90-7.80(m, 4H), 7.61(d, 2H), 7.44-7.24(m, 10H), 1.80(s, 12H) |
| 8Ga | $C_{76}H_{32}N_2$ M+ 992.41 | 8.86(s, 2H), 8.31-8.26(d, 4H), 8.13-8.06(m, 4H), 7.77-7.00(m, 30H), 1.80(s, 12H) |
| 9Ga | $C_{76}H_{36}N_2$ M+ 992.41 | 8.86(s, 2H), 8.31-8.26(d, 4H), 8.13-8.06(m, 4H), 7.77-7.00(m, 30H), 1.80(s, 12H) |
| 10Ga | $C_{76}H_{36}N_2$ M+ 996.44 | 8.86(s, 2H), 8.31-8.26(d, 4H), 8.13-8.06(m, 4H), 7.61-7.01(m, 16H), 6.62-6.46(m, 16H), 1.780(s, 12H) |
| 11Ga | $C_{64}H_{42}N_2$ M+ 842.32 | 8 86(s, 2H), 8.31-8.26(d, 4H), 8.13-8.06(m, 4H), 7.71(s, 2H), 7.61-7.13(m, 18H), 1.80(s, 12H) |
| 12Ga | $C_{64}H_{42}N_2$ M+842.32 | 8.86(s, 2H), 8.31-8.26(d, 4H), 8.13-8.06(m, 4H), 7.71-7.13(m, 20H), 1.80(s, 12H) |
| 13Ga | $C_{84}H_{42}S_2$ M+ 874.27 | 8.86(s, 2H), 8.31-8.26(d, 4H), 8.31-7.24(m, 24H), 1.80(s, 12H) |
| 14Ga | $C_{64}H_{42}S_2$ M+ 874.27 | 8.86(s, 4H), 8.31-8.26(d, 4H), 8.13-8.06(m, 4H), 7.86-7.24(m, 2H), 1.80(s, 12H) |

TABLE 17

| number | LC-MS | NMR |
|---|---|---|
| 1Gb | $C_{58}H_{39}$ M+ 662.30 | 8.81(d, 2H), 8.31(s, 2H), 8.13-8.02(m, 6H), 7.61-7.22(m, 16H), 1.80(s, 12H) |
| 2Gb | $C_{62}H_{44}N_2$ M+ 816.35 | 8.81(m, 4H), 8.55(d, 2H), 8.31(s, 2H), 8.13-7.97(m, 6H), 7.61-7.24(m, 16H), 1.80(s, 12H) |
| 3Gb | $C_{60}H_{42}N_4$ M+ 818.34 | 8.84-8.81(m, 6H), 8.31(s, 2H), 8.13-8.02(m, 6H), 7.61-7.22(m, 16H), 1.80(s, 12H) |
| 4G6 | $C_{54}H_{42}O_2$ M+ 722.32 | 8.81(d, 2H), 8.31(s, 2H), 8.13-8.02(m, 6H), 7.61-7.24(m, 10H), 6.83(d, 4H), 3.73(s, 6H), 1.80(s, 12H) |
| 5Gb | $C_{38}H_{40}N_2$ M+ 764.32 | 9.11(s, 2H), 8.81(d, 2H), 8.67(s, 2H), 8.31(s, 2H), 8.13-7.44(m, 18H), 7.24(m, 2H), 1.80(s, 12H) |
| 6Gb | $C_{30}H_{36}N_2$ M+ 664.29 | 8.81(m, 4H), 8.55(d, 2H), 8.31(s, 2H), 8.13-7.97(m, 8H), 7.61(d, 2H), 7.44-7.24(m, 6H), 1.80(s, 12H) |
| 7Gb | $C_{36}H_{38}S_2$ M+ 774.24 | 8.81(d, 2H), 8.31(s, 2H), 8.13-8.02(m, 6H), 7.90-7.80(m, 4H), 7.61(d, 2H), 7.44-7.24(m, 10H), 1.80(s, 12H) |
| 8Gb | $C_{76}H_{52}N_2$ M+ 992.41 | 8.81(d, 2H), 8.31(s, 2H), 8.13-8.02(m, 6H), 7.77-7.00(30H), 1.80(s, 12H) |
| 9Gb | $C_{76}H_{52}N_2$ M+ 992.41 | 8.81(d, 2H), 8.31(s, 2H), 8.13-8.02(m, 6H), 7.61-7.00(30H), 1.80(s, 12H) |
| 10Gb | $C_{76}H_{58}N_2$ M+ 822.17 | 8.81(d, 2H), 8.31(s, 2H), 8.13-8.02(m, 6H), 7.61-7.23(m, 18H), 6.62-6.46(16H), 1.80(s, 12H) |

TABLE 18

| number | LC-MS | NMR |
|---|---|---|
| 11Gb | $C_{64}H_{42}O_2$ M+ 842.32 | 8.81(d, 2H), 8.31(s, 2H), 8.13-8.02(m, 6H), 7.71(s, 2H), 7.61-7.13(m, 18H), 1.80(s, 12H) |
| 12Gb | $C_{64}H_{42}O_2$ M+ 842.32 | 8.81(d, 2H), 8.31(s, 2H), 8.13-8.02(m, 6H), 7.61-7.13(m, 20H), 1.80(s, 12H) |
| 13Gb | $C_{64}H_{42}S_2$ M+ 842.32 | 8.81(d, 2H), 8.31(s, 2H), 8.13-7.24(m, 26H), 1.80(s, 12H) |
| 14Gb | $C_{64}H_{42}S_2$ M+ 842.32 | 8.81(d, 2H), 8.31(s, 2H), 8.13-8.02(m, 6H), 7.86-7.24(m, 20H), 1.80(s, 12H) |

Example 1

An anode was prepared by cutting a Corning 15 Ω/cm² (1200 Å) ITO glass substrate to a size of 50 mm×50 mm×0.7 mm, ultrasonically cleaning the glass substrate using isopropyl alcohol and pure water for five minutes each, and then irradiating UV light for 30 minutes and exposing to ozone to clean. Then, the glass substrate was disposed in a vacuum deposition apparatus.

Then, 2-TNATA, which is a known material for forming a HIL, was vacuum deposited on the glass substrate to form a HIL having a thickness of 600 Å, and then 4,4'-bis[N-(1-naphthyl)-N-phenylamino]biphenyl (NPB), as a hole transporting compound, was vacuum deposited on the HIL to form a HTL having a thickness of 300 Å.

2-TNATA

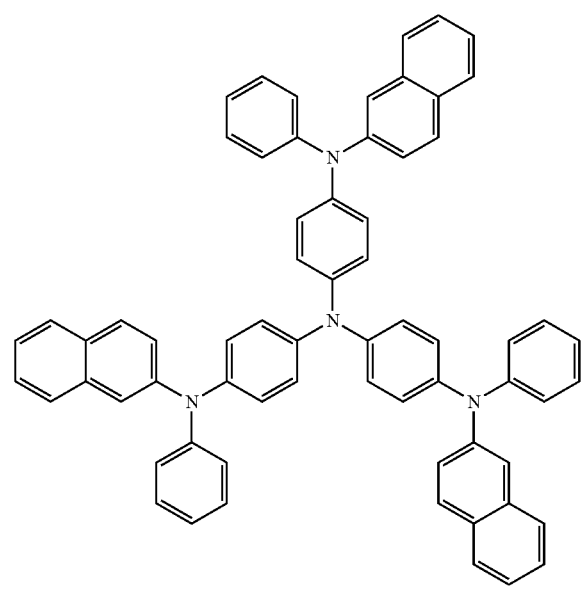

NPB

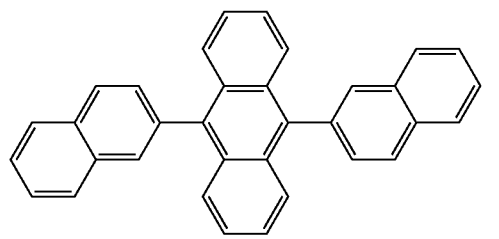

DNA

DPVBi

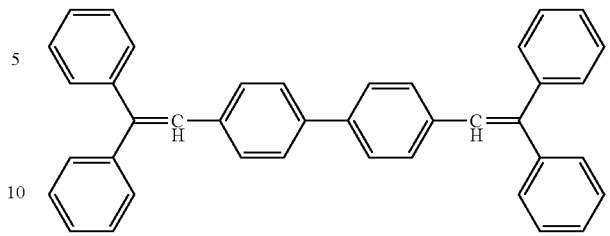

Then,
An organic light-emitting device was manufactured in the same manner as in Example 3, except that Compound 4Gb was used instead of Compound 10Fa to form the EML.

Example 6

An organic light-emitting device was manufactured in the same manner as in Example 1, except that DNA was used as a blue fluorescent host and Compound 4Gb was used as a blue fluorescent dopant form the EML, and Compound 3Ga was used to form the ETL.

Example 7

An organic light-emitting device was manufactured in the same manner as in Example 1, except that DNA was used as a blue fluorescent host and Compound 11Ga was used as a blue fluorescent dopant to form the EML, and Compound 3Ga was used to form the ETL.

Example 8

An organic light-emitting device was manufactured in the same manner as in Example 1, except that DNA was used as a blue fluorescent host and Compound 10Fa was used as a blue fluorescent dopant form the EML, and Compound 6A was used to form the ETL.

Comparative Example 1

An organic light-emitting device was manufactured in the same manner as in Example 1, except that DNA was used as a known blue fluorescent host and 1,4-bis-(2,2-diphenylvinyl)biphenyl (DPVBi) was used as a known blue fluorescent dopant to form the EML, and Alq3 was used instead of Compound 6A to form the ETL.

When the compound of Formula 1, Formula 2, Formula 3 or Formula 4 according to the current embodiments was used as a host or dopant of the EML and as an electron transporting material of the organic light-emitting device, driving voltage of the organic light-emitting device was reduced by 0.7 V or more, efficiency and lifespan were considerably increased, thereby providing excellent I-V-L characteristics, and brightness was increased compared to the organic light-emitting device manufactured using DPVBi and Alq3, which are known material. When the compound according to the current embodiments was used to form the ETL of the organic light-emitting devices according to Examples 1 to 2, driving voltage was reduced by about 1 V, efficiency was increased by 145%, and lifespan was increased by 150% compared with the organic light-emitting device according to Comparative Example 1. When the compound according to the current embodiments was used as a dopant of the organic light-emitting devices according to Examples 3 to 5, driving voltage was reduced by about 1 V, and efficiency and lifespan were respectively increased by 150% or more compared with the organic light-emitting device according to Comparative Example 1. When the compound according to the current embodiments was used to form the ETL and used as a dopant of the organic light-emitting devices according to Examples 6 to 8, driving voltage was reduced by about 1.4 V, efficiency was increased by 150%, and lifespan was increased by 170% compared with the organic light-emitting device according to Comparative Example 1. Characteristics and lifespans of the organic light-emitting devices are shown in Table 19 below.

TABLE 19

| | Dopant or electron transporting material | Driving voltage (V) | Current density (mA/cm$^2$) | Brightness (cd/m$^2$) | Efficiency (cd/A) | Color | Half-life span (hr @100 mA/cm$^2$) |
|---|---|---|---|---|---|---|---|
| Example 1 | ETL 6A | 6.14 | 50 | 2,261 | 4.52 | blue | 194 hr |
| Example 2 | ETL 3Ga | 6.37 | 50 | 2,188 | 4.38 | blue | 189 hr |
| Example 3 | Dopant 10Fa | 6.21 | 50 | 2,402 | 4.80 | blue | 201 hr |
| Example 4 | Dopant 11Ga | 6.57 | 50 | 2,336 | 4.67 | blue | 187 hr |
| Example 5 | Dopant 4Gb | 6.34 | 50 | 2,257 | 4.51 | blue | 193 hr |
| Example 6 | Dopant 4Gb ETL 3Ga | 5.96 | 50 | 2,234 | 4.47 | blue | 205 hr |
| Example 7 | Dopant 11Ga ETL 3Ga | 5.81 | 50 | 2,464 | 4.93 | blue | 227 hr |
| Example 8 | Dopant 10Fa ETL 6A | 5.95 | 50 | 2,319 | 4.64 | blue | 230 hr |
| Comparative Example 1 | Dopant DPVBi ETL Alq3 | 7.35 | 50 | 1,490 | 2.98 | blue | 120 hr |

The heterocyclic compounds according to embodiments of the present invention have excellent light-emitting characteristics and excellent electron transporting characteristics, and thus may be used as electron injecting materials or electron transporting materials suitable for all-color fluorescent and phosphorescent devices, such as red, green, blue, and white fluorescent and phosphorescent devices. In particular, the heterocyclic compounds are efficiently used as light-emitting materials of green, blue, and while fluorescent devices. By using the heterocyclic compounds, organic light-emitting devices having high efficiency, low driving voltage, high brightness, and long lifespan may be prepared.

While the present invention has been particularly shown and described with reference to exemplary embodiments thereof, it will be understood by those of ordinary skill in the art that various changes in form and details may be made therein without departing from the spirit and scope of the present invention as defined by the following claims.

What is claimed is:
1. A compound represented by one of Formulae 1-4:

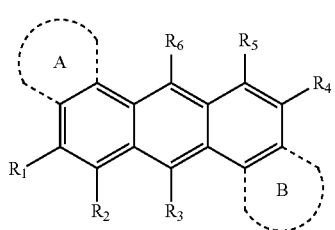

Formula 1

Wherein, in Formula 1, $R_1$, $R_2$, $R_3$, $R_4$, $R_5$, and $R_6$ are each independently a hydrogen atom, a heavy hydrogen atom, a halogen atom, a cyano group, a substituted or unsubstituted $C_1$-$C_{50}$ alkyl group, a substituted or unsubstituted $C_6$-$C_{60}$ aryl group, an amino group substituted with a $C_6$-$C_{50}$ aryl group, a substituted or unsubstituted $C_3$-$C_{60}$ heteroaryl group, or a substituted or unsubstituted $C_6$-$C_{60}$ condensed polycyclic group, and A and B are each independently a substituted or unsubstituted heteroaromatic condensed polycyclic group selected from the group consisting of a substituted or unsubstituted dibenzofuran, a substituted or unsubstituted dibenzothiophene, a substituted or unsubstituted carbazole, and a substituted or unsubstituted indazole, or the A and the B are an unsubstituted 9,9-dimethyl-9H-fluorene;

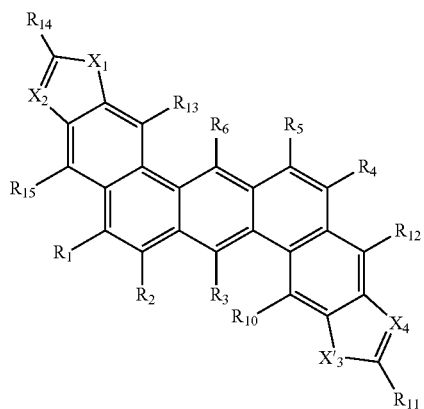

Formula 2

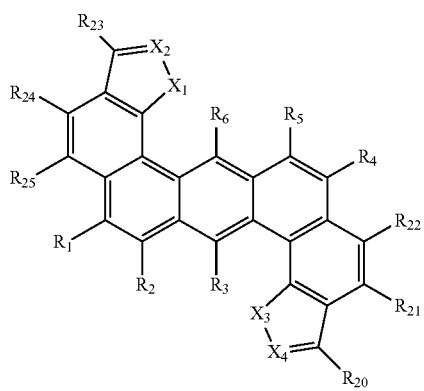

Formula 3

-continued

Formula 4

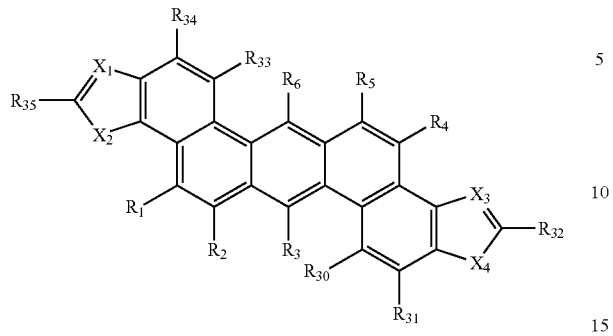

Wherein, in Formulae 2-4, $R_1$ to $R_6$, $R_{10}$ to $R_{15}$, $R_{20}$ to $R_{25}$ and $R_{30}$ to $R_{35}$ are each independently a hydrogen atom, a heavy hydrogen atom, a halogen atom, a cyano group, a substituted or unsubstituted $C_1$-$C_{50}$ alkyl group, a substituted or unsubstituted $C_6$-$C_{60}$ aryl group, an amino group substituted with a $C_6$-$C_{50}$ aryl group, a substituted or unsubstituted $C_3$-$C_{60}$ heteroaryl group, or a substituted or unsubstituted $C_6$-$C_{60}$ condensed polycyclic group;

$X_1$ and $X_3$ are each independently —O—, —N($R_{40}$)—, —C($R_{41}R_{42}$)—, or —S—, $X_2$ and $X_4$ are —C$R_{41}$=; and $R_{40}$ to $R_{42}$ are each independently a hydrogen atom, a heavy hydrogen atom, a halogen atom, a cyano group, a substituted or unsubstituted $C_1$-$C_{50}$ alkyl group, a substituted or unsubstituted $C_6$-$C_{60}$ aryl group, an amino group substituted with a $C_6$-$C_{50}$ aryl group, a substituted or unsubstituted $C_3$-$C_{60}$ heteroaryl group, or a substituted or unsubstituted $C_6$-$C_{60}$ condensed polycyclic group; and Wherein, in Formula 2, optionally, $R_{14}$ and $R_{40}$, $R_{41}$, or $R_{42}$; or $R_{11}$ and $R_{40}$, $R_{41}$, or $R_{42}$ are connected to each other to form a ring;

in Formula 3, optionally, $R_{23}$ and $R_{40}$, $R_{41}$, or $R_{42}$; or $R_{20}$ and $R_{40}$, $R_{41}$, or $R_{42}$ are connected to each other to form a ring; and in Formula 4, optionally, $R_{35}$ and $R_{40}$, $R_{41}$, or $R_{42}$; or $R_{32}$ and $R_{40}$, $R_{41}$, or $R_{42}$ are connected to each other to form a ring.

2. The compound of claim 1, wherein, in Formulae 2, 3, and 4, $R_1$ to $R_6$, $R_{10}$ to $R_{15}$, $R_{20}$ to $R_{25}$, and $R_{30}$ to $R_{35}$ are each independently selected from the group consisting of a hydrogen atom, a heavy hydrogen atom, a halogen atom, a cyano group, a substituted or unsubstituted $C_1$-$C_{20}$ alkyl group, and one of Formulae 2a to 2j below:

2a

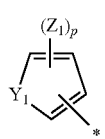

2b

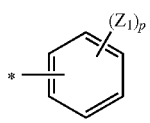

2c

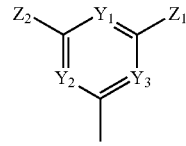

2d

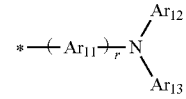

2e

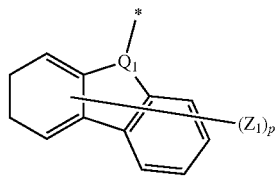

2f

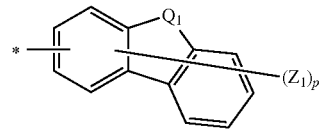

2g

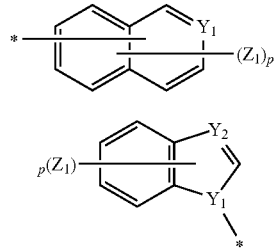

2h

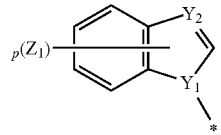

2i

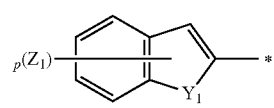

2j

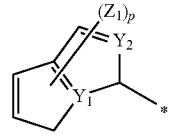

wherein in Formula 2e $Q_1$ is —N(-*)-; and in Formula 2f $Q_1$ is —C($R_{50}$)($R_{51}$)—, —N($R_{52}$)—, —S—, or —O—; $Y_1$, $Y_2$, and $Y_3$ are each independently —N=, —N(-*)-, —S—, —O—, or —C($R_{53}$)=; and wherein $Y_1$, $Y_2$, and $Y_3$ are each independently —N=, or —C($R_{53}$)= in Formula 2c; $Y_1$ is not —N=, or —C($R_{53}$)= in Formulae 2a; $Y_1$ is —N=, or —C($R_{53}$)= in Formula 2g; $Y_1$ is —N(-*)-, and $Y_2$ is —N=, or —C($R_{53}$)= in Formulae 2h; $Y_1$ is —C($R_{53}$)=, and $Y_2$ is —N=, or —C($R_{53}$)= in Formula 2j;

$Z_1$, $Z_2$, $Ar_{12}$, $Ar_{13}$, $R_{50}$, $R_{51}$, $R_{52}$, and $R_{53}$ are each independently selected from the group consisting of a hydrogen atom, a heavy hydrogen atom, a substituted or unsubstituted $C_1$-$C_{20}$ alkyl group, a substituted or unsubstituted $C_6$-$C_{20}$ aryl group, a substituted or unsubstituted $C_3$-$C_{20}$ heteroaryl group, a substituted or unsubstituted $C_6$-$C_{20}$ condensed polycyclic group, a halogen atom, a cyano group, a nitro group, a hydroxy group, and a carboxy group;

Ar$_{11}$ is selected from the group consisting of a substituted or unsubstituted C$_1$-C$_{20}$ alkylene group, a substituted or unsubstituted C$_6$-C$_{20}$ arylene group, and a substituted or unsubstituted C$_3$-C$_{20}$ heteroarylene group;

p is an integer from 1 to 3 in Formula 2a, an integer from 1 to 10 in Formulae 2c, 2d, and 2e, an integer from 1 to 7 in Formula 2f, an integer from 1 to 6 in Formula 2g, an integer from 1 to 5 in Formulae 2b, 2h, 2i, and 2j, respectively;

r is an integer from 0 to 5; and

* is a binding site.

3. The compound of claim 1, wherein the compound is represented by one of Formulae 2 through 4, and, in Formulae 2, 3, and 4, R$_2$, R$_3$, R$_5$, R$_6$, R$_{10}$, R$_{12}$, R$_{13}$, R$_{15}$, R$_{21}$, R$_{22}$, R$_{24}$, R$_{25}$, R$_{30}$, R$_{31}$, R$_{33}$, and R$_{34}$ are each independently a hydrogen atom or a heavy hydrogen atom.

4. The compound of claim 1, wherein the compound is represented by one of Formulae 2 through 4, and, the compounds represented by Formulae 2, 3, and 4 are symmetrical compounds.

5. The compound of claim 1, wherein the compound is represented by one of Formulae 2 through 4, and, in Formulae 2, 3, and 4, R$_2$, R$_3$, R$_5$, R$_6$, R$_{10}$, R$_{12}$, R$_{13}$, R$_{15}$, R$_{21}$, R$_{22}$, R$_{24}$, R$_{25}$, R$_{30}$, R$_{31}$, R$_{33}$, and R$_{34}$ are each independently a hydrogen atom or a heavy hydrogen atom; and R$_1$, R$_4$, R$_{11}$, R$_{14}$, R$_{20}$, R$_{23}$, R$_{32}$, and R$_{35}$ are each independently selected from the group consisting of a hydrogen atom, a heavy hydrogen atom, a halogen atom, a cyano group, a substituted or unsubstituted C$_1$-C$_{20}$ alkyl group, and one of Formulae 2a to 2j below:

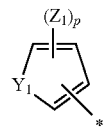

2a

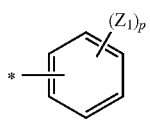

2b

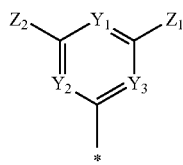

2c

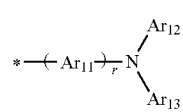

2d

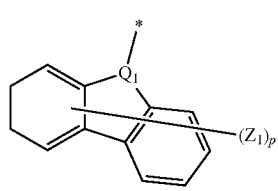

2e

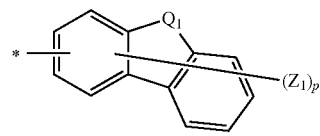

2f

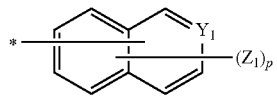

2g

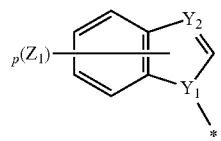

2h

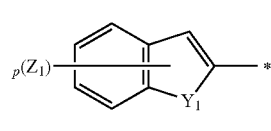

2i

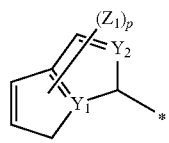

2j wherein in Formula 2e Q$_1$ is —N(-*)-; and in Formula 2f Q$_1$ is —C(R$_{50}$)(R$_{51}$)—, —N(R$_{52}$)—, —S—, or —O—;

Y$_1$, Y$_2$, and Y$_3$ are each independently —N=, —N(-*)-, —S—, —O—, or —C(R$_{53}$)=; and wherein Y$_1$, Y$_2$, and Y$_3$ are each independently —N=, or —C(R$_{53}$)= in Formula 2c; Y$_1$ is not —N=, or —C(R$_{53}$)= in Formulae 2a; Y$_1$ is —N=, or —C(R$_{53}$)= in Formula 2g; Y$_1$ is —N(-*)-, and Y$_2$ is —N=, or —C(R$_{53}$)= in Formulae 2h; Y$_1$ is —C(R$_{53}$)=, and Y$_2$ is —N=, or —C(R$_{53}$)= in Formula 2j;

Z$_1$, Z$_2$, Ar$_{12}$, Ar$_{13}$, R$_{50}$, R$_{51}$, R$_{52}$, and R$_{53}$ are each independently selected from the group consisting of a hydrogen atom, a heavy hydrogen atom, a substituted or unsubstituted C$_1$-C$_{20}$ alkyl group, a substituted or unsubstituted C$_6$-C$_{20}$ aryl group, a substituted or unsubstituted C$_3$-C$_{20}$ heteroaryl group, a substituted or unsubstituted C$_6$-C$_{20}$ condensed polycyclic group, a halogen atom, a cyano group, a nitro group, a hydroxy group, and a carboxy group;

Ar$_{11}$ is selected from the group consisting of a substituted or unsubstituted C$_1$-C$_{20}$ alkylene group, a substituted or unsubstituted C$_6$-C$_{20}$ arylene group, and a substituted or unsubstituted C$_3$-C$_{20}$ heteroarylene group;

p is an integer from 1 to 3 in Formula 2a, an integer from 1 to 10 in Formulae 2c, 2d, and 2e, an integer from 1 to 7 in Formula 2f, an integer from 1 to 6 in Formula 2g, an integer from 1 to 5 in Formulae 2b, 2h, 2i, and 2j, respectively;

r is an integer from 0 to 5; and

* is a binding site.

6. The compound of claim 1, wherein the compound is represented by one of Formulae 2 through 4, and, in Formulae 2, 3, and 4, R$_2$, R$_3$, R$_5$, R$_6$, R$_{10}$, R$_{12}$, R$_{13}$, R$_{15}$, R$_{21}$, R$_{22}$, R$_{24}$, R$_{25}$, R$_{30}$, R$_{31}$, R$_{33}$, and R$_{34}$ are each independently a hydrogen atom or a heavy hydrogen atom;

R$_1$, R$_4$, R$_{11}$, R$_{14}$, R$_{20}$, R$_{23}$, R$_{32}$, and R$_{35}$ are each independently selected from the group consisting of a hydrogen atom, a heavy hydrogen atom, a halogen atom, a cyano group, a substituted or unsubstituted C$_1$-C$_{20}$ alkyl group, and one of Formulae 2a to 2j below; and the compounds represented by Formulae 2, 3, and 4 are symmetrical compounds:

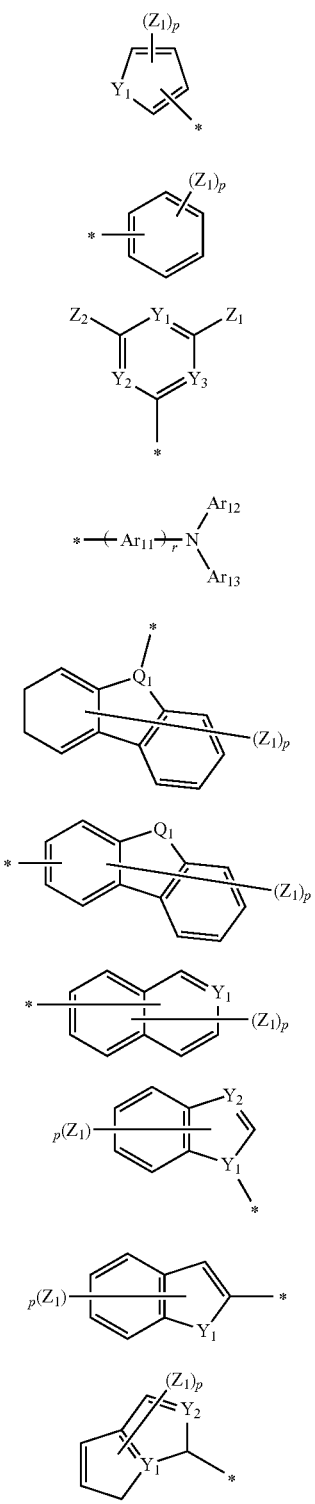

wherein in Formula 2e $Q_1$ is —N(-*)—; and in Formula 2f $Q_1$ is —C($R_{50}$)($R_{51}$)—, —N($R_{52}$)—, —S—, or —O—; $Y_1$, $Y_2$, and $Y_3$ are each independently —N=, —N(-*)-, —S—, —O—, or —C($R_{53}$)=; and wherein $Y_1$, $Y_2$, and $Y_3$ are each independently —N=, or —C($R_{53}$)= in Formula 2c; $Y_1$ is not —N=, or —C($R_{53}$)= in Formulae 2a; $Y_1$ is —N=, or —C($R_{53}$)= in Formula 2g; $Y_1$ is —N(-*)-, and $Y_2$ is —N=, or —C($R_{53}$)= in Formulae 2h; $Y_1$ is —C($R_{53}$)=, and $Y_2$ is —N=, or —C($R_{53}$)= in Formula 2j;

$Z_1$, $Z_2$, $Ar_{12}$, $Ar_{13}$, $R_{50}$, $R_{51}$, $R_{52}$, and $R_{53}$ are each independently selected from the group consisting of a hydrogen atom, a heavy hydrogen atom, a substituted or unsubstituted $C_1$-$C_{20}$ alkyl group, a substituted or unsubstituted $C_6$-$C_{20}$ aryl group, a substituted or unsubstituted $C_3$-$C_{20}$ heteroaryl group, a substituted or unsubstituted $C_6$-$C_{20}$ condensed polycyclic group, a halogen atom, a cyano group, a nitro group, a hydroxy group, and a carboxy group;

$Ar_{11}$ is selected from the group consisting of a substituted or unsubstituted $C_1$-$C_{20}$ alkylene group, a substituted or unsubstituted $C_6$-$C_{20}$ arylene group, and a substituted or unsubstituted $C_3$-$C_{20}$ heteroarylene group;

p is an integer from 1 to 3 in Formula 2a, an integer from 1 to 10 in Formulae 2c, 2d, and 2e, an integer from 1 to 7 in Formula 2f, an integer from 1 to 6 in Formula 2g, an integer from 1 to 5 in Formulae 2b, 2h, 2i, and 2j, respectively;

r is an integer from 0 to 5; and

* is a binding site.

7. The compound of claim 1, wherein the compound is represented by one of the compounds below:

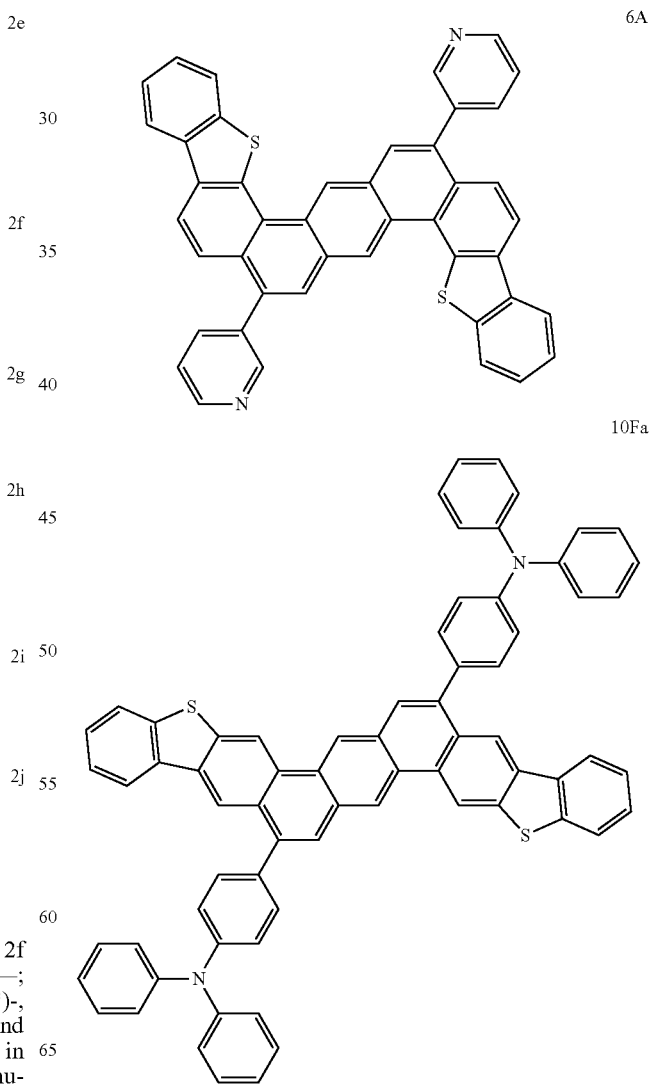

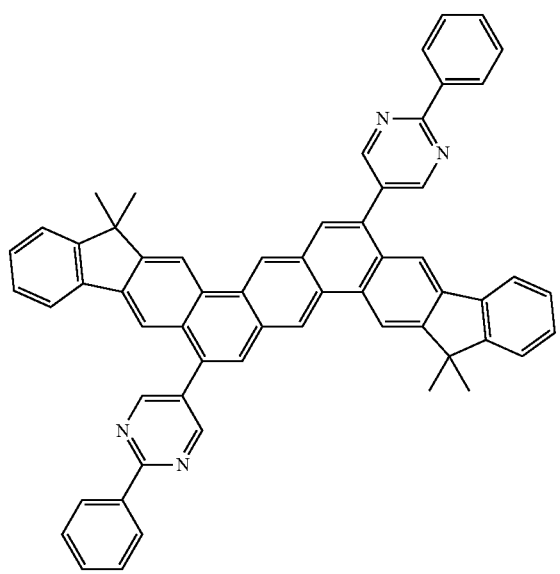 [SMILES: CC1(C)c2ccccc2-c2cc3c(-c4cnc(-c5ccccc5)nc4)cc4cc5c(cc(-c6cnc(-c7ccccc7)nc6)c6cc7c(cc65)C(C)(C)c5ccccc5-7)cc4c3cc21]

3Ga

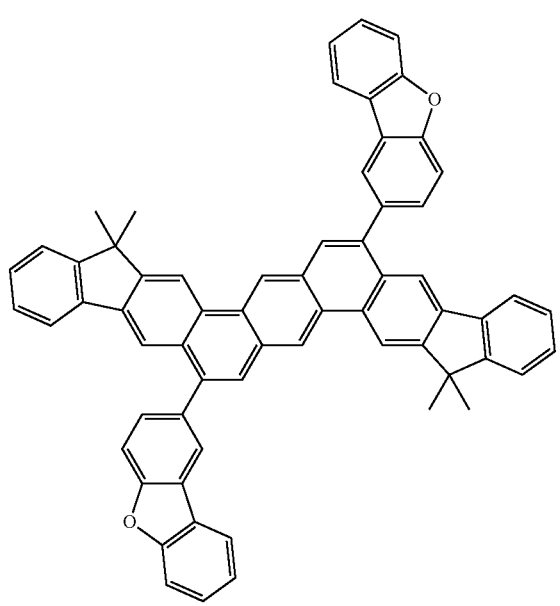 [SMILES: CC1(C)c2ccccc2-c2cc3c(-c4ccc5sc6ccccc6c5c4)cc4cc5c(cc(-c6ccc7sc8ccccc8c7c6)c6cc7c(cc65)C(C)(C)c5ccccc5-7)cc4c3cc21]

11Ga

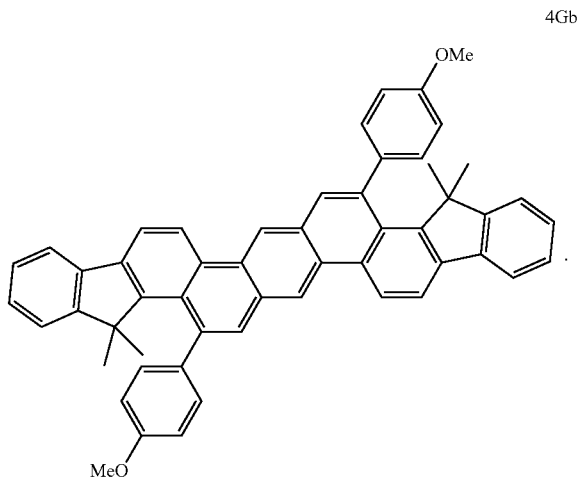

4Gb

8. An organic light-emitting device comprising:
a first electrode;
a second electrode; and
an organic layer interposed between the first electrode and the second electrode, the organic layer comprising a first layer comprising the compound of claim 1.

9. The organic light-emitting device of claim 8, wherein the first layer comprises a hole injection layer, a hole transport layer, a functional layer having both hole injecting and hole transporting capabilities, an emission layer, an electron injection layer, an electron transport layer, or a functional layer having both electron injecting and electron transporting capabilities.

10. The organic light-emitting device of claim 8, wherein the first layer is an emission layer, and the compound is used as a fluorescent host or a fluorescent dopant.

11. The organic light-emitting device of claim 8, wherein the organic layer comprises an emission layer, a hole transport layer, and an electron transport layer; and
the first layer is an emission layer, wherein the emission layer further comprises an anthracene compound, an arylamine compound or a styryl compound.

12. The organic light-emitting device of claim 8, wherein the organic layer comprises an emission layer, a hole transport layer, and an electron transport layer; and
the first layer is an emission layer comprising at least one of a red layer, a green layer, a blue layer and a white layer, and said at least one of the red, green, blue, and white layers of the emission layer further comprises a phosphorescent compound.

13. The organic light-emitting device of claim 8, wherein the first layer is a blue emission layer.

14. The organic light-emitting device of claim 8, wherein the first layer is a blue emission layer, and the compound is used as a blue dopant.

15. The organic light-emitting device of claim 8, wherein the organic layer comprises a hole injection layer, a hole transport layer, a functional layer having both hole injecting and hole transporting capabilities, an emission layer, a hole blocking layer, an electron transport layer, an electron injection layer, or a combination of at least two thereof.

16. The organic light-emitting device of claim 15, wherein at least one of the hole injection layer, the hole transport layer, and the functional layer having both hole injecting and hole transporting capabilities further comprises a charge-generating material.

17. The organic light-emitting device of claim 15, wherein the electron transport layer comprises an electron transporting material and a metal-containing material.

18. A compound represented by one of Formulae 2-4:

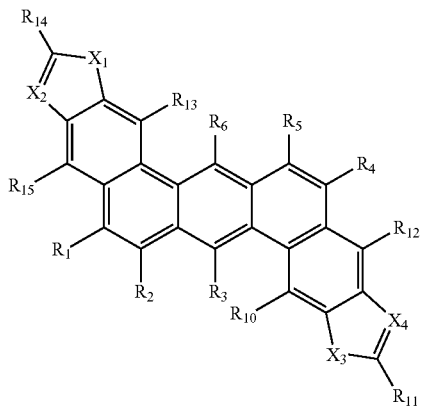

Formula 2

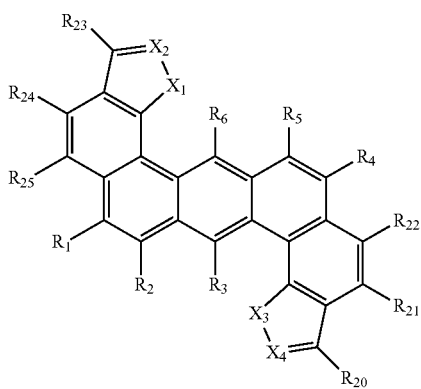

Formula 3

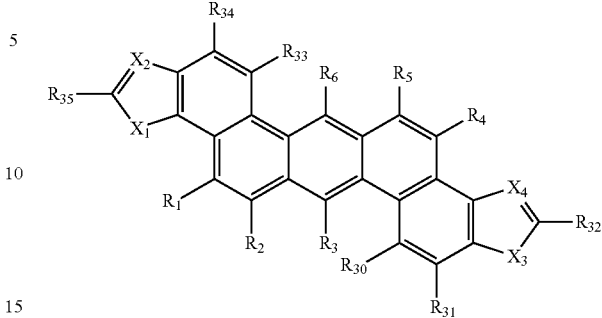

Formula 4

Wherein, in Formulae 2-4, $R_1$ to $R_6$, and $R_{20}$ to $R_{25}$ are each independently a hydrogen atom, a heavy hydrogen atom, a halogen atom, a cyano group, a substituted or unsubstituted $C_1$-$C_{50}$ alkyl group, a substituted or unsubstituted $C_6$-$C_{60}$ aryl group, an amino group substituted with a $C_6$-$C_{50}$ aryl group, a substituted or unsubstituted $C_3$-$C_{60}$ heteroaryl group, or a substituted or unsubstituted $C_6$-$C_{60}$ condensed polycyclic group;

$X_1$ and $X_3$ are —N($R_{40}$)—, and $X_2$ and $X_4$ are —N=; and $R_{40}$ is a hydrogen atom, a heavy hydrogen atom, a halogen atom, a cyano group, a substituted or unsubstituted $C_1$-$C_{50}$ alkyl group, a substituted or unsubstituted $C_6$-$C_{60}$ aryl group, an amino group substituted with a $C_6$-$C_{50}$ aryl group, a substituted or unsubstituted $C_3$-$C_{60}$ heteroaryl group, or a substituted or unsubstituted $C_6$-$C_{60}$ condensed polycyclic group.

* * * * *